(12) United States Patent
Bassin

(10) Patent No.: US 12,208,202 B2
(45) Date of Patent: Jan. 28, 2025

(54) METHODS AND APPARATUS FOR VENTILATORY TREATMENT OF RESPIRATORY DISORDERS

(71) Applicant: ResMed Pty Ltd, Bella Vista (AU)

(72) Inventor: David John Bassin, Coogee (AU)

(73) Assignee: ResMed Pty Ltd (AU)

( * ) Notice: Subject to any disclaimer, the term of this patent is extended or adjusted under 35 U.S.C. 154(b) by 221 days.

(21) Appl. No.: 17/892,216

(22) Filed: Aug. 22, 2022

(65) Prior Publication Data

US 2022/0395654 A1 Dec. 15, 2022

Related U.S. Application Data

(63) Continuation of application No. 16/461,556, filed as application No. PCT/AU2017/051265 on Nov. 17, 2017, now Pat. No. 11,452,829.

(30) Foreign Application Priority Data

Nov. 18, 2016 (AU) ................................ 2016904724

(51) Int. Cl.
*A61M 16/00* (2006.01)
*A61B 5/00* (2006.01)
(Continued)

(52) U.S. Cl.
CPC ......... *A61M 16/024* (2017.08); *A61B 5/4818* (2013.01); *A61M 16/0066* (2013.01);
(Continued)

(58) Field of Classification Search
CPC ............... A61M 16/00; A61M 16/0051; A61M 16/0057; A61M 16/0066; A61M 16/0069;
(Continued)

(56) References Cited

U.S. PATENT DOCUMENTS 4,944,310 A    7/1990   Sullivan
5,134,995 A *  8/1992   Gruenke ........... A61M 16/0051
                                                 128/207.18
(Continued)

FOREIGN PATENT DOCUMENTS

EP    0651971 A1    5/1995
EP    3056236 A1    8/2016
(Continued)

OTHER PUBLICATIONS

CN Office Action for corresponding CN application No. 2017800833360 dated May 7, 2022.
(Continued)

*Primary Examiner* — Joseph D. Boecker
(74) *Attorney, Agent, or Firm* — Botos Churchill IP Law LLP

(57) ABSTRACT

Apparatus for treating a respiratory disorder in a patient comprises a pressure generator configured to deliver a flow of air at positive pressure to an airway of the patient through a patient interface, a sensor configured to generate a respiratory flow rate signal of the patient, and a controller. The controller may be configured to control the generator to deliver ventilation therapy having a base pressure and a pressure support through the patient interface, detect an apnea from the signal representative of respiratory flow rate of the patient, control the generator to deliver one or more probe breaths to the patient during the apnea, determine patency of the patient's airway from a waveform of the respiratory flow rate signal in response to one of the one or more probe breaths and adjust a set point for pressure of the ventilation therapy in response to the apnea.

20 Claims, 34 Drawing Sheets

(51) Int. Cl.
  *A61M 16/06* (2006.01)
  *A61M 16/10* (2006.01)
  *A61M 16/16* (2006.01)

(52) U.S. Cl.
  CPC ...... *A61M 16/0683* (2013.01); *A61M 16/109* (2014.02); *A61M 16/16* (2013.01); *A61M 2202/0208* (2013.01); *A61M 2205/15* (2013.01); *A61M 2205/18* (2013.01); *A61M 2205/3344* (2013.01); *A61M 2205/3365* (2013.01); *A61M 2205/42* (2013.01); *A61M 2205/502* (2013.01); *A61M 2205/52* (2013.01); *A61M 2230/40* (2013.01); *A61M 2230/42* (2013.01)

(58) Field of Classification Search
  CPC .............. A61M 16/022; A61M 16/024; A61M 16/026; A61M 2016/0033; A61M 2016/0036; A61M 2016/0039; A61M 2016/0042; A61M 2205/3344; A61B 5/0826; A61B 5/4818
  See application file for complete search history.

(56) References Cited

U.S. PATENT DOCUMENTS

| | | | |
|---|---|---|---|
| 5,704,345 A * | 1/1998 | Berthon-Jones | A61F 5/56 128/207.18 |
| 6,532,959 B1 | 3/2003 | Berthon-Jones | |
| 7,866,944 B2 | 1/2011 | Kenyon et al. | |
| 8,636,479 B2 | 1/2014 | Kenyon et al. | |
| 8,638,014 B2 | 1/2014 | Sears | |
| 11,452,829 B2 * | 9/2022 | Bassin | A61B 5/6803 |
| 2002/0043264 A1 * | 4/2002 | Wickham | A61B 5/7278 128/204.23 |
| 2003/0062044 A1 * | 4/2003 | Berthon-Jones | A61B 5/4818 128/204.21 |
| 2004/0112381 A1 | 6/2004 | Ujhazy et al. | |
| 2006/0000475 A1 * | 1/2006 | Matthews | A61M 16/026 128/204.21 |
| 2011/0023874 A1 | 2/2011 | Bath et al. | |
| 2015/0059755 A1 | 3/2015 | Bassin | |
| 2015/0250963 A1 * | 9/2015 | Ramanan | A61M 16/0069 128/204.23 |

FOREIGN PATENT DOCUMENTS

| | | |
|---|---|---|
| JP | 2010227595 A | 10/2010 |
| WO | 2006000017 A1 | 1/2006 |
| WO | 2007101296 A1 | 9/2007 |
| WO | 2008138040 A1 | 11/2008 |
| WO | 2011057362 A1 | 5/2011 |
| WO | 2011057362 A4 | 7/2011 |
| WO | 2013020167 A1 | 2/2013 |
| WO | 2013144827 A1 | 10/2013 |
| WO | 2015188227 A1 | 12/2015 |
| WO | 2016044426 A1 | 3/2016 |
| WO | 2016149743 A1 | 9/2016 |
| WO | 2016170005 A1 | 10/2016 |

OTHER PUBLICATIONS

EP Supplementary Search Report dated Jun. 2, 2020 for EP Application No. 17871511.6.
International Search Report mailed Feb. 27, 2018 for PCT/AU2017/051265.
Office Action for Japanese Patent Application No. 2019-526555, Jul. 9, 2021.
The First Office Action for Chinese Patent Application No. 201780083336.0, Jun. 3, 2021.
West, John B., "Respiratory Physiology", Lippincott Williams & Wilkins, 9th Edition, published 2011.

* cited by examiner

METHODS AND APPARATUS FOR VENTILATORY TREATMENT OF RESPIRATORY DISORDERS

1 CROSS-REFERENCE TO RELATED APPLICATIONS

The present application is a continuation of U.S. patent application Ser. No. 16/461,556, filed May 16, 2019, which is a national phase entry under 35 U.S.C. § 371 of International Application No. PCT/AU2017/051265, filed Nov. 17, 2017, which claims priority from Australian Provisional Patent Application No. AU2016904724, filed Nov. 18, 2016, the entire disclosures of all of which are hereby incorporated herein by reference.

2 STATEMENT REGARDING FEDERALLY SPONSORED RESEARCH OR DEVELOPMENT

Not Applicable

3 SEQUENCE LISTING

Not Applicable

4 BACKGROUND OF THE TECHNOLOGY

4.1 Field of the Technology

The present technology relates to one or more of the detection, diagnosis, treatment, prevention and amelioration of respiratory-related disorders. The present technology also relates to medical devices or apparatus, and their use.

4.2 Description of the Related Art

4.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "Respiratory Physiology", by John B. West, Lippincott Williams & Wilkins, 9th edition published 2011.

A range of respiratory disorders exist. Certain disorders may be characterised by particular events, e.g. apneas, hypopneas, and hyperpneas.

Obstructive Sleep Apnea (OSA), a form of Sleep Disordered Breathing (SDB), is characterized by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory Failure is an umbrella term for respiratory disorders in which patients are unable to ventilate enough to balance the $CO_2$ in their blood if their metabolic activity rises much above rest. Respiratory failure encompasses all of the following conditions.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

4.2.2 Therapies

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD, and Chest Wall disorders. In some forms, the comfort and effectiveness of these therapies may be improved.

Patients receiving non-invasive ventilation, particularly when asleep and/or under sedation, are often subject to upper airway instability and collapse, as in OSA. Such instability and collapse can compromise the effectiveness of the ventilation therapy by reducing or even nullifying the pressure actually reaching the lungs from the ventilator.

The upper airway can be stabilised by maintaining a positive base pressure, referred to herein as the EPAP, upon which ventilatory assistance is superimposed. An insufficient EPAP permits upper airway collapse, while an excessive EPAP may fully stabilise the upper airway but negatively impact on comfort, promote mask leak, or pose cardiovascular complications. The task of choosing an EPAP that is sufficient to generally maintain upper airway stability across the range of sleep states, posture, level of sedation, and progression of disease while avoiding negative side-effects (a task known as EPAP titration) is a significant challenge even for experienced clinicians with the benefit of a full polysomnographic (PSG) study. An appropriately titrated EPAP is a balance between extremes, not necessarily one that prevents all obstructive events. While NIV enjoys growing usage globally, only a fraction of patients are administered NIV with the benefit of a PSG study to titrate the EPAP. In more acute environments, historically there is limited awareness of the effects of sleep and sedation on the efficacy of non-invasive ventilation.

There is therefore a significant need for NIV therapies capable of automatically adjusting the EPAP (i.e. performing "EPAP auto-titration") in dynamic response to the changing condition of an NIV patient's upper airway.

4.2.3 Treatment Systems

These therapies may be provided by a treatment system or device. Such systems and devices may also be used to diagnose a condition without treating it.

A treatment system may comprise a Respiratory Pressure Therapy Device (RPT device), an air circuit, a humidifier, a patient interface, and data management.

4.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cm $H_2O$ relative to ambient pressure. For other forms of therapy, such as the delivery of oxygen, the patient interface may not include a seal sufficient to facilitate delivery to the airways of a supply of gas at a positive pressure of about 10 cm $H_2O$.

4.2.3.2 Respiratory Pressure Therapy (RPT) Device

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisee™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

4.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air. A range of artificial humidification devices and systems are known, however they may not fulfil the specialised requirements of a medical humidifier.

5 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

The present technology comprises methods and apparatus for ventilatory therapy for respiratory disorders that automatically titrate a base pressure of the ventilation to maintain upper airway stability such that the applied ventilatory assistance can reach the lungs of the patient. The auto-titration increases the base pressure by an amount generally proportional to the severity of detected apneas and/or episodes of flow limitation, and decreases the base pressure toward a minimum value in the absence of such episodes. In particular, the adjustment takes into account the open/closed status of the airway during the apnea, as determined by analysis of the flow response to timed backup breaths delivered during the apnea.

According to one form of the present technology, there is provided an apparatus for treating a respiratory disorder in a patient. The apparatus comprises a pressure generator configured to deliver a flow of air at positive pressure to an airway of the patient through a patient interface, a sensor configured to generate a signal representative of respiratory flow rate of the patient, and a controller. The controller is configured to control the pressure generator to deliver ventilation therapy having a base pressure and a pressure support through the patient interface, detect an apnea from the signal representative of respiratory flow rate of the patient, control the pressure generator to deliver one or more probe breaths to the patient during the apnea, determine patency of the patient's airway from a waveform of the respiratory flow rate signal in response to one of the one or more probe breaths, compute an effective duration of the apnea based on the patency of the airway, and adjust a set point for the base pressure of the ventilation therapy in response to the apnea based on the effective duration of the apnea.

According to another form of the present technology, there is provided a method of treating a respiratory disorder in a patient. The method comprises controlling a pressure generator to deliver a ventilation therapy through a patient interface to the patient, the ventilation therapy having a base pressure and a pressure support; detecting, in a controller of the pressure generator, an apnea from a signal representative of respiratory flow rate of the patient; controlling the pressure generator to deliver one or more probe breaths to the patient during the apnea; determining patency of the patient's airway from a waveform of the respiratory flow rate signal in response to one of the one or more probe breaths; computing an effective duration of the apnea based on the patency of the airway; and adjusting a set point for the base pressure of the ventilation therapy in response to the apnea based on the effective duration of the apnea.

According to yet another form of the present technology, there is provided a respiratory therapy system comprising: means for delivering a ventilation therapy through a patient interface to a patient, the ventilation therapy having a base pressure and a pressure support; means for generating a signal representative of respiratory flow rate of the patient; means for detecting an apnea from a the respiratory flow rate signal; means for delivering one or more probe breaths to the patient during the apnea; means for determining patency of the patient's airway from a waveform of the respiratory flow rate signal in response to one of the one or more probe breaths; means for computing an effective duration of the apnea based on the patency of the airway; and means for adjusting a set point for the base pressure of the ventilation therapy in response to the apnea based on the effective duration of the apnea.

According to yet another form of the present technology, there is provided a method of determining patency of the airway during an apnea of a patient. The method comprises: controlling a pressure generator to deliver one or more probe breaths to the patient during the apnea; and determining patency of the airway from a signal representative of respiratory flow rate of the patient during the apnea, wherein the determining is dependent on the shape of a waveform of the respiratory flow rate signal in response to at least one of the one or more probe breaths.

According to yet another form of the present technology, there is provided an apparatus for treating a respiratory disorder in a patient. The apparatus comprises: a pressure generator configured to deliver a flow of air at positive pressure to an airway of the patient through a patient interface; a sensor configured to generate a signal representative of respiratory flow rate of the patient; and a controller configured to: control the pressure generator to deliver ventilation therapy through the patient interface; control the pressure generator to deliver one or more probe breaths to the patient during an apnea of the patient; and determine patency of the airway from a waveform of the respiratory flow rate signal during the apnea, wherein determining the patency is dependent on the shape of the respiratory flow rate waveform in response to at least one of the one or more probe breaths.

According to yet another form of the present technology, there is provided a respiratory therapy system comprising: means for delivering a flow of air at positive pressure to an airway of a patient through a patient interface; means for generating a signal representative of respiratory flow rate of the patient; means for delivering one or more probe breaths to the patient during an apnea of the patient; and means for determining patency of the airway from a waveform of the respiratory flow rate signal during the apnea. The determining patency is dependent on the shape of the respiratory flow rate waveform in response to at least one of the probe breaths.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

6 BRIEF DESCRIPTION OF THE DRAWINGS

The present technology is illustrated by way of example, and not by way of limitation, in the figures of the accompanying drawings, in which like reference numerals refer to similar elements including:

6.1 Treatment Systems

FIG. 1 shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000.

6.2 Respiratory System and Facial Anatomy

FIG. 2 shows an overview of a human respiratory system including the nasal and oral cavities, the larynx, vocal folds, oesophagus, trachea, bronchus, lung, Alveolar sacs, heart and diaphragm.

6.3 Patient Interface

FIG. 3 shows a patient interface in the form of a nasal mask in accordance with one form of the present technology.

6.4 RPT Device

6.5 Humidifier

Figure 5A:
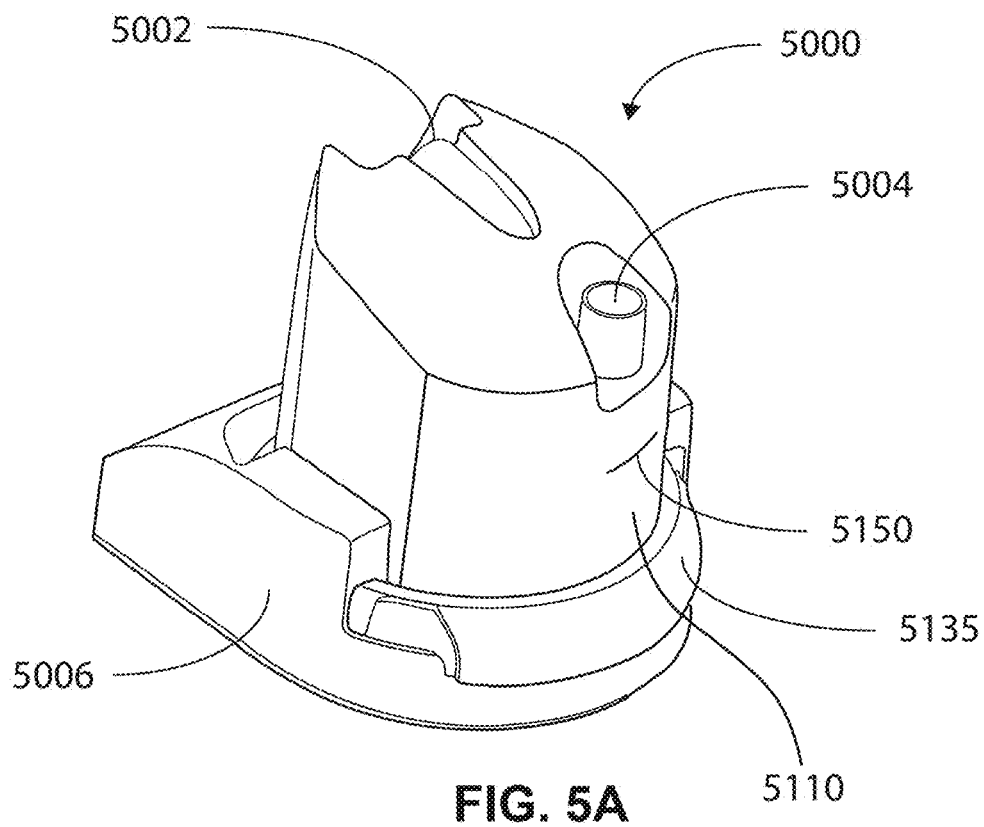

FIG. 5A shows an isometric view of a humidifier in accordance with one form of the present technology.

Figure 5B:
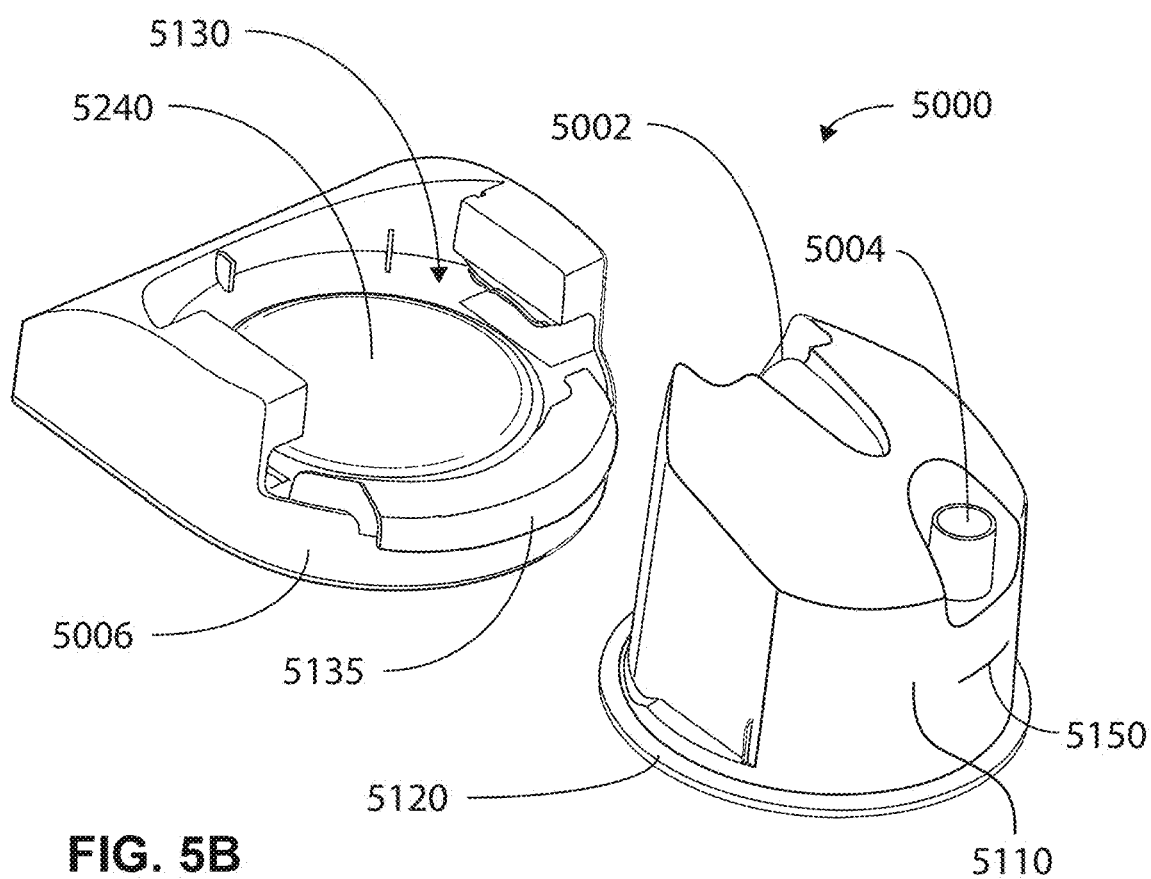

FIG. 5B shows an isometric view of a humidifier in accordance with one form of the present technology, showing a humidifier reservoir 5110 removed from the humidifier reservoir dock 5130.

6.6 Breathing Waveforms

Figure 6A:
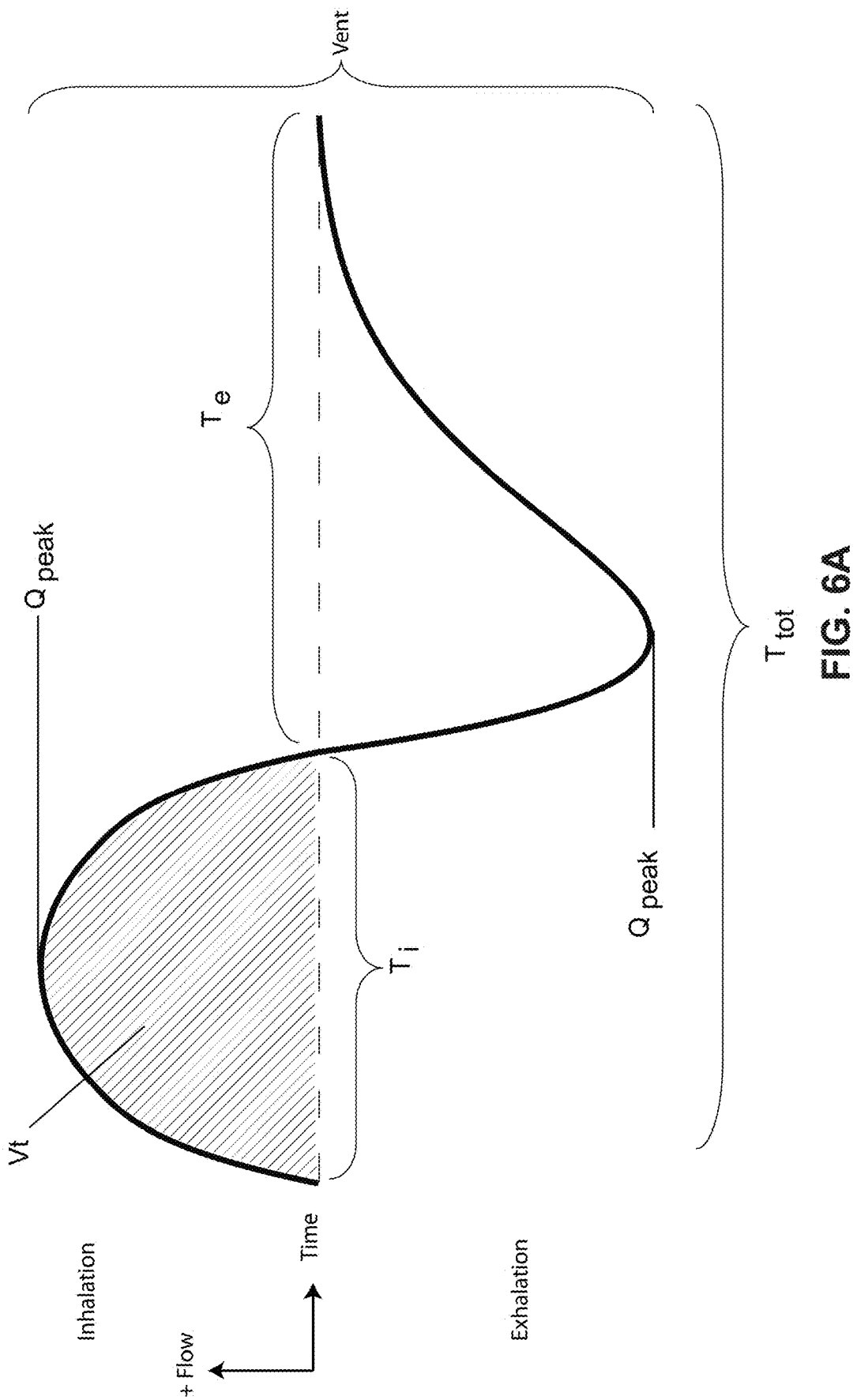

FIG. 6A shows a typical model respiratory flow rate waveform of a person while sleeping. The horizontal axis is time, and the vertical axis is respiratory flow rate. While the parameter values may vary, a typical breath may have the following approximate values: tidal volume, Vt, 0.5 L, inspiratory time, Ti, 1.6 s, peak inspiratory flow rate, Qpeak, 0.4 L/s, expiratory time, Te, 2.4 s, peak expiratory flow rate, Qpeak, −0.5 L/s. The total duration of the breath, Ttot, is about 4 s. The person typically breathes at a rate of about 15 breaths per minute (BPM), with Ventilation, Vent, about 7.5 L/minute. A typical duty cycle, the ratio of Ti to Ttot is about 40%.

Figure 6B:
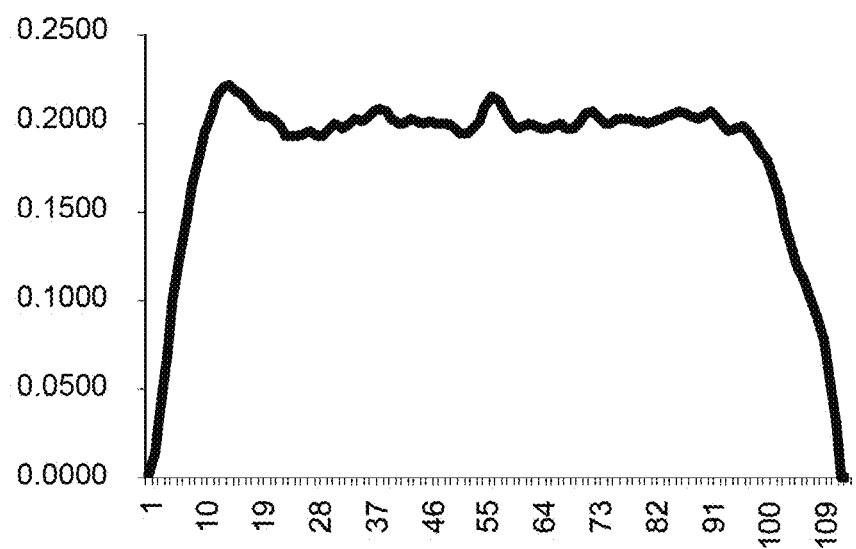

FIG. 6B shows a scaled inspiratory portion of a respiratory flow rate waveform where the patient is experiencing an example of "classical flatness" inspiratory flow limitation.

Figure 6C:

FIG. 6C shows a scaled inspiratory portion of a respiratory flow rate waveform where the patient is experiencing an example of "chair-shaped" (late flatness) inspiratory flow limitation.

Figure 6D:
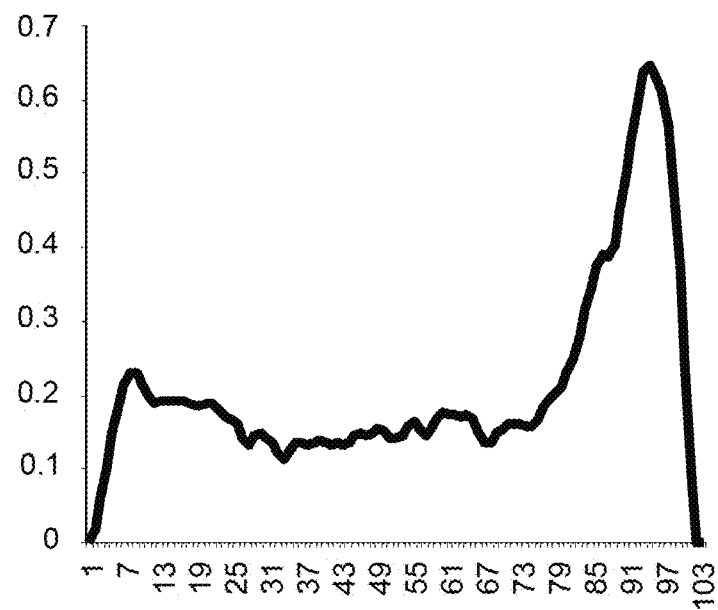

FIG. 6D shows a scaled inspiratory portion of a respiratory flow rate waveform where the patient is experiencing an example of "reverse chair" (early flatness) inspiratory flow limitation.

Figure 6E:
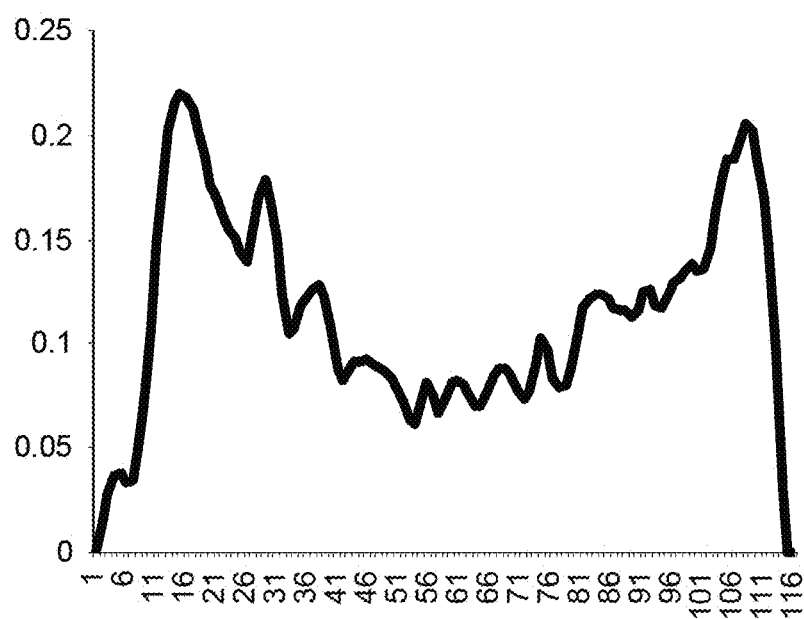

FIG. 6E shows a scaled inspiratory portion of a respiratory flow rate waveform where the patient is experiencing an example of "M-shaped" inspiratory flow limitation.

Figure 6F:
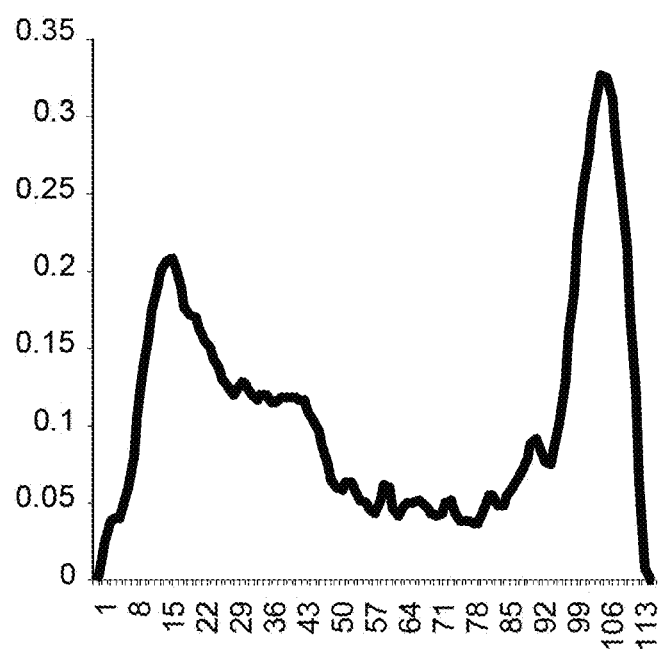

FIG. 6F shows a scaled inspiratory portion of a respiratory flow rate waveform where the patient is experiencing an example of severely "M-shaped" inspiratory flow limitation.

6.7 EPAP Auto-Titration

Figure 1:
Figure 2:
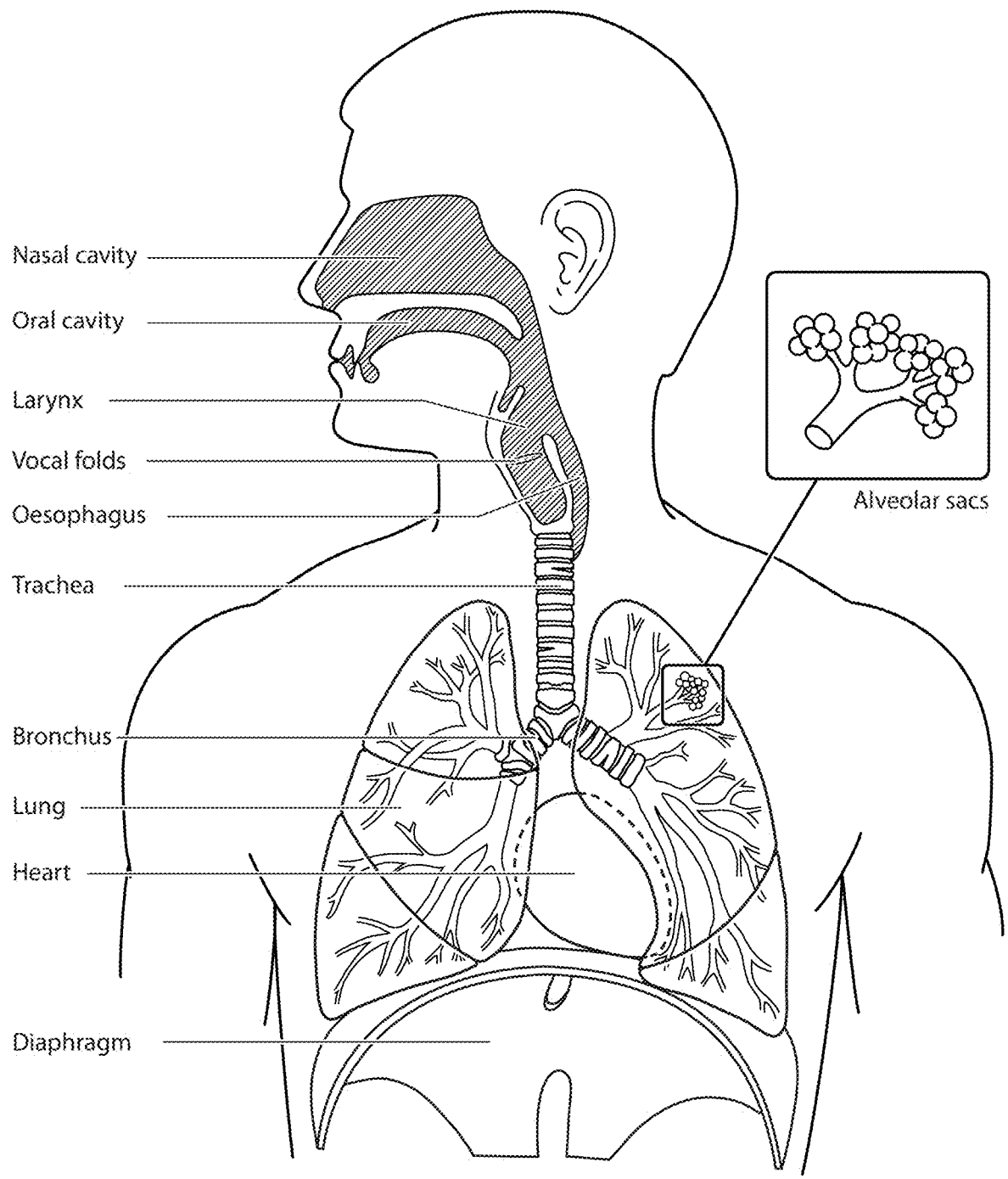
Figure 3:
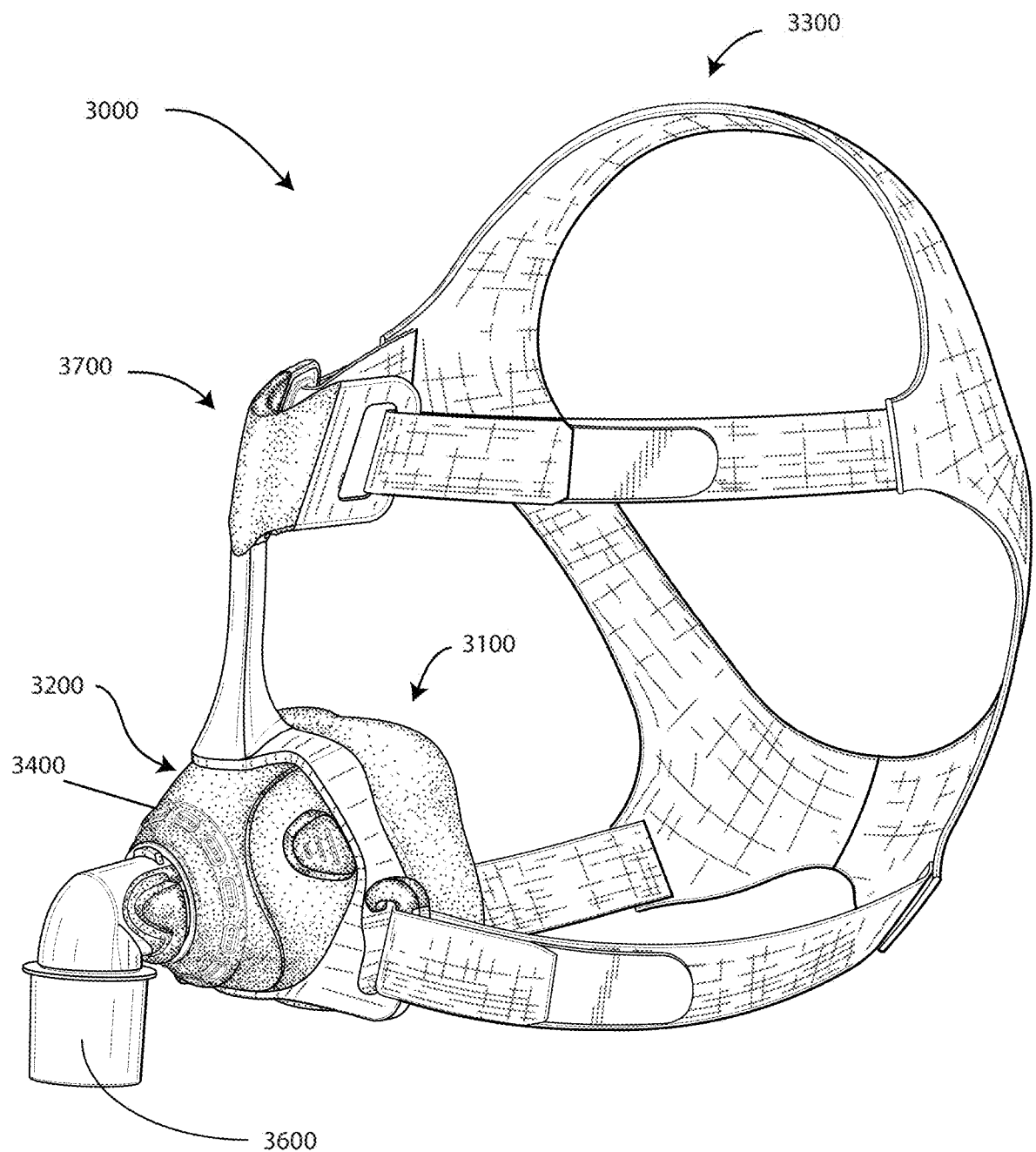
Figure 4A:
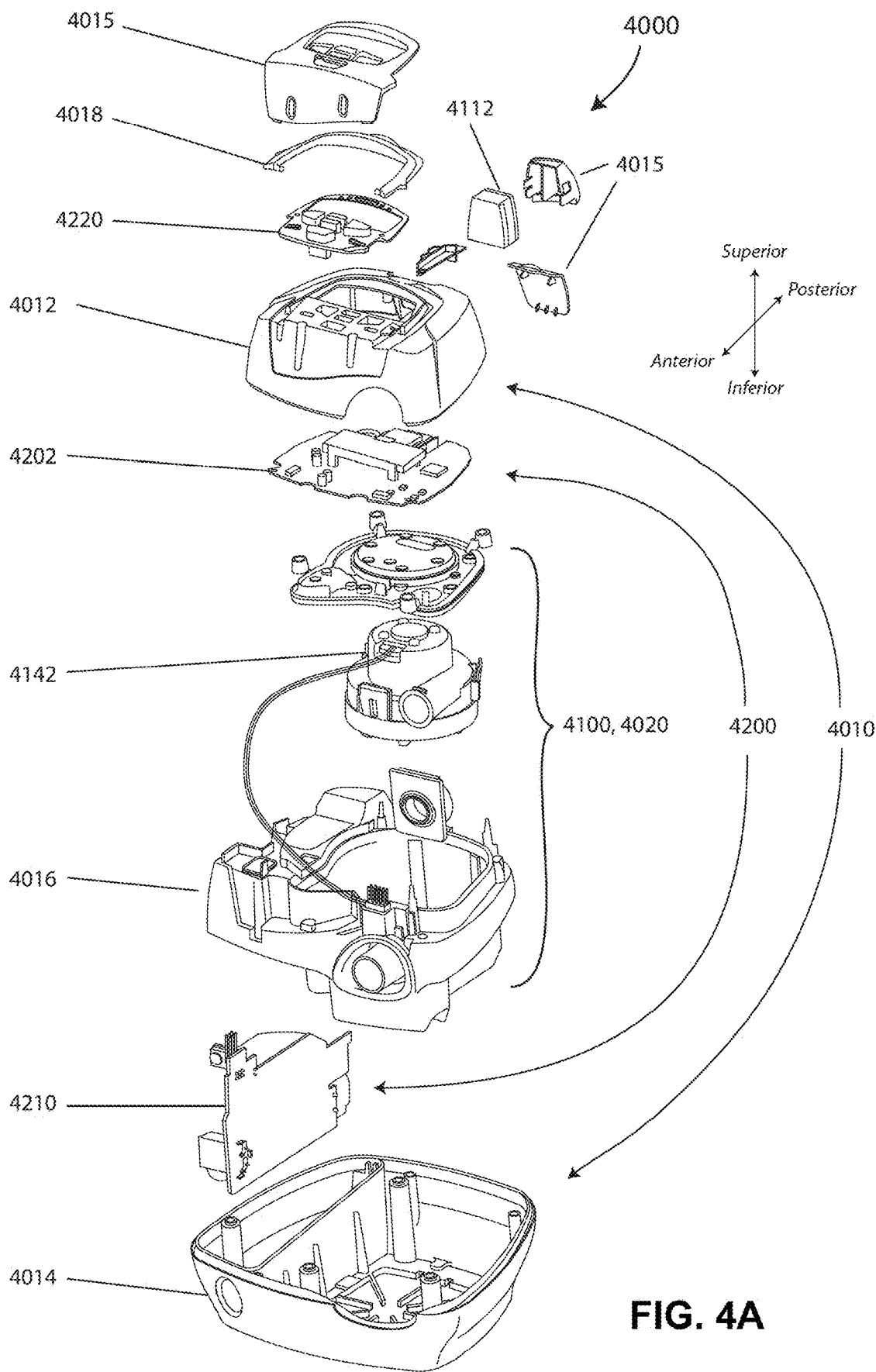
FIG. 4A shows an RPT device in accordance with one form of the present technology.
Figure 4B:
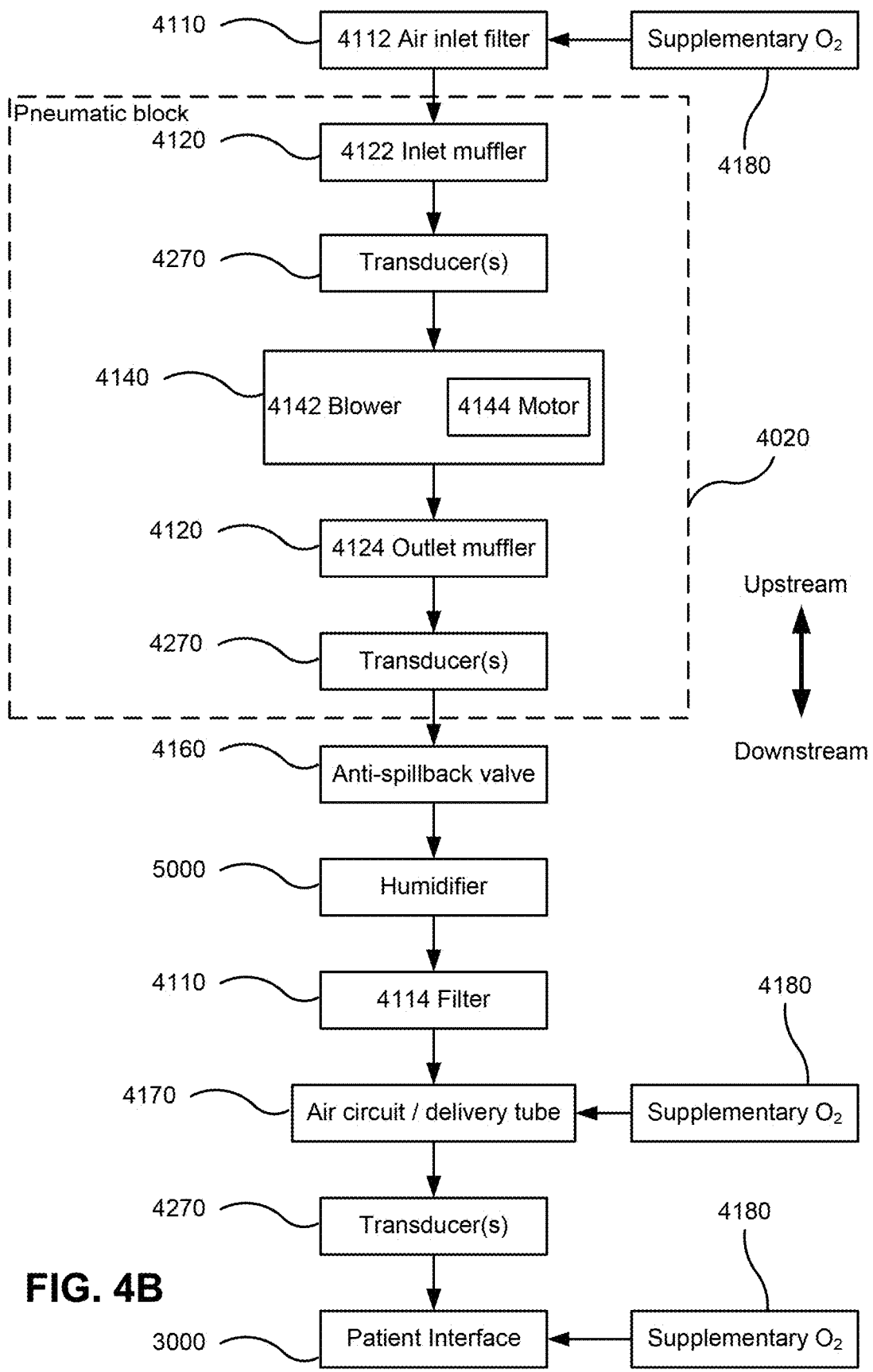
FIG. 4B is a schematic diagram of the pneumatic path of an RPT device in accordance with one form of the present technology. The directions of upstream and downstream are indicated.
Figure 4C:
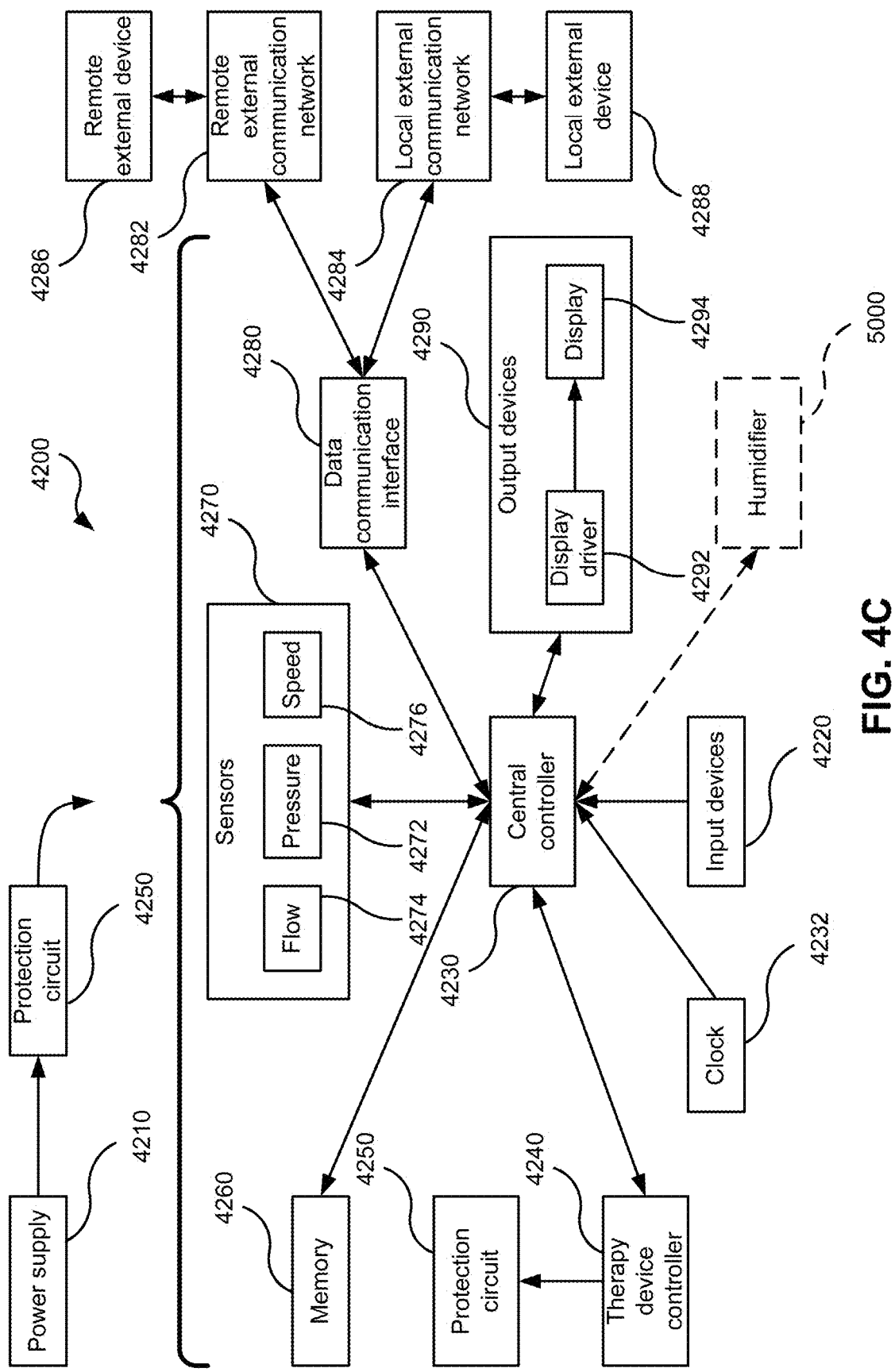
FIG. 4C is a schematic diagram of the electrical components of an RPT device in accordance with one form of the present technology.
Figure 4D:
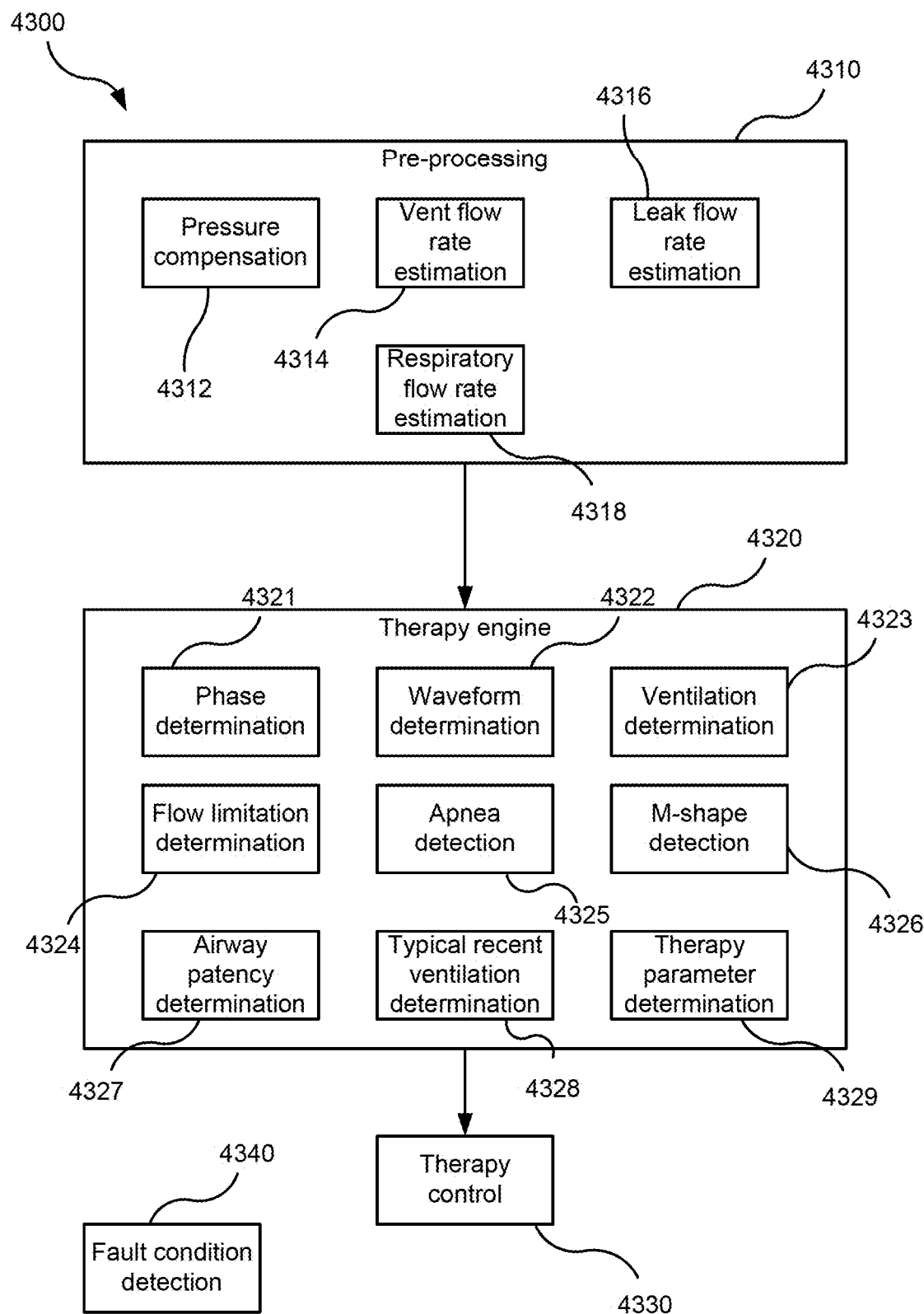
FIG. 4D is a schematic diagram of the algorithms implemented in an RPT device in accordance with one form of the present technology.
Figure 7A:
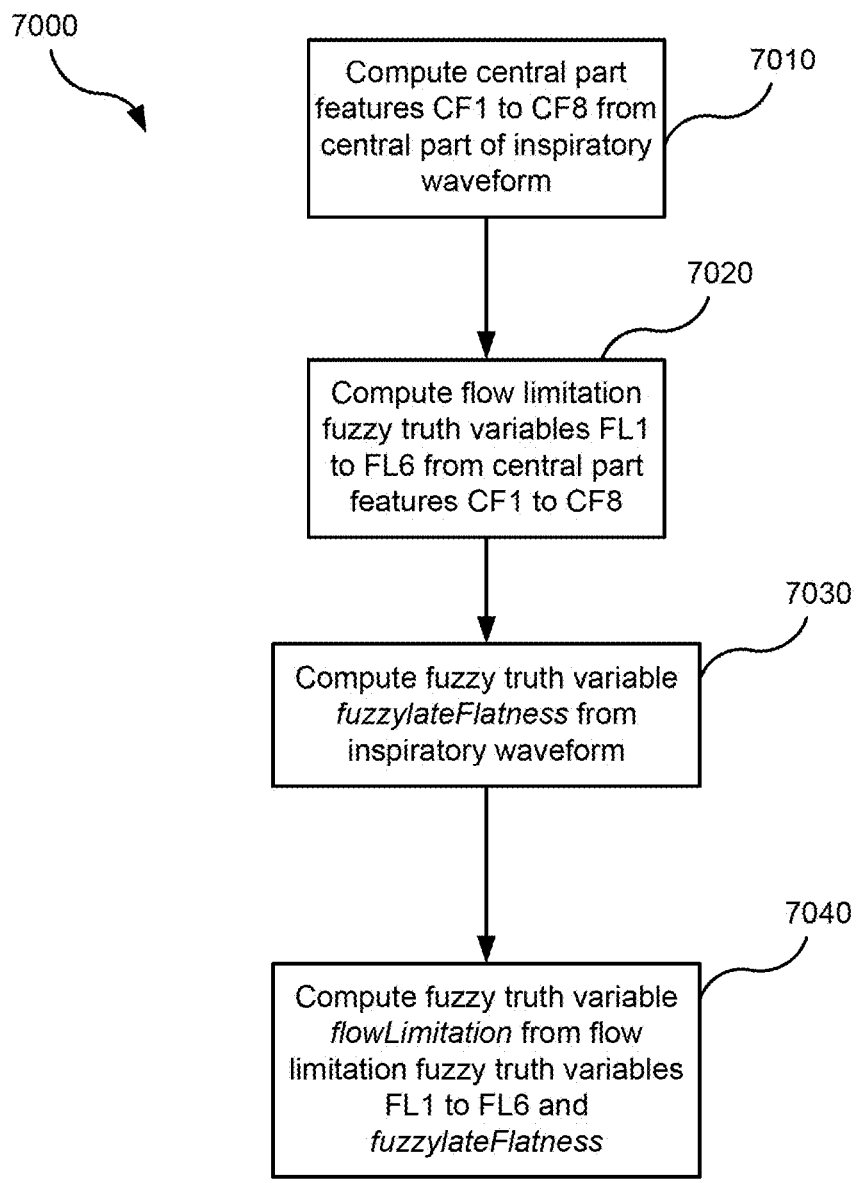

FIG. 7A is a flow chart illustrating a method that may be used to implement the inspiratory flow limitation determination algorithm of FIG. 4D.

Figure 7B:
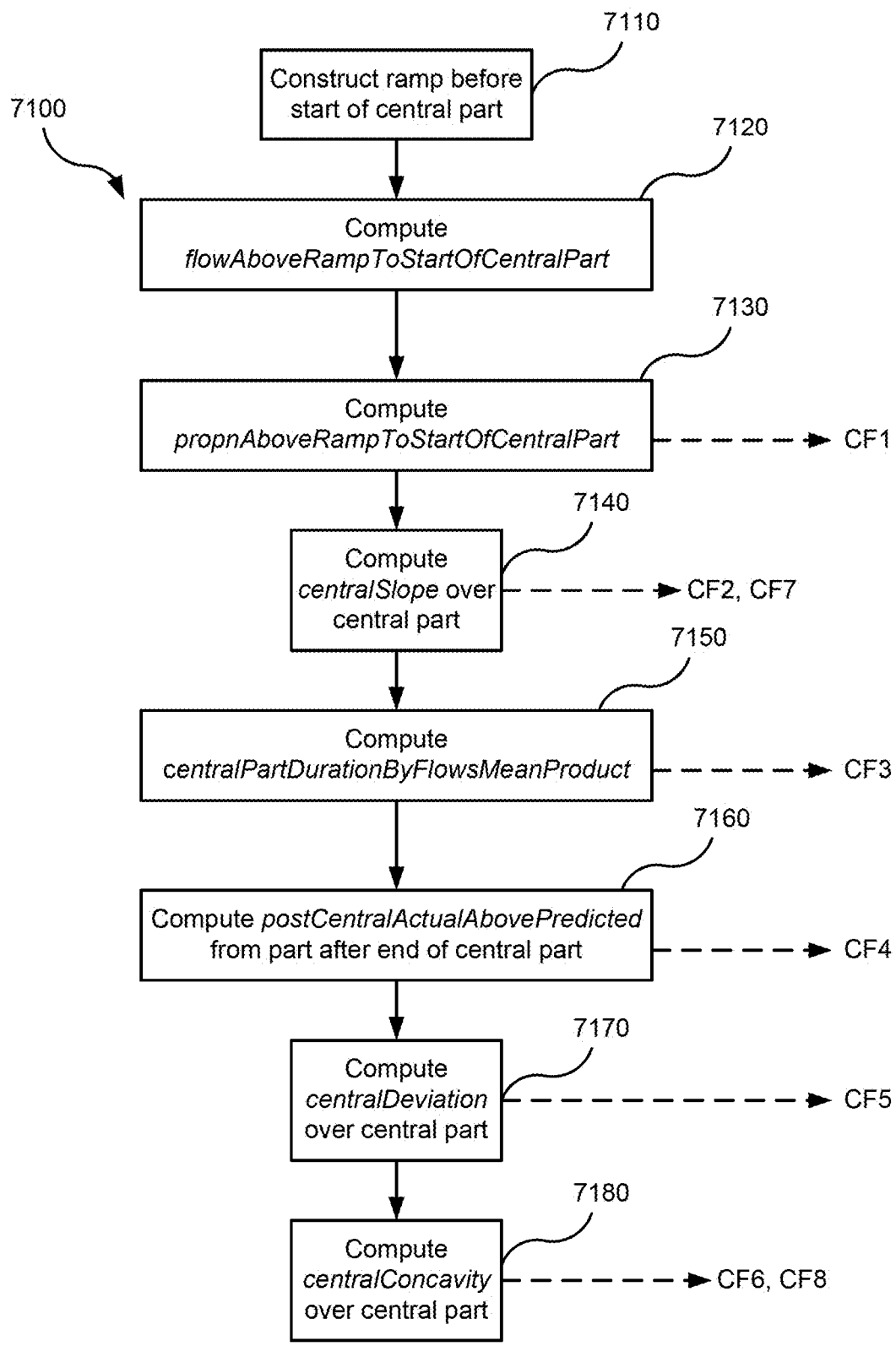

FIG. 7B is a flow chart illustrating a method that may be used to implement the central part feature computation step of FIG. 7A.

Figure 7C:
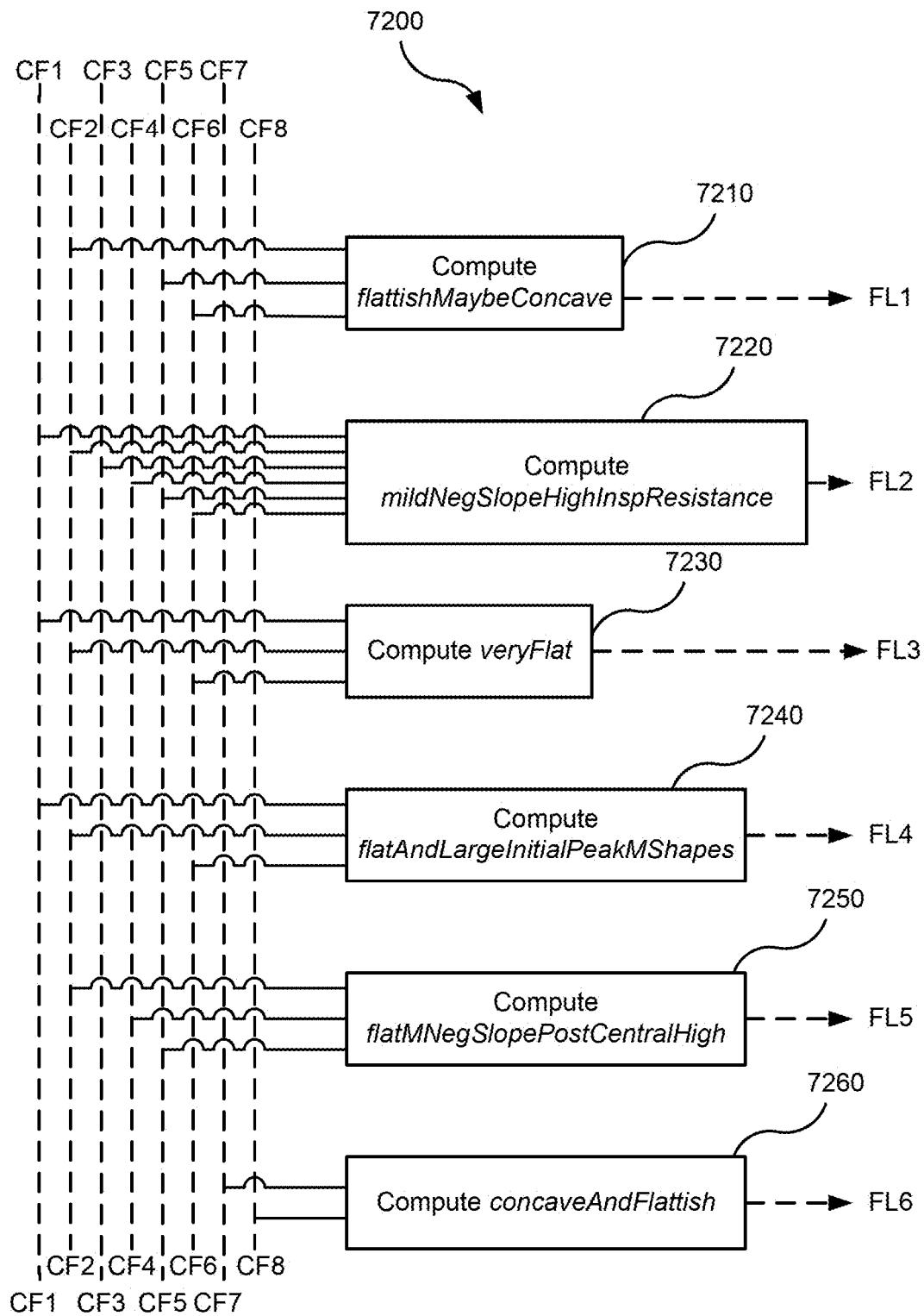

FIG. 7C is a flow chart illustrating a method that may be used to implement the flow limitation fuzzy truth variable computation step of FIG. 7A.

Figure 7D:
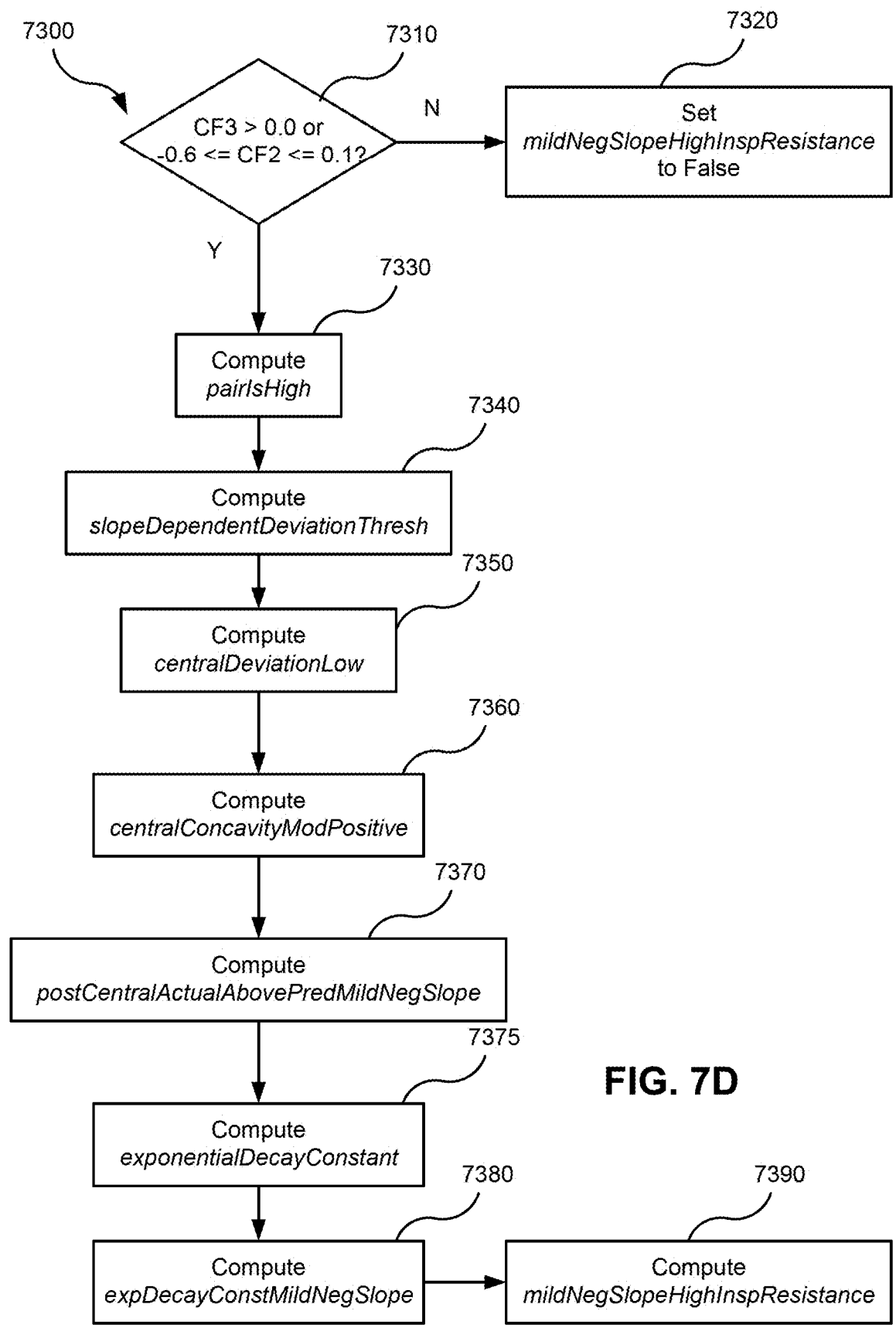

FIG. 7D is a flow chart illustrating a method that may be used to implement one of the flow limitation fuzzy truth variable computation steps of FIG. 7C.

Figure 7E:
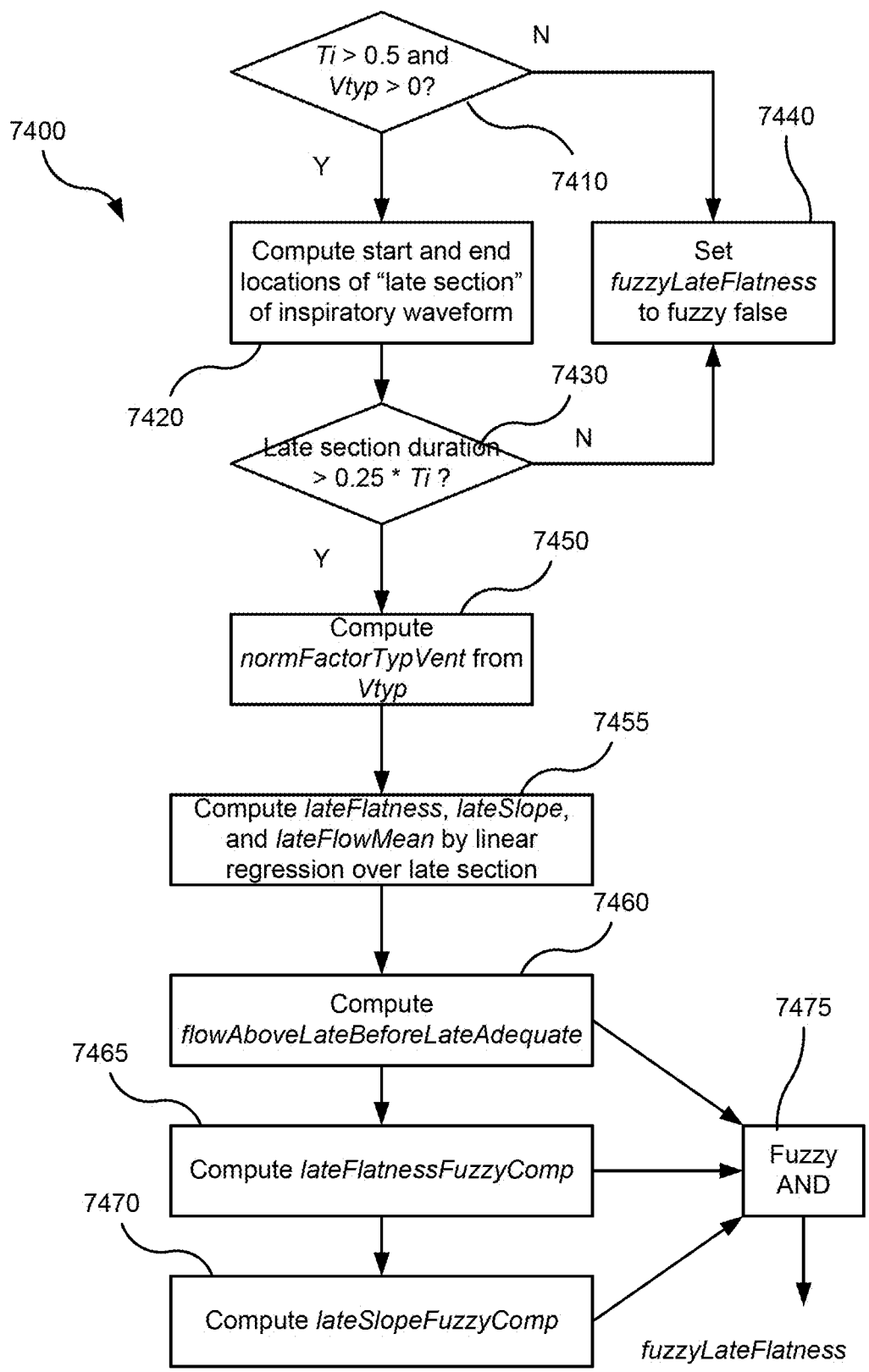

FIG. 7E is a flow chart illustrating a method that may be used to implement the late flatness fuzzy truth variable computation step of FIG. 7A.

Figure 7F:
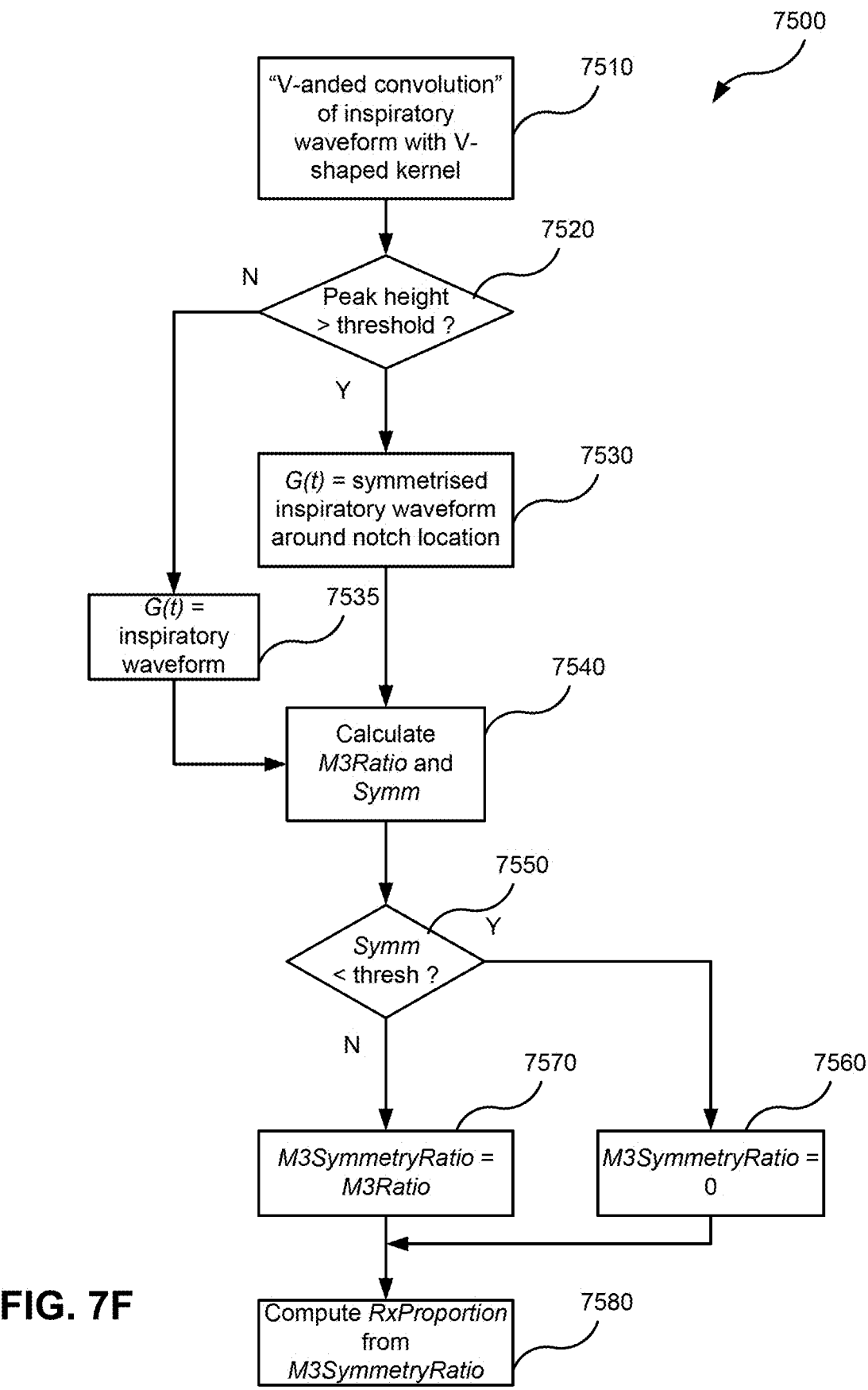

FIG. 7F is a flow chart illustrating a method that may be used to implement the M-shape detection algorithm of FIG. 4D.

Figure 7G:
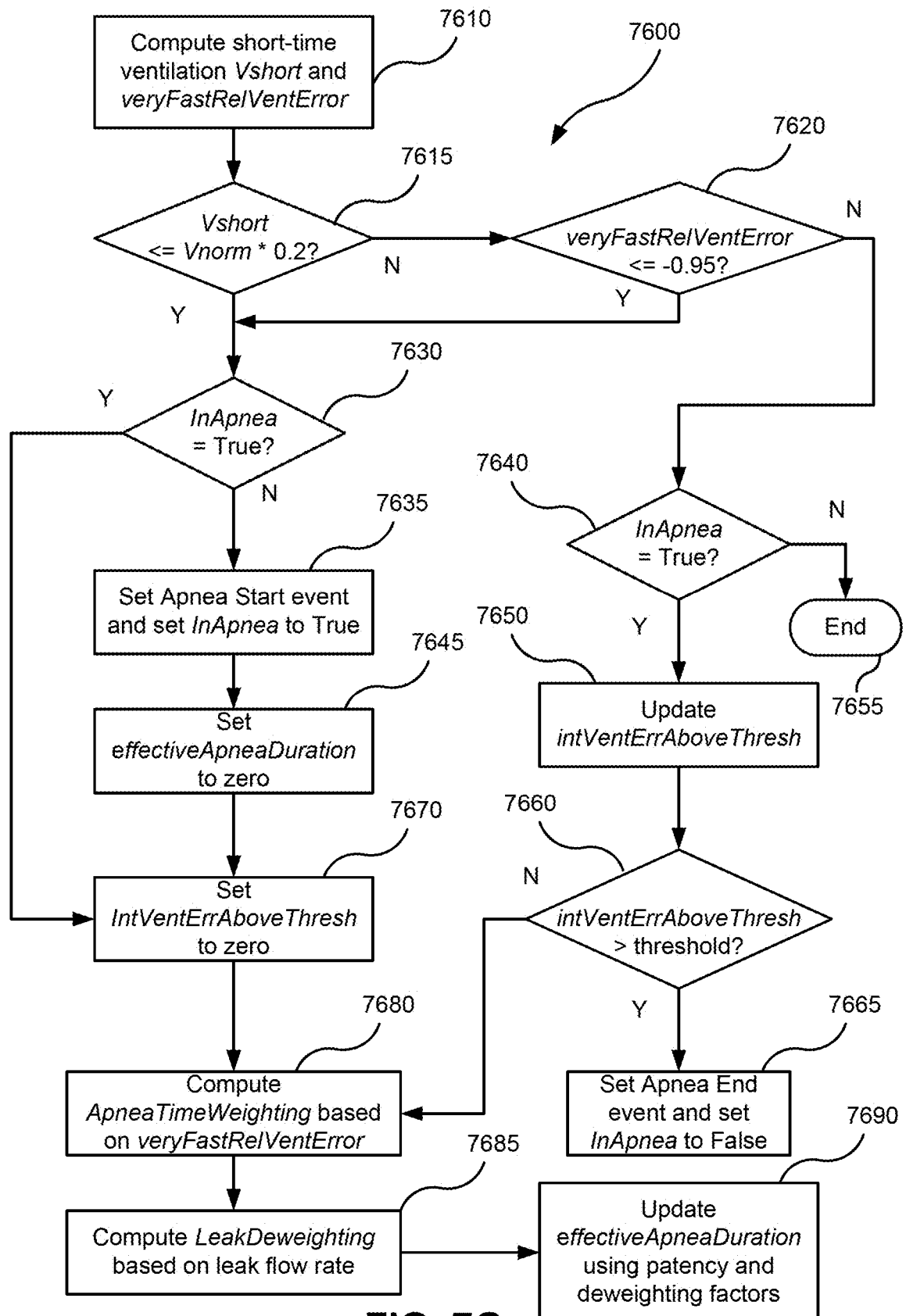

FIG. 7G is a flow chart illustrating a method that may be used to implement the apnea detection algorithm of FIG. 4D.

Figure 7H:
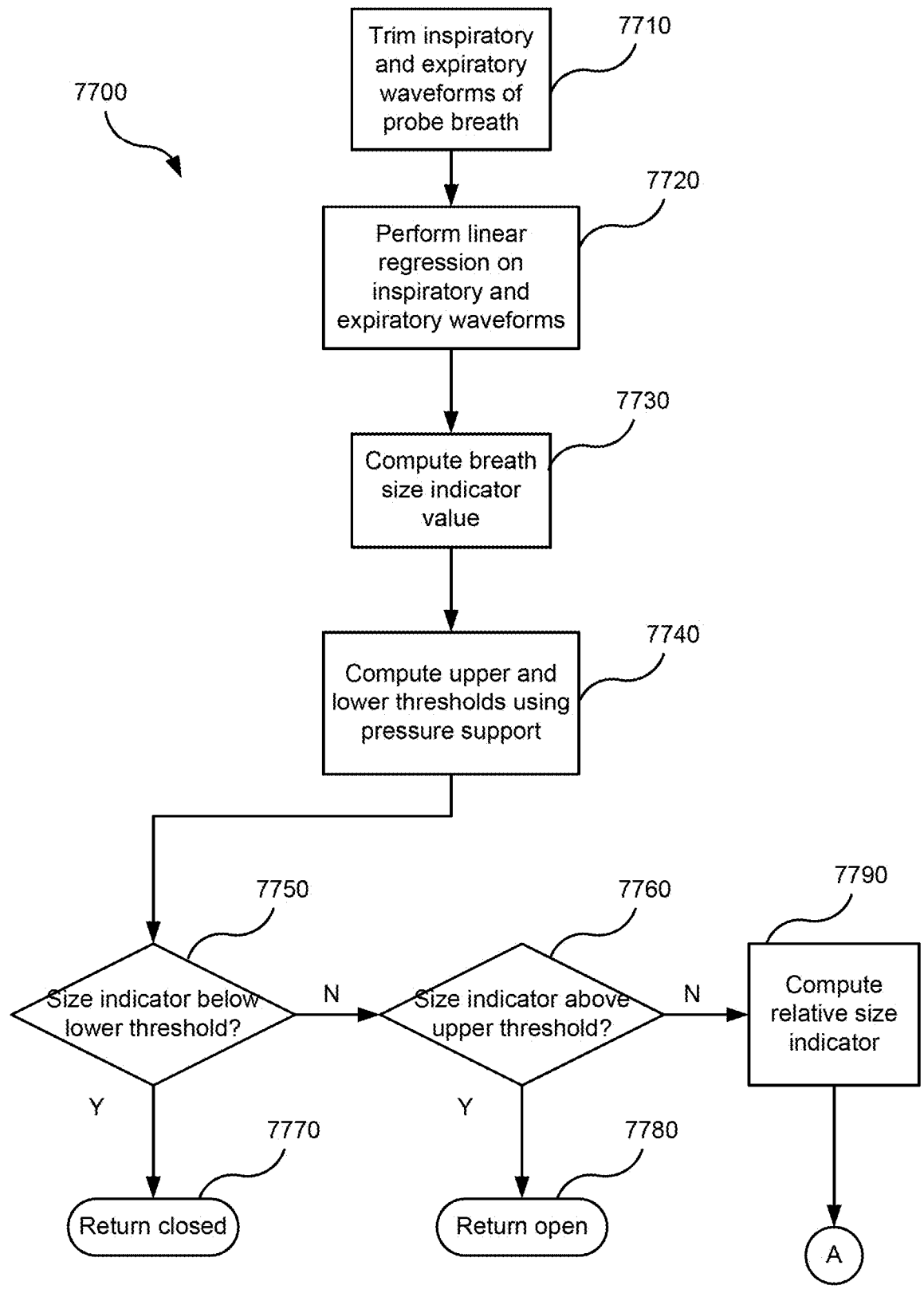
Figure 7I:
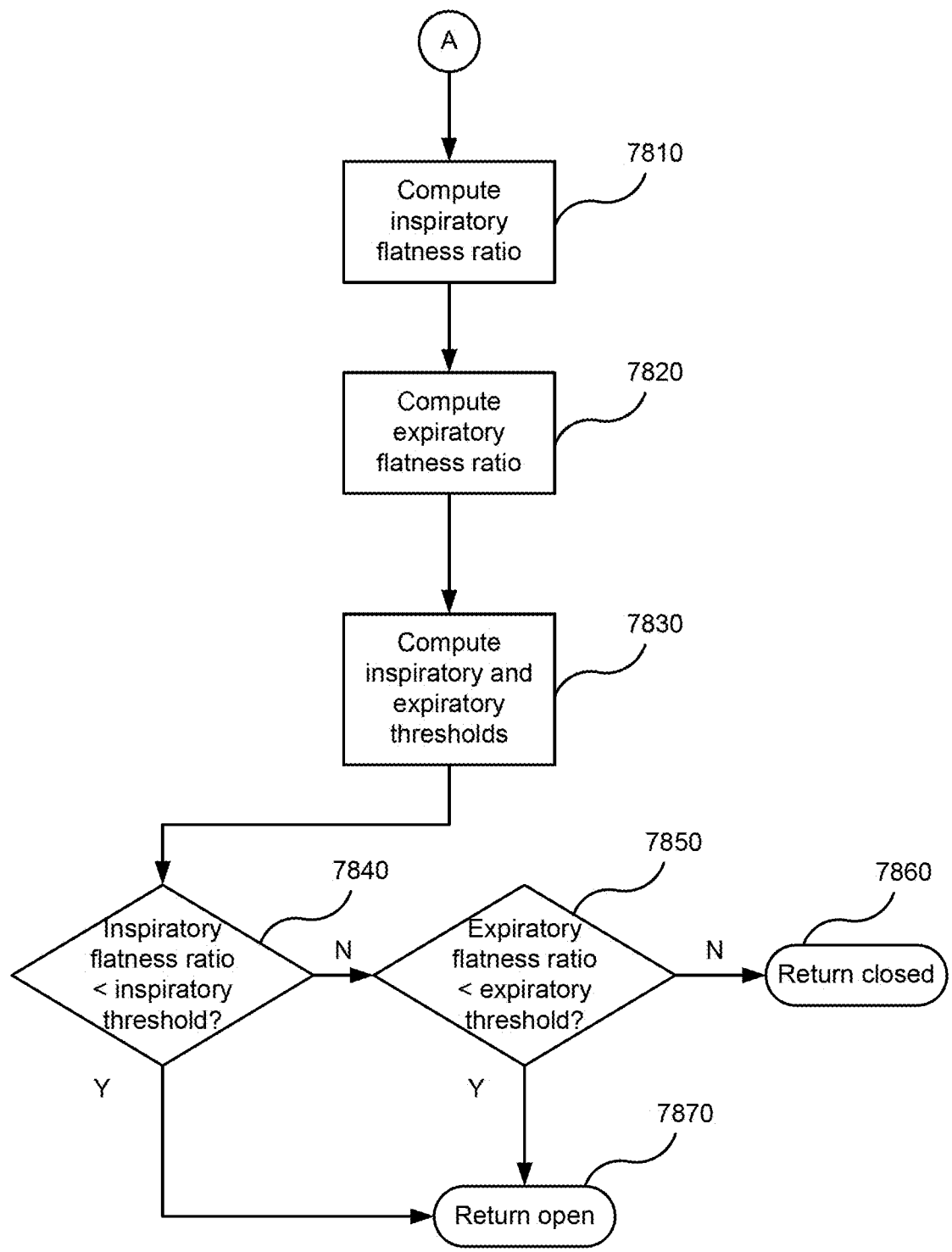

FIGS. 7H and 7I is a flow chart illustrating a method that may be used to implement the airway patency determination algorithm of FIG. 4D.

Figure 8A:
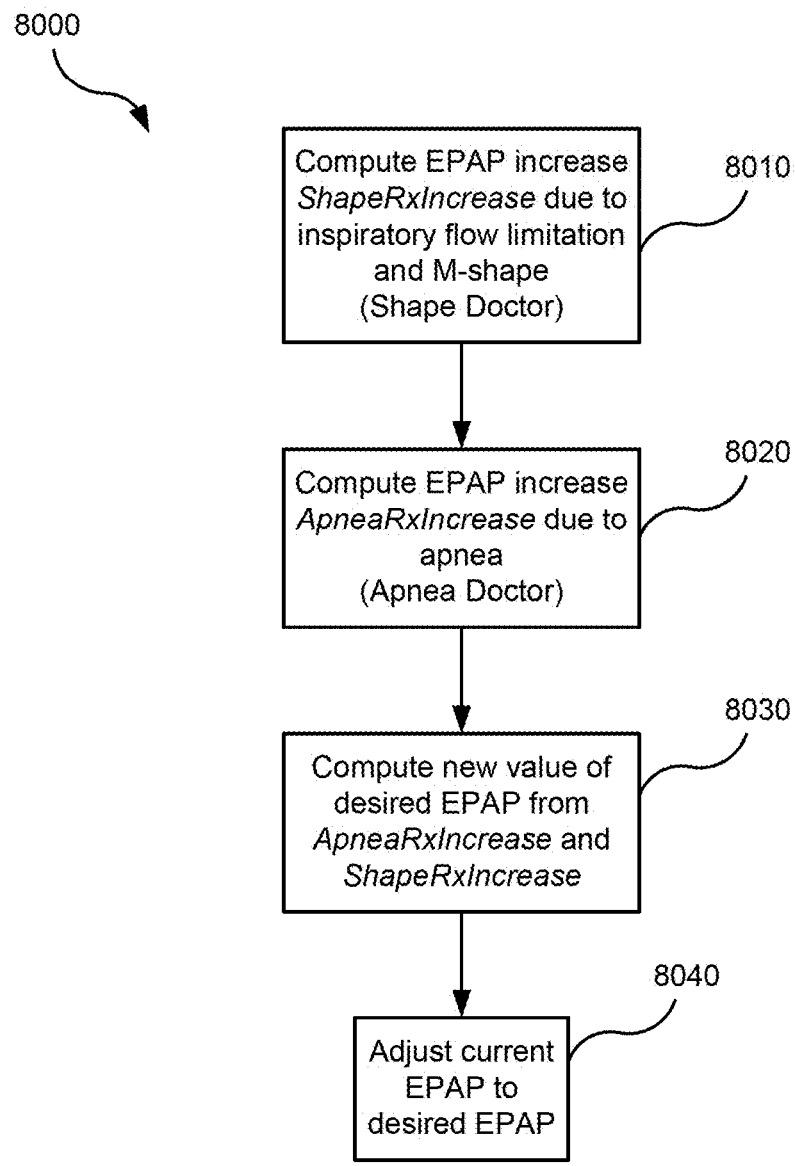

FIG. 8A is a flow chart illustrating a method of auto-titrating the EPAP value that may be implemented by the therapy parameter determination algorithm of FIG. 4D.

Figure 8B:
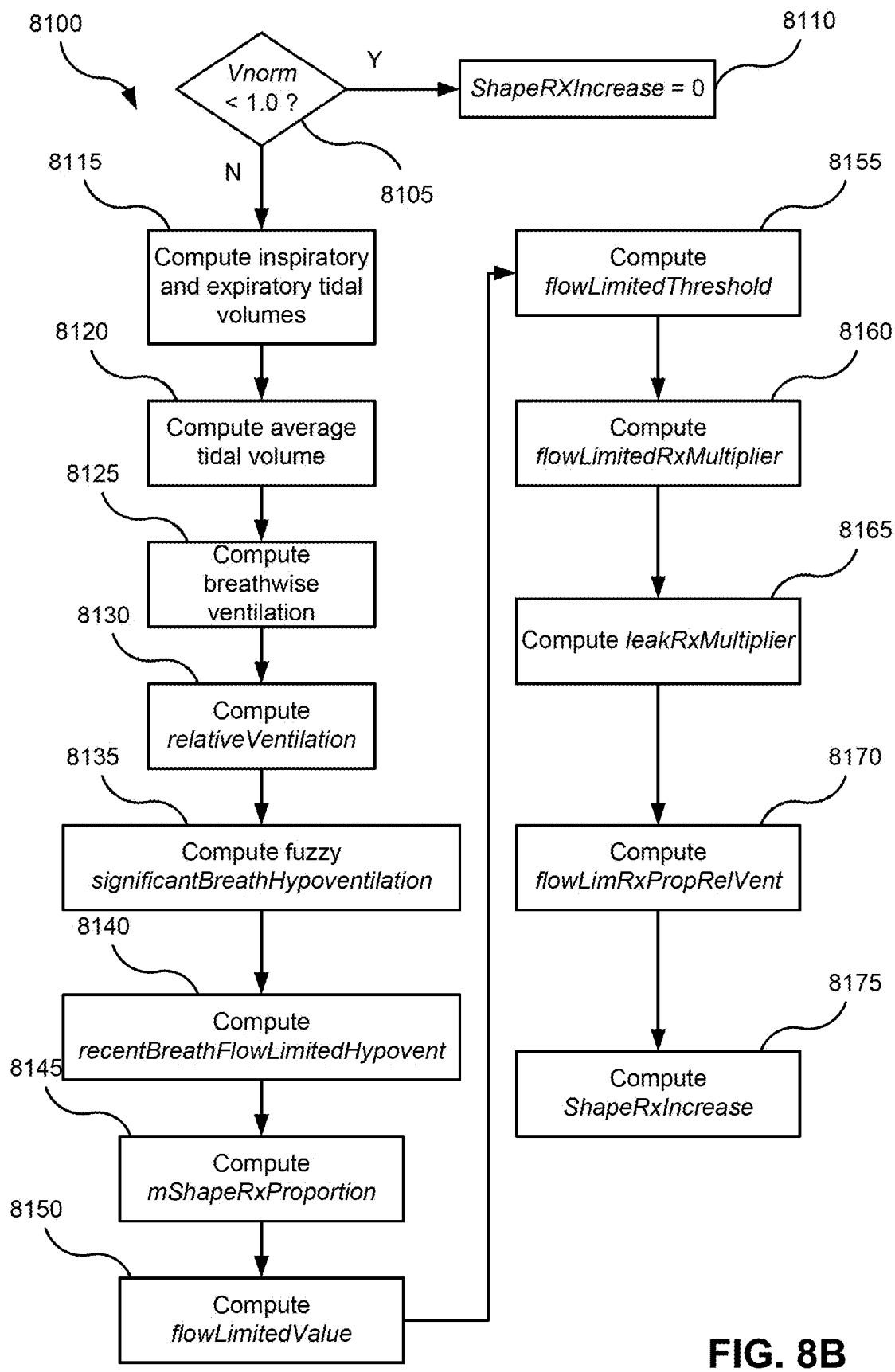

FIG. 8B is a flow chart illustrating a method that may be used to implement the "Shape Doctor" step of the EPAP-auto-titration method of FIG. 8A.

Figure 8C:
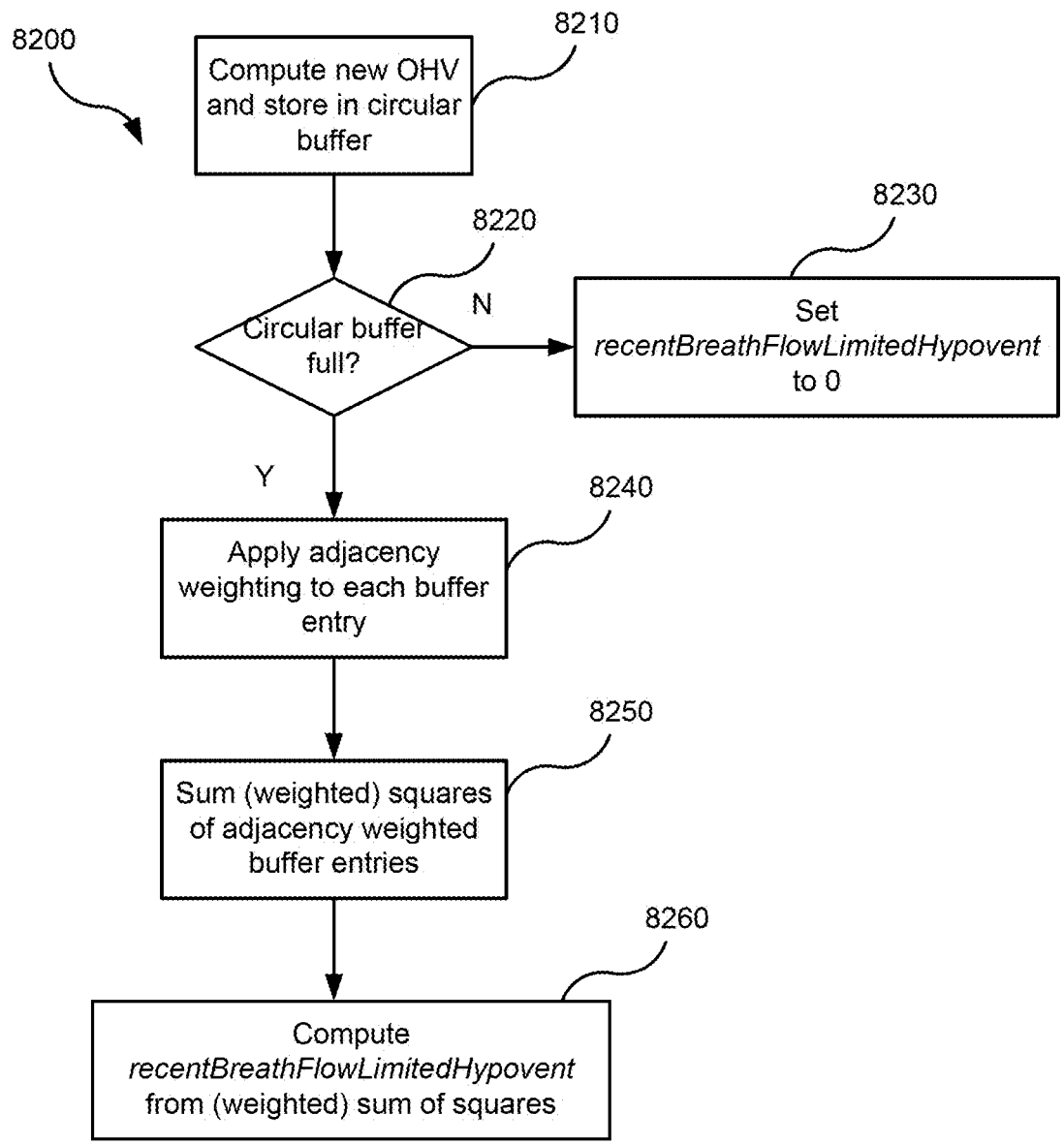

FIG. 8C is a flow chart illustrating a method that may be used to implement one step of the method of FIG. 8B.

Figure 8D:
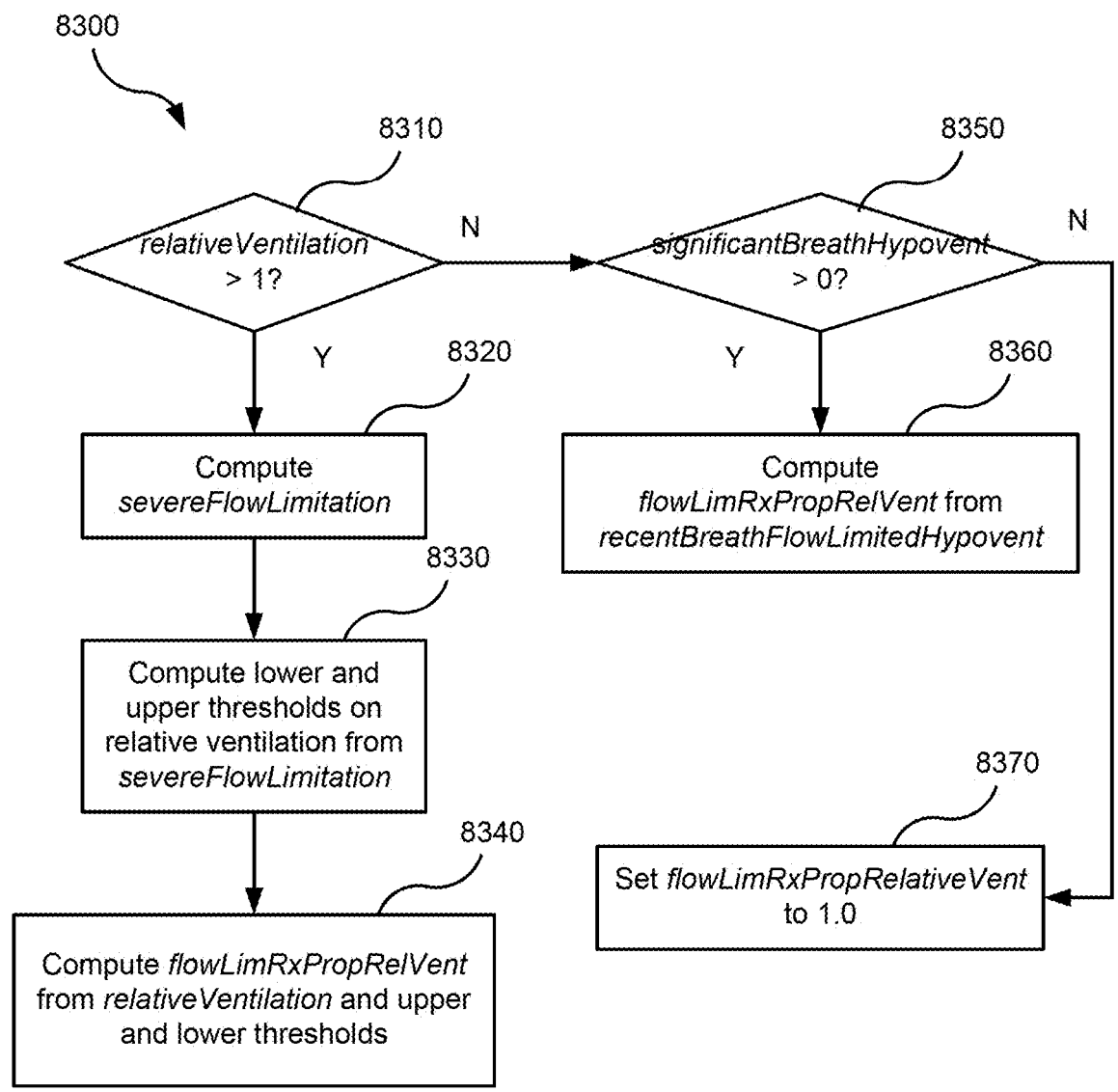

FIG. 8D is a flow chart illustrating a method that may be used to implement another step of the method of FIG. 8B.

Figure 8E:
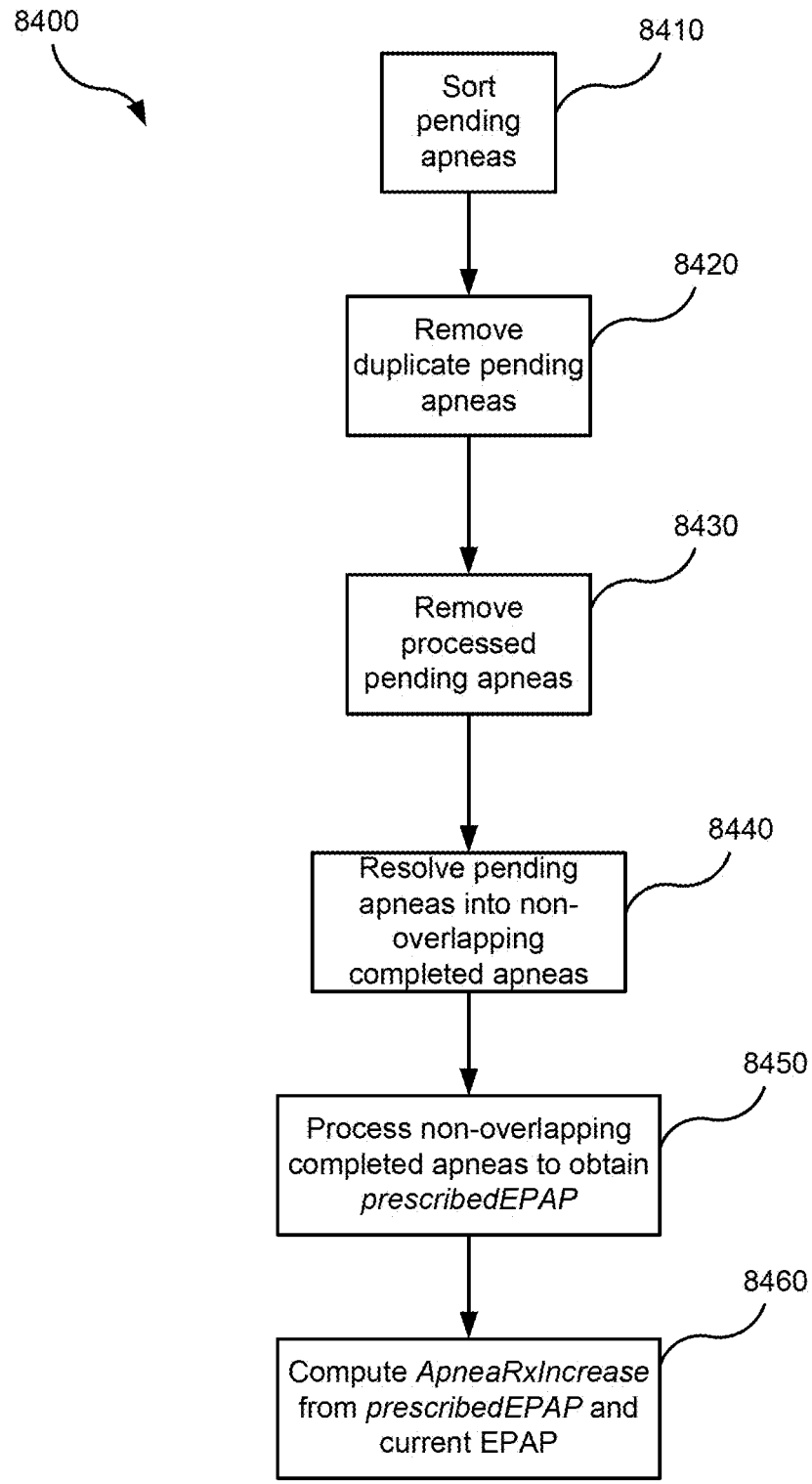

FIG. 8E is a flow chart illustrating a method that may be used to implement the "Apnea Doctor" step of the EPAP-auto-titration method of FIG. 8A.

Figure 8F:
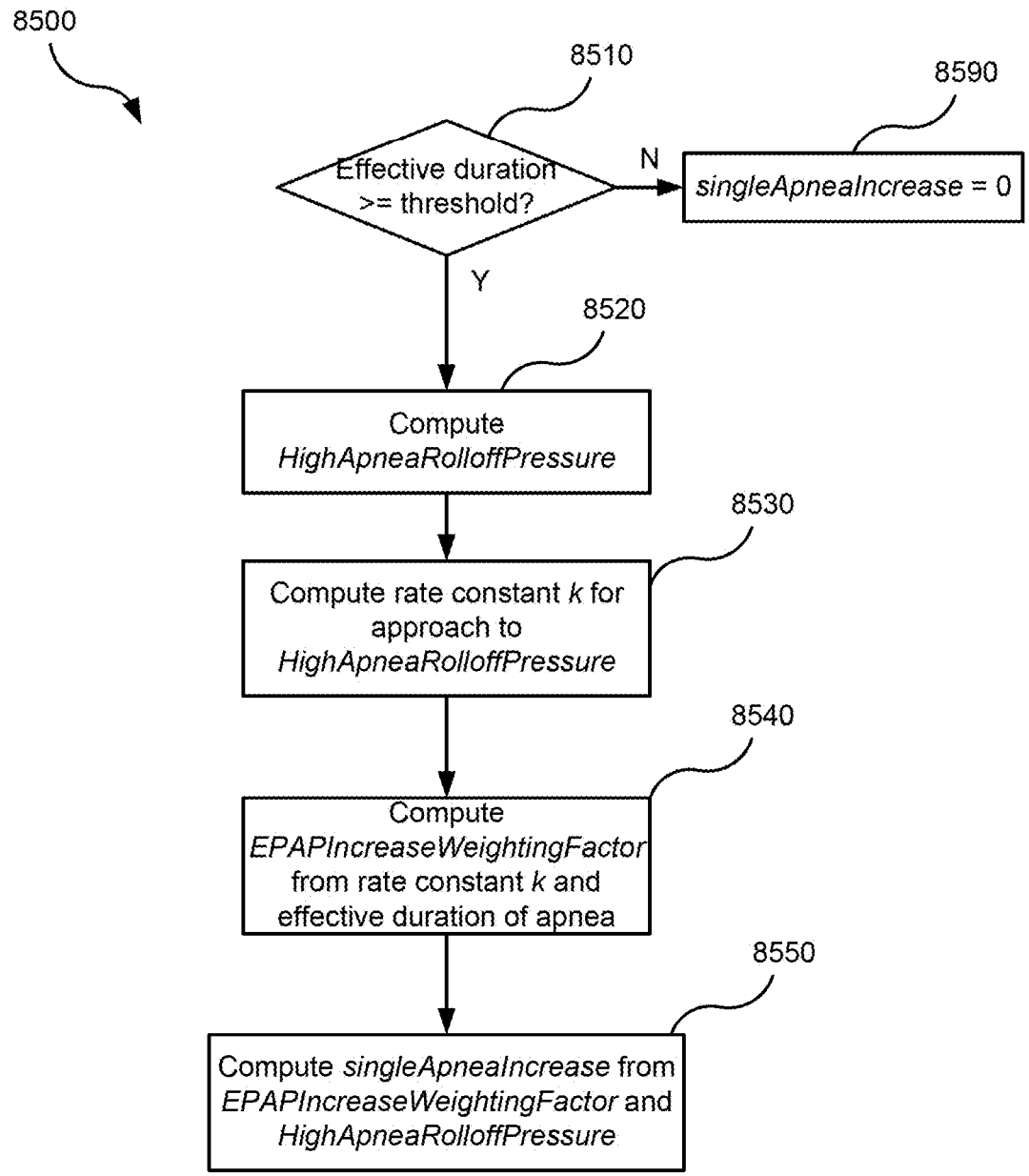

FIG. 8F is a flow chart illustrating a method that may be used to implement the apnea processing step of the method of FIG. 8E.

Figure 8G:
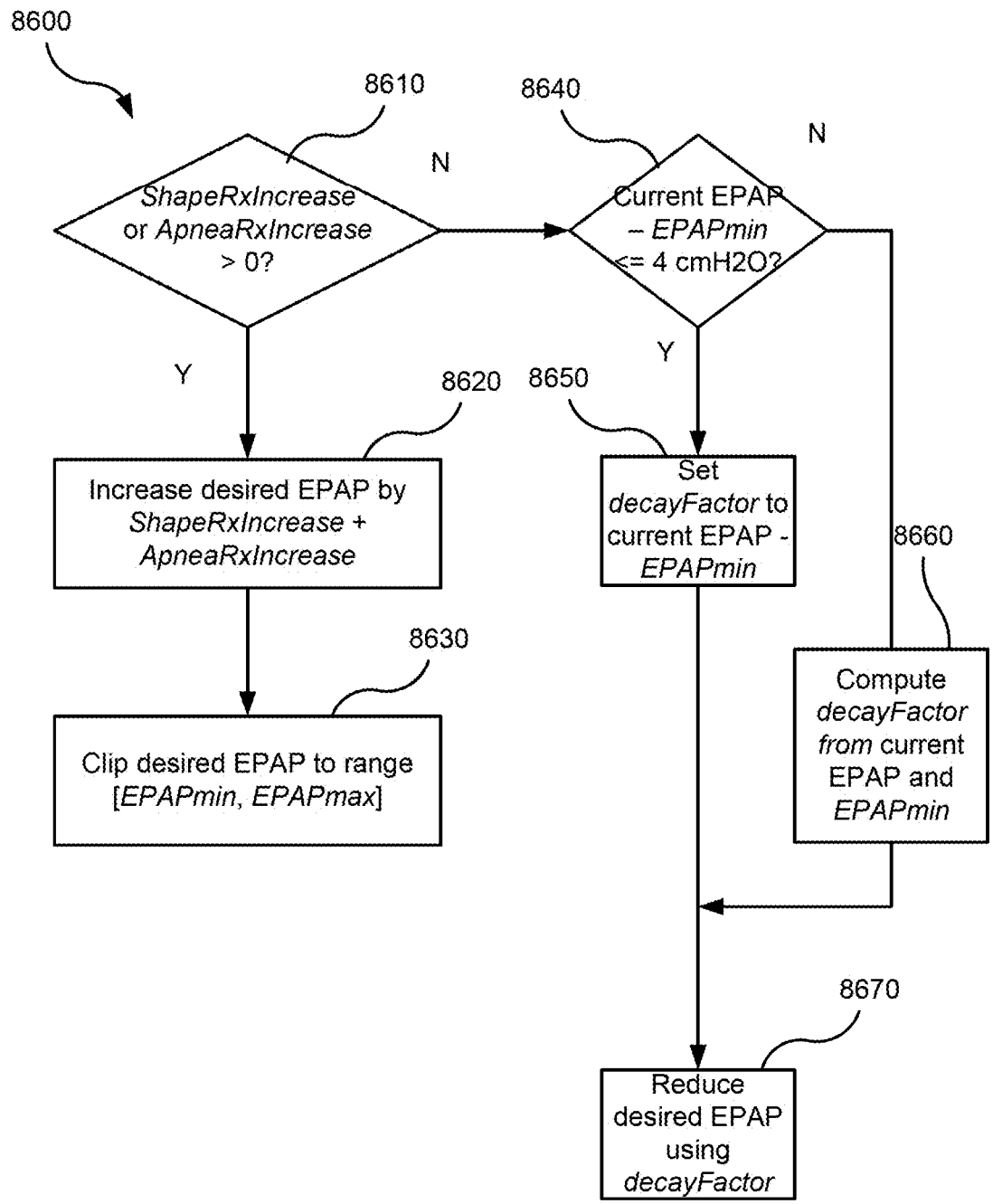

FIG. 8G is a flow chart illustrating a method that may be used to implement a step of the EPAP-auto-titration method of FIG. 8A.

Figure 9A:
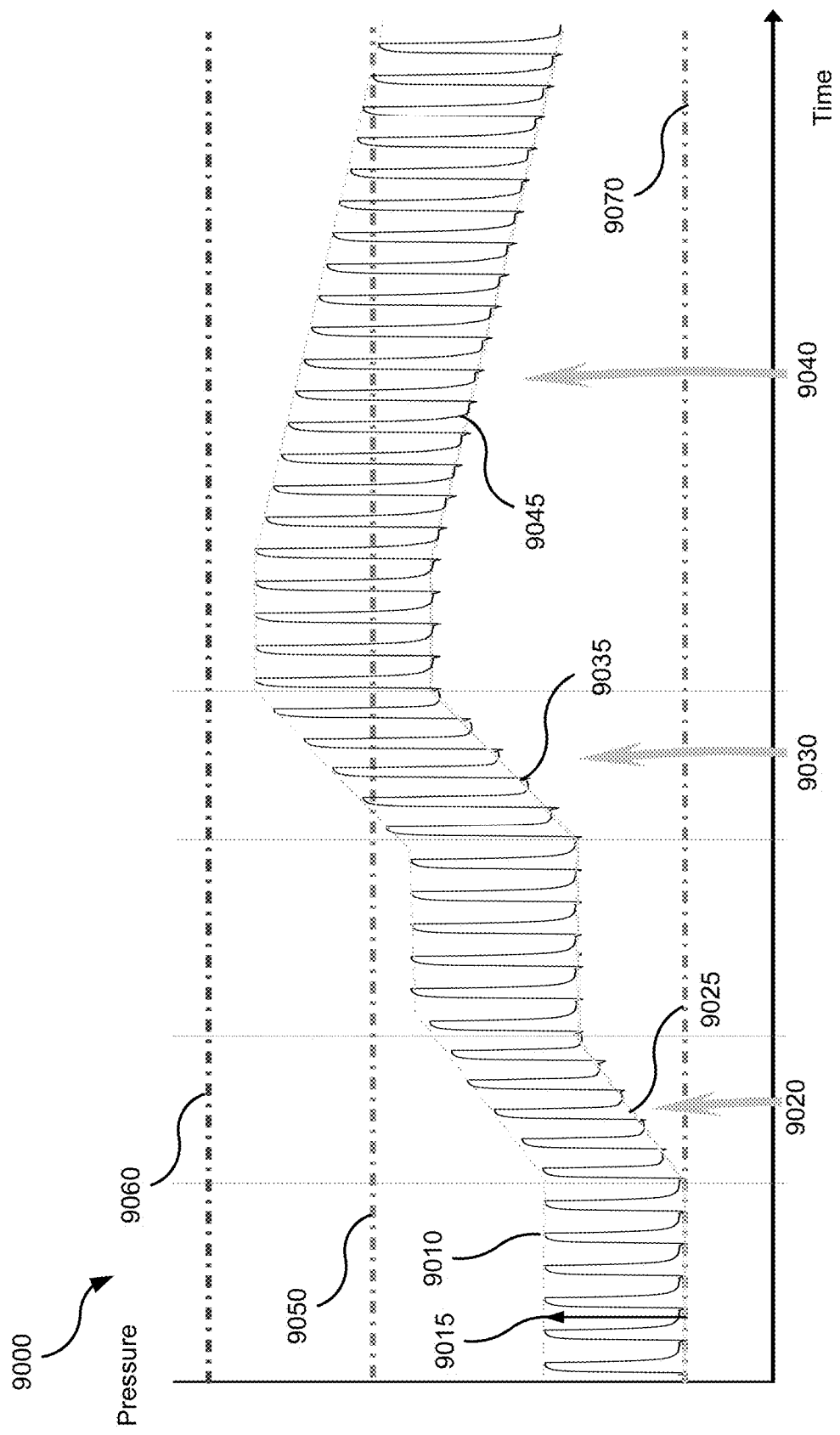

FIG. 9A contains a graph illustrating an example of the behaviour of the EPAP auto-titration method of FIG. 8A in response to episodes of flow limitation.

Figure 9B:
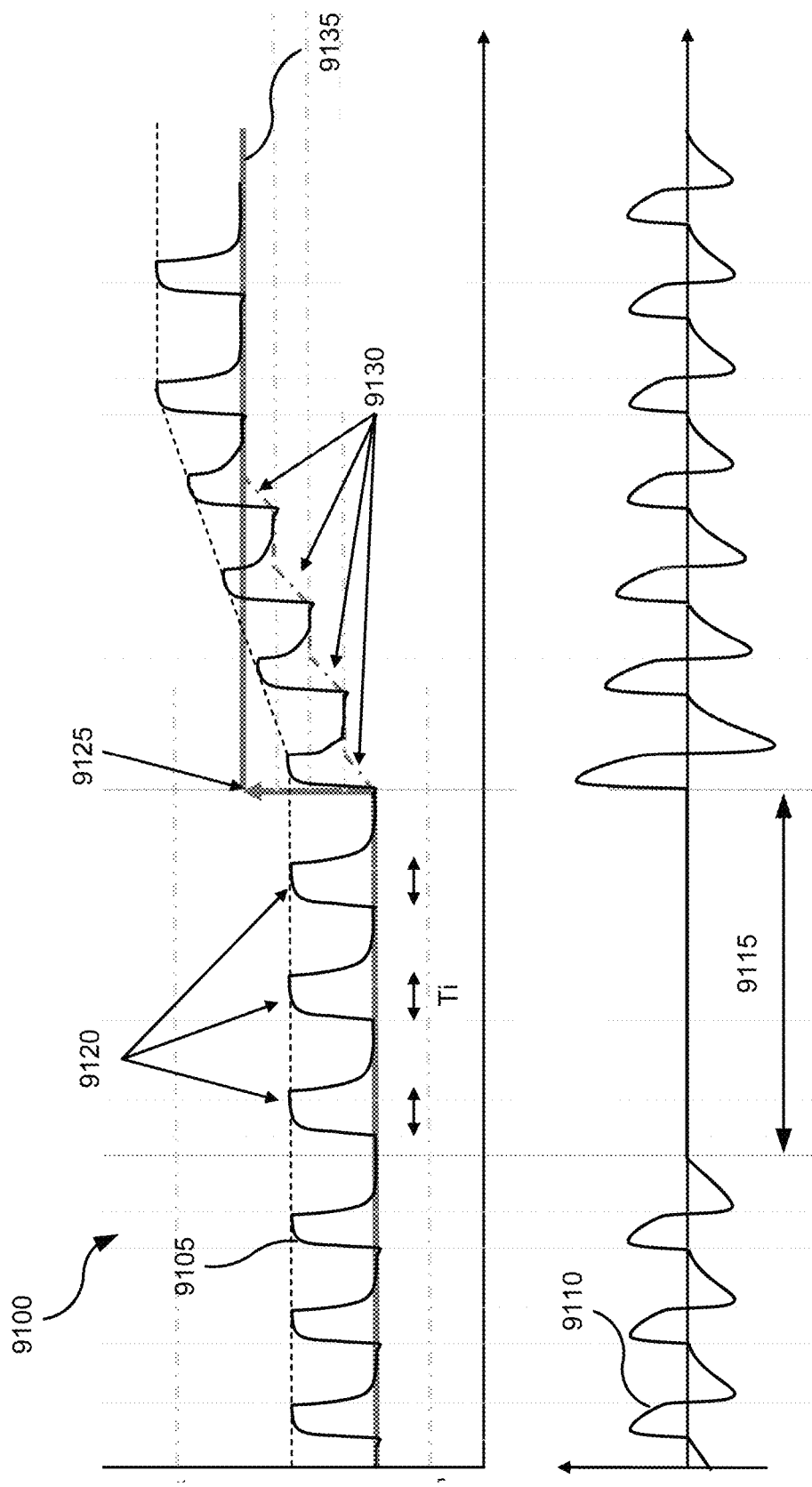

FIG. 9B contains a graph illustrating an example of the behaviour of the EPAP auto-titration method of FIG. 8A in response to a closed apnea.

Figure 9C:
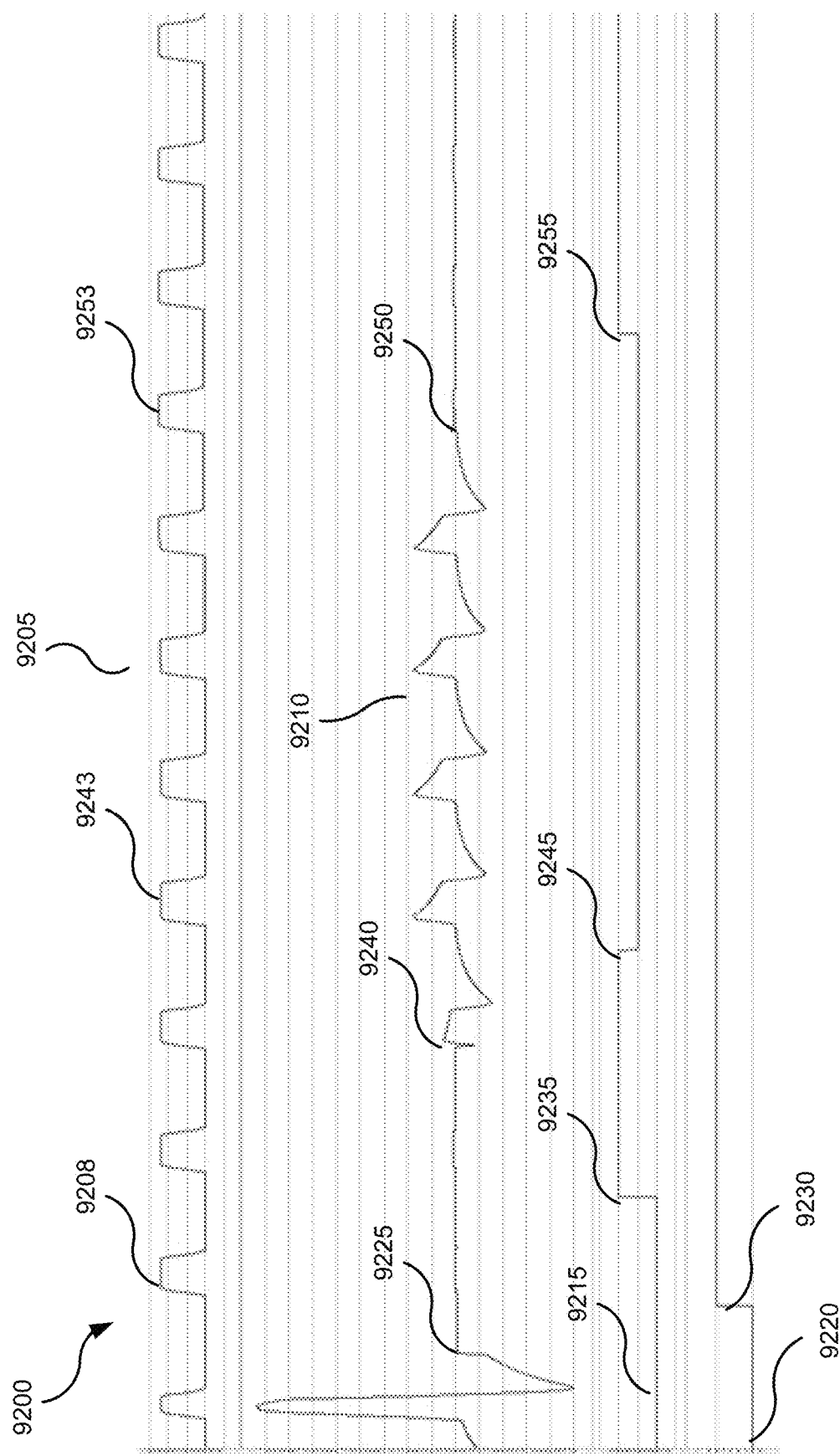

FIG. 9C contains a graph illustrating an example of the behaviour of the airway patency determination algorithm of FIG. 7H in response to a mixed apnea.

Figure 9D:
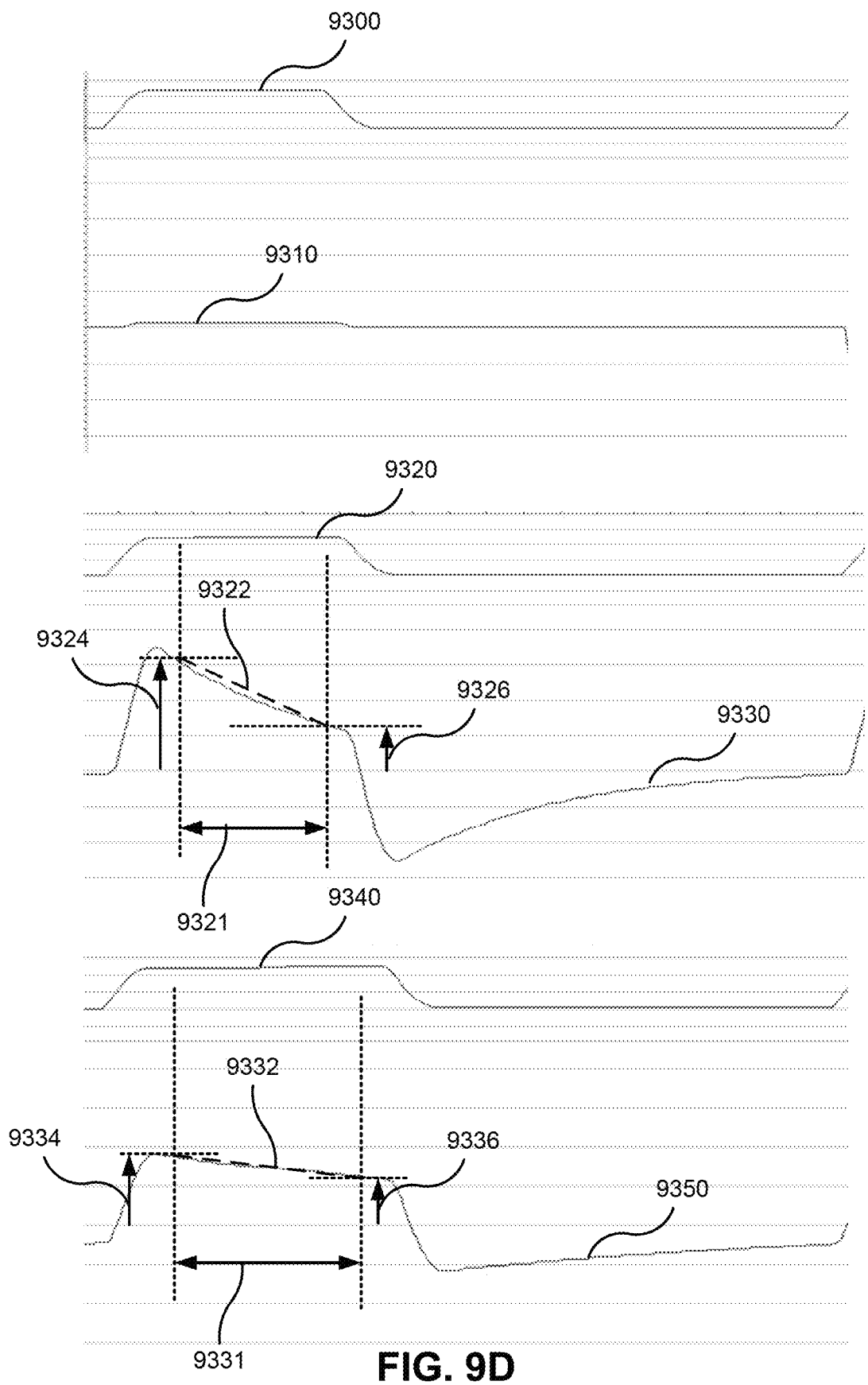

FIG. 9D contains expansions of various sections of the graph of FIG. 9C.

7 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

7.1 Therapy

In one form, the present technology comprises a method for treating a respiratory disorder comprising the step of delivering air at positive pressure to the entrance of the airways of a patient 1000.

In certain examples of the present technology, a supply of air at positive pressure is provided to the nasal passages of the patient via one or both nares.

7.2 Treatment Systems

In one form, the present technology comprises an apparatus or device for treating a respiratory disorder. The apparatus or device may comprise an RPT device 4000 for delivering pressurised air to the patient 1000 via an air circuit 4170 to a patient interface 3000.

7.3 Patient Interface

A non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the delivery of air at positive pressure to the airways.

7.4 RPT Device

An RPT device 4000 in accordance with one aspect of the present technology comprises mechanical and pneumatic components 4100, electrical components 4200 and is configured to execute one or more algorithms 4300. The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of delivering air at positive pressure (e.g., a blower 4142), an outlet muffler 4124 and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

7.4.1 RPT Device Mechanical & Pneumatic Components

An RPT device may comprise one or more of the following components in an integral unit. In an alternative form, one or more of the following components may be located as respective separate units.

7.4.1.1 Air Filter(s)

An RPT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000.

7.4.1.2 Muffler(s)

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000.

7.4.1.3 Pressure Generator

In one form of the present technology, a pressure generator 4140 for delivering a flow, or a supply, of air at positive pressure is a controllable blower 4142. For example the blower 4142 may include a brushless DC motor 4144 with one or more impellers housed in a volute. The blower may be capable of delivering a supply of air, for example at a rate of up to about 120 litres/minute, at a positive pressure in a range from about 4 cm $H_2O$ to about 20 cm $H_2O$, or in other forms up to about 30 cm $H_2O$. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 is under the control of the therapy device controller 4240.

In other forms, a pressure generator 4140 may be a piston-driven pump, a pressure regulator connected to a high pressure source (e.g. compressed air reservoir), or a bellows.

7.4.1.4 Transducer(s)

Transducers may be internal of the RPT device, or external of the RPT device. External transducers may be located for example on or form part of the air circuit, e.g., the patient interface. External transducers may be in the form of non-contact sensors such as a Doppler radar movement sensor that transmit or transfer data to the RPT device.

In one form of the present technology, one or more transducers 4270 are located upstream and/or downstream of the pressure generator 4140. The one or more transducers 4270 may be constructed and arranged to measure properties such as a flow rate, a pressure or a temperature at that point in the pneumatic path.

In one form of the present technology, one or more transducers 4270 may be located proximate to the patient interface 3000.

In one form, a signal from a transducer 4270 may be filtered, such as by low-pass, high-pass or band-pass filtering.

7.4.1.4.1 Flow Rate Sensor

A flow rate sensor 4274 in accordance with the present technology may be based on a differential pressure transducer, for example, an SDP600 Series differential pressure transducer from SENSIRION.

In one form, a signal representing a flow rate such as a total flow rate Qt from the flow rate sensor 4274 is received by the central controller 4230.

7.4.1.4.2 Pressure Sensor

A pressure sensor 4272 in accordance with the present technology is located in fluid communication with the pneumatic path. An example of a suitable pressure transducer is a sensor from the HONEYWELL ASDX series. An alternative suitable pressure transducer is a sensor from the NPA Series from GENERAL ELECTRIC.

In one form, a signal from the pressure sensor 4272 is received by the central controller 4230.

7.4.1.4.3 Motor Speed Transducer

In one form of the present technology a motor speed transducer 4276 is used to determine a rotational velocity of the motor 4144 and/or the blower 4142. A motor speed signal from the motor speed transducer 4276 may be provided to the therapy device controller 4240. The motor speed transducer 4276 may, for example, be a speed sensor, such as a Hall effect sensor.

7.4.1.5 Anti-Spill Back Valve

In one form of the present technology, an anti-spill back valve is located between the humidifier 5000 and the pneumatic block 4020. The anti-spill back valve is constructed and arranged to reduce the risk that water will flow upstream from the humidifier 5000, for example to the motor 4144.

7.4.1.6 Air Circuit

An air circuit 4170 in accordance with an aspect of the present technology is a conduit or a tube constructed and arranged in use to allow a flow of air to travel between two components such as the pneumatic block 4020 and the patient interface 3000.

In particular, the air circuit 4170 may be in fluid connection with the outlet of the pneumatic block and the patient interface. The air circuit may be referred to as an air delivery tube. In some cases there may be separate limbs of the circuit for inspiration and expiration. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller 4230 or a humidifier controller 5250. One example of an air circuit 4170 comprising a heated wire circuit is described in United States Patent Application No. US/2011/0023874, which is incorporated herewithin in its entirety by reference.

7.4.1.7 Oxygen Delivery

In one form of the present technology, supplemental oxygen 4180 is delivered to one or more points in the pneumatic path, such as upstream of the pneumatic block 4020, to the air circuit 4170 and/or to the patient interface 3000.

7.4.2 RPT Device Electrical Components

7.4.2.1 Power Supply

A power supply 4210 may be located internal or external of the external housing 4010 of the RPT device 4000.

In one form of the present technology, power supply 4210 provides electrical power to the RPT device 4000 only. In another form of the present technology, power supply 4210 provides electrical power to both RPT device 4000 and humidifier 5000.

7.4.2.2 Input Devices

In one form of the present technology, an RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form, the input device 4220 may be constructed and arranged to allow a person to select a value and/or a menu option.

7.4.2.3 Central Controller

In one form of the present technology, the central controller 4230 is one or a plurality of processors suitable to control an RPT device 4000.

Suitable processors may include an x86 INTEL processor, a processor based on ARM® Cortex®-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller 4230 is a dedicated electronic circuit.

In one form, the central controller 4230 is an application-specific integrated circuit. In another form, the central controller 4230 comprises discrete electronic components.

The central controller 4230 may be configured to receive input signal(s) from one or more transducers 4270, and one or more input devices 4220.

The central controller 4230 may be configured to provide output signal(s) to one or more of an output device 4290, a therapy device controller 4240, a data communication interface 4280 and humidifier controller 5250.

In some forms of the present technology, the central controller 4230 is configured to implement the one or more methodologies described herein, such as the one or more algorithms 4300 expressed as computer programs stored in a non-transitory computer readable storage medium, such as memory 4260. In some forms of the present technology, the central controller 4230 may be integrated with an RPT device 4000. However, in some forms of the present technology, some methodologies may be performed by a remotely located device. For example, the remotely located device may determine control settings for a ventilator or detect respiratory related events by analysis of stored data such as from any of the sensors described herein.

7.4.2.4 Clock

The RPT device 4000 may include a clock 4232 that is connected to the central controller 4230.

7.4.2.5 Therapy Device Controller

In one form of the present technology, therapy device controller 4240 is a therapy control module 4330 that forms part of the algorithms 4300 executed by the central controller 4230.

In one form of the present technology, therapy device controller 4240 is a dedicated motor control integrated circuit. For example, in one form a MC33035 brushless DC motor controller, manufactured by ONSEMI is used.

7.4.2.6 Protection Circuits

The one or more protection circuits 4250 in accordance with the present technology may comprise an electrical protection circuit, a temperature and/or pressure safety circuit.

7.4.2.7 Memory

In accordance with one form of the present technology the RPT device 4000 includes memory 4260, e.g., non-volatile memory. In some forms, memory 4260 may include battery powered static RAM. In some forms, memory 4260 may include volatile RAM.

Memory 4260 may be located on the PCBA 4202. Memory 4260 may be in the form of EEPROM, or NAND flash.

Additionally or alternatively, RPT device 4000 includes a removable form of memory 4260, for example a memory card made in accordance with the Secure Digital (SD) standard.

In one form of the present technology, the memory 4260 acts as a non-transitory computer readable storage medium on which is stored computer program instructions expressing the one or more methodologies described herein, such as the one or more algorithms 4300. The memory 4260 may also act as a volatile or non-volatile storage medium for data acquired, collected, used or generated as one or more of the methodologies described herein are executed as instructions by one or more processors.

7.4.2.8 Data Communication Systems

In one form of the present technology, a data communication interface 4280 is provided, and is connected to the central controller 4230. Data communication interface 4280 may be connectable to a remote external communication network 4282 and/or a local external communication network 4284. The remote external communication network 4282 may be connectable to a remote external device 4286. The local external communication network 4284 may be connectable to a local external device 4288.

In one form, data communication interface 4280 is part of the central controller 4230. In another form, data communication interface 4280 is separate from the central controller 4230, and may comprise an integrated circuit or a processor.

In one form, remote external communication network 4282 is the Internet. The data communication interface 4280 may use wired communication (e.g. via Ethernet, or optical fibre) or a wireless protocol (e.g. CDMA, GSM, LTE) to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such a remote external device 4286 may be accessible to an appropriately authorised person such as a clinician.

The local external device 4288 may be a personal computer, mobile phone, tablet or remote control.

7.4.2.9 Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

7.4.2.9.1 Display Driver

A display driver 4292 receives as an input the characters, symbols, or images intended for display on the display 4294, and converts them to commands that cause the display 4294 to display those characters, symbols, or images.

7.4.2.9.2 Display

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

7.4.3 RPT Device Algorithms

7.4.3.1 Pre-Processing Module

A pre-processing module 4310 in accordance with one form of the present technology receives as an input a signal from a transducer 4270, for example a flow rate sensor 4274 or pressure sensor 4272, and performs one or more process steps to calculate one or more output values that will be used as an input to another module, for example a therapy engine module 4320.

In one form of the present technology, the output values include the interface or mask pressure Pm, the respiratory flow rate Qr, and the leak flow rate Ql.

In various forms of the present technology, the pre-processing module 4310 comprises one or more of the following algorithms: pressure compensation 4312, vent flow rate estimation 4314, leak flow rate estimation 4316, and respiratory flow rate estimation 4318.

7.4.3.1.1 Pressure Compensation

In one form of the present technology, a pressure compensation algorithm 4312 receives as an input a signal indicative of the pressure in the pneumatic path proximal to an outlet of the pneumatic block. The pressure compensation algorithm 4312 estimates the pressure drop through the air circuit 4170 and provides as an output an estimated pressure, Pm, in the patient interface 3000.

7.4.3.1.2 Vent Flow Rate Estimation

In one form of the present technology, a vent flow rate estimation algorithm 4314 receives as an input an estimated pressure, Pm, in the patient interface 3000 and estimates a vent flow rate of air, Qv, from a vent 3400 in a patient interface 3000.

7.4.3.1.3 Leakflow Rate Estimation

In one form of the present technology, a leak flow rate estimation algorithm 4316 receives as an input a total flow rate, Qt, and a vent flow rate Qv, and provides as an output an estimate Ql of the leak flow rate. In one form, the leak flow rate estimation algorithm 4316 estimates the leak flow rate Ql by calculating an average of the difference between total flow rate Qt and vent flow rate Qv over a period sufficiently long to include several breathing cycles, e.g. about 10 seconds.

In one form, the leak flow rate estimation algorithm 4316 receives as an input a total flow rate Qt, a vent flow rate Qv, and an estimated pressure, Pm, in the patient interface 3000, and provides as an output a leak flow rate Ql, by calculating a leak conductance, and determining a leak flow rate Ql to be a function of leak conductance and pressure, Pm. Leak conductance is calculated as the quotient of low pass filtered non-vent flow rate equal to the difference between total flow rate Qt and vent flow rate Qv, and low pass filtered square root of pressure Pm, where the low pass filter time constant has a value sufficiently long to include several breathing cycles, e.g. about 10 seconds. The leak flow rate Ql may be estimated as the product of leak conductance and a function of pressure, Pm.

7.4.3.1.4 Respiratory Flow Rate Estimation

In one form of the present technology, a respiratory flow rate estimation algorithm 4318 receives as an input a total flow rate, Qt, a vent flow rate, Qv, and a leak flow rate, Ql, and estimates a respiratory flow rate of air, Qr, to the patient, by subtracting the vent flow rate Qv and the estimated leak flow rate Ql from the total flow rate Qt.

7.4.3.2 Therapy Engine Module

In one form of the present technology, a therapy engine module 4320 receives as inputs one or more of a pressure, Pm, in a patient interface 3000, and a respiratory flow rate of air to a patient, Qr, and provides as an output one or more therapy parameters.

In one form of the present technology, a therapy parameter is a treatment pressure Pt.

In various forms, the therapy engine module 4320 comprises one or more of the following algorithms: phase determination 4321, waveform determination 4322, ventilation determination 4323, inspiratory flow limitation detection 4324, apnea detection 4325, inspiratory M-shape detection 4326, airway patency determination 4327, typical recent ventilation determination 4328, and therapy parameter determination 4329.

7.4.3.2.1 Phase Determination

In one form of the present technology, a phase determination algorithm 4321 receives as an input a signal indicative of respiratory flow rate, Qr, and provides as an output a phase $\Phi$ of a current breathing cycle of a patient 1000.

In some forms, known as discrete phase determination, the phase output $\Phi$ is a discrete variable. One implementation of discrete phase determination provides a bi-valued phase output $\Phi$ with values of either inspiration or expiration, for example represented as values of 0 and 0.5 revolutions respectively, upon detecting the start of spontaneous inspiration and expiration respectively. RPT devices 4000 that "trigger" and "cycle" effectively perform discrete phase determination, since the trigger and cycle instants are the instants at which the phase changes from expiration to inspiration and from inspiration to expiration, respectively. In one implementation of bi-valued phase determination, the phase output $\Phi$ is determined to have a discrete value of 0 (indicative of inspiration) when the respiratory flow rate Qr exceeds a "trigger threshold" (thereby triggering the RPT device 4000 to deliver a "spontaneous breath"), and a discrete value of 0.5 revolutions (indicative of expiration) when the respiratory flow rate Qr falls below a "cycle threshold" (thereby "spontaneously cycling" the RPT device 4000). In some such implementations, the trigger and cycle thresholds may vary with time during a breath according to respective trigger and cycle threshold functions. Such functions are described in the Patent Cooperation Treaty patent application number PCT/AU2005/000895, published as WO 2006/000017, to ResMed Limited, the entire contents of which are herein incorporated by reference.

In some such implementations, cycling may be prevented during a "refractory period" (denoted as Timin) after the last trigger instant, and, absent spontaneous cycling, must occur within an interval (denoted as Timax) after the last trigger instant. The values of Timin and Timax are settings of the RPT device 4000, and may be set for example by hard-coding during configuration of the RPT device 4000 or by manual entry through the input device 4220.

In other forms, known as continuous phase determination, the phase output Φ is a continuous variable, for example varying from 0 to 1 revolutions, or 0 to 2π radians. RPT devices 4000 that perform continuous phase determination may trigger and cycle when the continuous phase reaches 0 and 0.5 revolutions, respectively. In one implementation of continuous phase determination, the inspiratory time Ti and the expiratory time Te are first estimated from the respiratory flow rate Qr. The phase Φ is then determined as the half the proportion of the inspiratory time Ti that has elapsed since the previous trigger instant, or 0.5 revolutions plus half the proportion of the expiratory time Te that has elapsed since the previous cycle instant (whichever was more recent).

In some implementations, suitable for ventilation therapy (described below), the phase determination algorithm 4321 is configured to trigger even when the respiratory flow rate Qr is insignificant, such as during an apnea. As a result, the RPT device 4000 delivers "backup breaths" in the absence of spontaneous respiratory effort from the patient 1000. For such forms, known as spontaneous/timed (ST) modes, the phase determination algorithm 4321 may make use of a "backup rate" Rb. The backup rate Rb is a setting of the RPT device 4000, and may be set for example by hard-coding during configuration of the RPT device 4000 or by manual entry through the input device 4220.

A phase determination algorithm 4321 (either discrete, or continuous) may implement ST modes using the backup rate Rb in a manner known as timed backup. Timed backup may be implemented as follows: the phase determination algorithm 4321 attempts to detect the start of inspiration due to spontaneous respiratory effort, for example by comparing the respiratory flow rate Qr with a trigger threshold as described above. If the start of spontaneous inspiration is not detected within an interval after the last trigger instant whose duration is equal to the reciprocal or inverse of the backup rate Rb (an interval referred to as the backup timing threshold, Tbackup), the phase determination algorithm 4321 sets the phase output Φ to value of 0, thereby triggering the RPT device 4000 to deliver a backup breath. The phase determination algorithm 4321 then attempts to detect the start of spontaneous expiration, for example by comparing the respiratory flow rate Qr with a cycle threshold as described above. The cycle threshold for backup breaths may be different from the cycle threshold for spontaneous breaths. As with spontaneous breaths, spontaneous cycling during backup breaths may be prevented during a "refractory period" of duration Timin after the last trigger instant.

As with spontaneous breaths, if during a backup breath the start of spontaneous expiration is not detected within Timax seconds after the last trigger instant, the phase determination algorithm 4321 sets the phase output Φ to value of 0.5, thereby cycling the RPT device 4000. The phase determination algorithm 4321 then attempts to detect the start of spontaneous inspiration by comparing the respiratory flow rate Qr with a trigger threshold as described above.

7.4.3.2.2 Waveform Determination

In one form of the present technology, the waveform determination algorithm 4322 provides an approximately constant treatment pressure throughout a respiratory cycle of a patient.

In other forms of the present technology, the waveform determination algorithm 4322 controls the pressure generator 4140 to provide a treatment pressure Pt that varies throughout a respiratory cycle of a patient according to a waveform template.

In one form of the present technology, a waveform determination algorithm 4322 provides a waveform template Π(Φ) with values in the range [0, 1] on the domain of phase values Φ provided by the phase determination algorithm 4321 to be used by the waveform determination algorithm 4322.

In one form, suitable for either discrete or continuously-valued phase, the waveform template Π(Φ) is a square-wave template, having a value of 1 for values of phase up to and including 0.5 revolutions, and a value of 0 for values of phase above 0.5 revolutions. In one form, suitable for continuously-valued phase, the waveform template Π(Φ) comprises two smoothly curved portions, namely a smoothly curved (e.g. raised cosine) rise from 0 to 1 for values of phase up to 0.5 revolutions, and a smoothly curved (e.g. exponential) decay from 1 to 0 for values of phase above 0.5 revolutions.

In some forms of the present technology, the waveform determination algorithm 4322 selects a waveform template Π(Φ) from a library of waveform templates, dependent on a setting of the RPT device 4000. Each waveform template Π(Φ) in the library may be provided as a lookup table of values H against phase values Φ. In other forms, the waveform determination algorithm 4322 computes a waveform template Π(Φ) "on the fly" using a predetermined functional form, possibly parametrised by one or more parameters (e.g. a rise time and a fall time). The parameters of the functional form may be predetermined or dependent on a current state of the patient 1000.

In some forms of the present technology, suitable for discrete bi-valued phase of either inspiration (Φ=0 revolutions) or expiration (Φ=0.5 revolutions), the waveform determination algorithm 4322 computes a waveform template Π "on the fly" as a function of both discrete phase Φ and time t measured since the most recent trigger instant. In one such form, the waveform determination algorithm 4322 computes the waveform template Π(Φ, t) in two portions (inspiratory and expiratory) as follows:

$$\prod(\Phi, t) = \begin{cases} \prod_i(t), & \Phi = 0 \\ \prod_e(t - Ti), & \Phi = 0.5 \end{cases}$$

where $\Pi_i(t)$ and $\Pi_e(t)$ are inspiratory and expiratory portions of the waveform template Π(Φ, t).

In one such form, the inspiratory portion $\Pi_i(t)$ of the waveform template is a smooth rise from 0 to 1 in two continuous sections:
- a linear rise up to ⅔ for the first half of a parameter known as the "time scale";
- a parabolic rise up to 1 for the second half of the time scale.

The "rise time" of such an inspiratory portion $\Pi_i(t)$ may be defined as the time taken for $\Pi_i(t)$ to rise to a value of 0.875.

The expiratory portion $\Pi_e(t)$ of the waveform template is a smooth fall from 1 to 0 in two continuous parabolic sections, with an inflection point between 25% and 50% of the time scale. The "fall time" of such an expiratory portion $\Pi_e(t)$ may be defined as the time taken for $\Pi_e(t)$ to fall to a value of 0.125.

7.4.3.2.3 Ventilation Determination

In one form of the present technology, a ventilation determination algorithm 4323 receives an input a respiratory flow rate Qr, and determines a measure Vent indicative of current patient ventilation.

In some implementations, the ventilation determination algorithm 4323 computes Vent as an "instantaneous ventilation" Vint, which is half the absolute value of the respiratory flow rate signal Qr.

In some implementations, the ventilation determination algorithm 4323 computes Vent as a "very fast ventilation" VveryFast by filtering the instantaneous ventilation Vint by a low-pass filter such as a fourth order Bessel low-pass filter with a corner frequency of approximately 0.10 Hz. This is equivalent to a time constant of approximately ten seconds.

In some implementations, the ventilation determination algorithm 4323 computes a Vent as a "fast ventilation" Vfast by filtering the instantaneous ventilation Vint by a low-pass filter such as a fourth order Bessel low-pass filter with a corner frequency of approximately 0.05 Hz. This is equivalent to a time constant of approximately twenty seconds.

In some implementations of the present technology, the ventilation determination algorithm 4323 determines Vent as a measure of alveolar ventilation. Alveolar ventilation is a measure of how much air is actually reaching the gas exchange surfaces of the respiratory system in a given time. Because the respiratory system of the patient includes a significant "anatomical dead space", i.e. volume in which gas exchange does not take place, the alveolar ventilation is less than the "gross" ventilation values that the above calculations that operate directly on the respiratory flow rate Qr will produce, but is a more accurate measure of the respiratory performance of a patient.

In such implementations, the ventilation determination algorithm 4323 may determine the instantaneous alveolar ventilation to be either zero or half the absolute value of the respiratory flow rate Qr. The conditions under which the instantaneous alveolar ventilation is zero are:
- When the respiratory flow rate changes from non-negative to negative, or
- When the respiratory flow rate changes from negative to non-negative, and
- After the respiratory flow rate has changed sign, for the period during which the absolute value of the integral of the respiratory flow rate Qr is less than the patient's anatomical dead space volume.

The patient's anatomical dead space volume may be a setting of the RPT device 4000, set for example by hard-coding during configuration of the RPT device 4000 or by manual entry through the input device 4220.

In some such implementations, the ventilation determination algorithm 4323 may compute Vent as a "very fast alveolar ventilation" and/or a "fast alveolar ventilation" by low-pass filtering the instantaneous alveolar ventilation using the respective low-pass filters described above.

In what follows the word "alveolar" is omitted but it may be assumed to be present in some implementations of the therapy engine module 4320. That is, mentions of "ventilation" and "tidal volume" in the subsequent description may be taken to apply to alveolar ventilation and alveolar tidal volume as well as "gross" ventilation and tidal volume.

7.4.3.2.4 Inspiratory Flow Limitation Determination

In one form of the present technology, the therapy engine module 4320 executes one or more algorithms to determine the extent of flow limitation, sometimes referred to as partial upper airway obstruction, in the inspiratory portion of the respiratory flow rate waveform (herein sometimes shortened to the "inspiratory waveform"). In one form, the flow limitation determination algorithm 4324 receives as an input a respiratory flow rate signal Qr and provides as an output a measure of the extent to which each inspiratory waveform exhibits flow limitation.

A normal inspiratory waveform is rounded, close to sinusoidal in shape (see FIG. 6A). With sufficient upper airway muscle tone (or EPAP), the airway acts essentially as a rigid tube, where flow increases in response to increased breathing effort (or external ventilatory assistance). In some situations (e.g. sleep, sedation) the upper airway may be collapsible, such as in response to sub-atmospheric pressure within it from breathing effort, or even from applied ventilation. This can lead to either full obstruction (apneas), or a phenomenon known as 'flow limitation'. The term 'flow limitation' includes behaviour where increased breathing effort simply induces increased narrowing of the airway, such that inspiratory flow becomes limited at a constant value, independent of effort ("Starling resistor behaviour"). Therefore the inspiratory flow rate curve exhibits a flattened shape (see FIG. 6B).

In reality, upper airway behaviour is even more complicated, and there is a wide variety of flow shapes that are indicative of upper airway-related inspiratory flow limitation, and an even wider variety in the presence of external ventilatory assistance (see FIGS. 6C to 6F). For this reason, the flow limitation determination algorithm 4324 may respond to one or more of the following kinds of inspiratory flow limitation: "classical flatness" (see FIG. 6B), "chairness" (see FIG. 6C), and "reverse chairness" (see FIG. 6D). ("M-shape" (see FIGS. 6E and 6F) is dealt with separately, using M-shape detection algorithm 4326.)

FIG. 7A is a flow chart illustrating a method 7000 that may be used to compute a measure of flow limitation of the inspiratory portion of the respiratory flow rate waveform as part of the inspiratory flow limitation determination algorithm 4324 in one form of the present technology.

The method 7000 starts at step 7010, which computes a number of "central part features" CF1 to CF8 based on the central part of the inspiratory waveform, including the central slope, the central deviation, the central concavity, and the extents to which the waveform has a large initial section and a large final section (before and after the central part, approximately). Step 7010 is described in detail below with reference to FIG. 7B.

The next step 7020 combines the central part features CF1 to CF8 computed at step 7010 using fuzzy logic to compute a number of flow limitation fuzzy truth variables FL1 to FL6 indicating degrees of similarity between the inspiratory waveform and respective stereotypical flow-limited (partially obstructed) inspiratory waveforms. These stereotypes may include: moderately flat, possibly concave; mildly negative slope, indicating high inspiratory resistance; very flat; flat or M-shaped with large initial peak; flattish, possibly with a somewhat negative slope, with a peak in the post-central part; and concave and flattish. Step 7020 is described in detail below with reference to FIG. 7C.

The method 7000 then at step 7030 computes a fuzzy truth variable fuzzyLateFlatness that indicates a degree of "chairness" of the inspiratory waveform, i.e. a combination of early peak, late linearity, and moderate late slope (as illustrated in FIG. 6C). Step 7030 is described in detail below with reference to FIG. 7E.

Finally at step 7040, the computed flow limitation fuzzy truth variables FL1 to FL6 (from step 7020) and the fuzzy truth variable fuzzyLateFlatness (from step 7030) are all combined using a "fuzzy OR" operation to compute a fuzzy truth variable flowLimitation indicating the extent of inspiratory flow limitation. The fuzzy "OR" takes the maximum of the fuzzy truth variables, so the fuzzy truth variable flowLimitation indicates the degree of similarity to the one of the stereotypical flow-limited inspiratory waveforms to which the inspiratory waveform is most similar.

By basing the detection of flow limitation primarily on features extracted from the central part of the inspiratory waveform, the method 7000 is more robust to mismodelled leak than other methods of detecting inspiratory flow limitation. This is because mismodelled leak tends to induce a (usually, though not exclusively) positive offset to the respiratory flow rate signal Qr that is a function of the mask pressure Pm, which tends to be generally constant during the central and later parts of the inspiratory waveform (e.g. once the rise time has passed). The offset to the respiratory flow rate signal Qr induced by mismodelled leak therefore also tends to be constant during the central and later parts of the inspiratory waveform.

FIG. 7B is a flow chart illustrating a method 7100 that may be used to implement step 7010 of the method 7000 in one form of the present technology. The method 7100 receives as parameters a "low fraction" and a "high fraction" of the duration of the inspiratory waveform. The "central part" of the inspiratory waveform used by the method 7100 extends from the low fraction multiplied by the duration of the inspiratory waveform to the high fraction multiplied by the duration of the inspiratory waveform. In one implementation of step 7010, the "low fraction" passed to the method 7100 is 0.3, and the "high fraction" is 0.85.

The method 7100 starts at step 7110, which constructs a notional "ramp" over the part of the inspiratory waveform before the central part, i.e. the "pre-central" part. The ramp extends from the start point of the inspiratory waveform to the start point of the central part.

Step 7120 then computes the amount of respiratory flow above the ramp by summing the difference between the inspiratory waveform and the ramp over the pre-central part. This amount is referred to as flowAboveRampToStartOfCentralPart.

The next step 7130 computes the first central part feature (CF1), propnAboveRampToStartOfCentralPart, by dividing flowAboveRampToStartOfCentralPart by the sum of all the inspiratory waveform values. A markedly positive value of propnAboveRampToStartOfCentralPart is generally associated with an early peak of the inspiratory flow rate waveform. A negative value indicates a very gentle rise of flow to the central part, and is unlikely to be associated with flow limitation or high inspiratory resistance.

Step 7140 follows, at which the method 7100 computes the second central part feature (CF2), centralSlope, over the central part. CentralSlope, which represents the slope of a linear approximation to the normalised central part of the inspiratory waveform, may be computed by linear regression of the normalised central part. The normalising factor is the maximum of the mean of the complete inspiratory waveform, and the minimum normalising flow, which is defined in one implementation to be 24 litres/minute.

Step 7150 then computes centralFlowsMean, the mean of the normalised central part of the inspiratory waveform. Step 7150 then multiplies centralFlowsMean by the duration of the central part to obtain the third central part feature (CF3), centralPartDurationByFlowsMeanProduct.

The method 7100 proceeds to step 7160, which computes the fourth central part feature (CF4), postCentralActualAbovePredicted, a measure of how much the flow rate in the part of the inspiratory waveform after the central part (the post-central part) is above the linear approximation to the central part. Step 7160 computes postCentralActualAbovePredicted by summing the difference between the normalised inspiratory waveform values and the linear approximation extended over the post-central part, and dividing the sum by the duration of the post-central part and the value of centralFlowsMean. (In one implementation, if centralFlowsMean is not positive, postCentralActualAbovePredicted is set to zero.) A negative value of postCentralActualAbovePredicted generally indicates normal breathing, because in partial upper airway obstruction the flow rate is generally greater than or equal to the projection of the central part forward in time, whereas in normal breathing the flow rate after the central part almost always decreases more rapidly than in the central part. Put another way, in normal breathing the flow rate in the central part and the post-central part taken together is generally convex, whereas in flow-limited breathing, the flow rate in the central part taken together with most of the post-central part is generally not convex.

The next step 7170 computes the fifth central part feature (CF5), centralDeviation, a measure of the variation of the actual inspiratory waveform values from the linear approximation thereto over the central part. In one implementation of step 7170, centralDeviation is computed as the square root of the sum of the squares of the difference between the normalised flow rate and the linear approximation thereto (computed from centralFlowsMean and centralSlope), over the central part. A markedly positive value of centralDeviation indicates significant non-linearity in the central part.

Finally, at step 7180 the method 7100 computes the sixth central part feature (CF6), centralConcavity, a measure of the concavity of the central part. A positive value of centralConcavity indicates the central part is roughly concave upwards. In one implementation of step 7180, centralConcavity is computed as a measure of similarity between the normalised, mean-subtracted inspiratory waveform and a V-shaped function over the central part. In one implementation of step 7180, the measure of similarity is computed as the sum over the central part of the products of the normalised, mean-subtracted inspiratory waveform and the V-shaped function, divided by the autocorrelation of the V-shaped function. Other measures of concavity may also be used at step 7180 to compute centralConcavity, e.g. the curvature of a parabolic approximation to the central part. Another measure of concavity is the inner product of the central part with the second derivative of a Gaussian function with a suitable scaling factor, over a suitable range, e.g. that corresponding to +/−2 standard deviations. This may alternatively be implemented by taking the second derivative of the flow at the centre of the low-pass filtered central part, where the low-pass filtering has been performed by convolution with a Gaussian function, possibly with appropriate windowing. Other low-pass filters may be used, followed by a standard numerical method for calculating the second derivative on the filtered waveform.

To compute the seventh and eighth central part features, step 7010 may repeat the method 7100 with a different definition of the central part, i.e. different values of the parameters "low fraction" and "high fraction". In one such implementation, the "low fraction" for the second iteration of the method 7100 is 0.2, and the "high fraction" is 0.8, both of which are lower than the corresponding fractions defining the central part over which the central part features CF1 to CF6 were computed, and which therefore define an earlier portion of the inspiratory waveform. The seventh central part feature (CF7), named ConcaveAndFlattishCentralSlope, is the value of centralSlope returned by step 7140 of the second iteration of the method 7100. The value of ConcaveAndFlattishCentralSlope is subtly different from the value of centralSlope (CF2) from being computed over an earlier portion of the inspiratory waveform.

The eighth central part feature (CF8), named ConcaveAndFlattishCentralConcavity, is the value of centralConcavity returned by step 7180 of the second iteration of the method 7100. The value of ConcaveAndFlattishCentralConcavity is subtly different from the value of centralConcavity (CF6) from being computed over an earlier portion of the inspiratory waveform.

By basing the computation of central part features CF1 to CF8 generally on normalised quantities, the method 7100 makes itself more robust to offsets in the inspiratory waveform induced by mismodelled leak.

FIG. 7C is a flow chart illustrating a method 7200 that may be used to implement step 7020 of the method 7000 in one form of the present technology. As mentioned above, step 7020 combines the central part features CF1 to CF8 computed at step 7010, such as by using fuzzy logic, to compute a number of flow limitation fuzzy truth variables FL1 to FL6 indicating the similarity of the inspiratory waveform to respective stereotypical flow-limited inspiratory waveforms.

Each step 7210 to 7260 operates independently on some subset of the eight central part features CF1 to CF8 to compute one of six flow limitation fuzzy truth variables FL1 to FL6. For this reason, steps 7210 to 7260 may be carried out in parallel or any convenient order.

Step 7210 computes the flow limitation fuzzy truth variable FL1, named flattishMaybeConcave, as the fuzzy AND of three fuzzy truth variables centralSlopeFlattishMaybeConcave, centralDeviationFlattishMaybeConcave, and centralConcavityFlattishMaybeConcave, obtained from the central part features centralSlope (CF2), centralDeviation (CF5) and centralConcavity (CF6) respectively. The three fuzzy truth variables that contribute to flattishMaybeConcave indicate respectively that the central part of the inspiratory waveform is moderately flat (approximately horizontal and reasonably linear) and slightly concave upwards. In one implementation, step 7210 computes centralSlopeFlattishMaybeConcave, centralDeviationFlattishMaybeConcave, and centralConcavityFlattishMaybeConcave as follows:

centralSlopeFlattishMaybeConcave=
      FuzzyMember(
        centralSlope, −0.2, False, −0.1, True, 0.1, True, 0.2, False)
    centralDeviationFlattishMaybeConcave=FuzzyMember(
      centralDeviation, 0.05, True, 0.1, False)
    centralConcavityFlattishMaybeConcave=FuzzyMember(
      centralConcavity, −0.2, False, 0.0, True)

Step 7220 computes the flow limitation fuzzy truth variable FL2, named mildNegSlopeHighInspResistance, from the six central part features CF1 to CF6. The flow limitation fuzzy truth variable mildNegSlopeHighInspResistance indicates that the inspiratory waveform has mildly negative slope in the central part indicating high inspiratory resistance.

FIG. 7D is a flow chart illustrating a method 7300 that may be used to implement step 7220 of the method 7200 in one form of the present technology.

The method 7300 starts at step 7310, which checks whether the central part feature centralPartDurationBy-FlowsMeanProduct (CF3) is greater than 0, or the central part feature centralSlope (CF2) is between [−0.6, −0.1]. If not ("N"), the method 7300 proceeds to step 7320, which sets mildNegSlopeHighInspResistance to False, because either the central slope is not mildly negative or the central part is too small to be useful.

Otherwise ("Y"), the method 7300 commences computing four fuzzy truth variables which will be combined using a fuzzy AND operation to yield mildNegSlopeHighInspResistance.

This computation starts at step 7330, which computes an intermediate fuzzy truth variable pairIsHigh from the central part feature propnAboveRampToStartOfCentralPart (CF1) such that pairIsHigh goes True as the pre-central part becomes "peakier". In one implementation, step 7330 computes pairIsHigh as follows:

pairIsHigh=FuzzyMember(
      propnAboveRampToStartOfCentralPart,
        0.08, False, 0.12, True)

Step 7340 then computes a slope-dependent deviation threshold from pairIsHigh and centralSlope. In one implementation, step 7340 computes slopeDependentDeviationThreshold as follows:

slopeDependentDeviationThreshold=
    pairIsHigh*0.08+(1−pairIsHigh)*(0.04+(centralSlope+0.5)*0.1)

At the next step 7350, the method 7300 computes the first of the four fuzzy truth variables that contribute to mildNegSlopeHighInspResistance, namely centralDeviationLow, using the central part feature centralDeviation (CF5) minus the slope-dependent deviation threshold just computed. The value of centralDeviationLow becomes False as this difference increases. In one implementation, step 7350 computes centralDeviationLow as follows:

centralDeviationLow = FuzzyMember(
      centralDeviation −− slopeDependentDeviationThreshold,
      0.0, True, 0.01, False
    )

Step 7360 then computes the second of the our fuzzy truth variables that contribute to mildNegSlopeHighInspResistance, namely centralConcavityModPositive, from the central part feature centralConcavity (CF6), such that centralConcavityModPositive is true when the concavity of the central part is moderately positive. In one implementation, step 7360 computes centralConcavityModPositive as follows:

centralConcavityModPositive=FuzzyMember(
      centralConcavity, −0.05, False, 0.0, True, 0.3, True, 0.5, False)

The next step 7370 computes the third of the four fuzzy truth variables that contribute to mildNegSlopeHighInspResistance, namely postCentralActualAbovePredMildNegSlope, from the central part feature postCentralActualAbovePredicted (CF4), such that postCentralActualAbovePredMildNegSlope becomes true as postCentralActualAbovePredicted increases. In one implementation, step 7370 computes postCentralActualAbovePredMildNegSlope as follows:

postCentralActualAbovePredMildNegSlope=
      FuzzyMember(
        postCentralActualAbovePredicted, −0.4, False, −0.3, True)

Step 7375 follows, at which the method 7300 computes an exponential decay constant exponentialDecayConstant from the central part features centralSlope (CF2) and centralPart- DurationByFlowsMeanProduct (CF3). In one implementation, step 7375 computes exponentialDecayConstant as follows:

exponentialDecayConstant=
−centralSlope/centralPartDurationByFlowsMeanProduct

The next step 7380 computes the fourth of the four fuzzy truth variables that contribute to mildNegSlopeHighInspResistance, namely expDecayConstMildNegSlope, from exponentialDecayConstant. In one implementation, step 7380 computes expDecayConstMildNegSlope as follows:

expDecayConstMildNegSlope=FuzzyMember(
exponentialDecayConstant, −0.4, False, −0.2, True, 0.2, True, 0.4, False)

The final step 7390 of the method 7300 computes mildNegSlopeHighInspResistance as the fuzzy AND of the four fuzzy truth variables centralDeviationLow, mildNegSlopeHighInspResistance, postCentralActualAbovePredMildNegSlope, and expDecayConstMildNegSlope.

Step 7230 computes the flow limitation fuzzy truth variable FL3, named veryFlat, as the fuzzy AND of three fuzzy truth variables centralSlopeVeryFlat, centralConcavityVeryFlat, and propnAboveRampToStartOfCentralPartVeryFlat obtained from the central part features centralSlope (CF2), centralConcavity (CF6), and propnAboveRampToStartOfCentralPart (CF1) respectively. The three fuzzy truth variables that contribute to veryFlat indicate respectively that the inspiratory waveform is approximately horizontal and not convex upwards in the central part, and not concave upwards in the pre-central part. In one implementation, step 7230 computes centralSlopeVeryFlat, centralConcavityVeryFlat, and propnAboveRampToStartOfCentralPartVeryFlat as follows:

centralSlopeVeryFlat=FuzzyMember(
centralSlope, −0.1, False, −0.05, True, 0.05, True, 0.1, False)
centralConcavityVeryFlat=FuzzyMember(
centralConcavity, −0.1, False, 0.0, True)
propnAboveRampToStartOfCentralPartVeryFlat=
FuzzyMember(
propnAboveRampToStartOfCentralPart, −0.05, False, 0.0, True)

Step 7240 computes the flow limitation fuzzy truth variable FL4, named flatAndLargeInitialPeakMShapes, as the fuzzy AND of three fuzzy truth variables centralSlopeFlatAndLargeInitialPeakMShapes, centralConcavityFlatAndLargeInitialPeakMShapes, and propnAboveRampToStartOfCentralPartFlatAndLargeInitialPeakMShapes, obtained from the central part features centralSlope (CF2), centralConcavity (CF6), and propnAboveRampToStartOfCentralPart (CF1) respectively. The three fuzzy truth variables that contribute to flatAndLargeInitialPeakMShapes indicate respectively that the inspiratory waveform is approximately horizontal or M-shaped in the central part, and has a large initial peak. In one implementation, step 7240 computes centralSlopeFlatAndLargeInitialPeakMShapes, centralConcavityFlatAndLargeInitialPeakMShapes, and propnAboveRampToStartOfCentralPartFlatAndLargeInitialPeakMShapes as follows:

centralSlopeFlatAndLargeInitialPeakMShapes
=FuzzyMember(
centralSlope, −0.3, False, −0.2, True, 0.2, True, 0.3, False)
centralConcavityFlatAndLargeInitialPeakMShapes=
FuzzyMember(
centralConcavity, 0.1, False, 0.3, True)
propnAboveRampToStartOfCentralPartFlatAndLargeInitialPeakMShapes=
FuzzyMember(
propnAboveRampToStartOfCentralPart, 0.15, False, 0.3, True)

Step 7250 computes the flow limitation fuzzy truth variable FL5, named flatMNegSlopePostCentralHigh, using the following fuzzy logic operations on three intermediate fuzzy truth variables:

flatMNegSlopePostCentralHigh=
centralDeviationFlatMNegSlopePostCentralHigh
AND
(flatNegSlope OR flatMoreNegSlopeHighPostCentral)

The fuzzy truth variable centralDeviationFlatMNegSlopePostCentralHigh is obtained from the central part feature centralDeviation (CF5) and indicates that the central part of the inspiratory waveform is reasonably linear. In one implementation, step 7250 computes centralDeviationFlatMNegSlopePostCentralHigh as follows:

centralDeviationFlatMNegSlopePostCentralHigh=
FuzzyMember(
centralDeviation, 0.1, True, 0.2, False)

Step 7250 computes the fuzzy truth variable flatNegSlope as the fuzzy AND of two fuzzy truth variables centralSlopeFlatNegSlope and postCentralActualAbovePredFlatNegSlope, obtained from the central part features centralSlope (CF2) and postCentralActualAbovePredicted (CF4) respectively. The two fuzzy truth variables that contribute to flatNegSlope indicate respectively that the inspiratory waveform has a slight negative slope in the central part and is concave up in the post-central part. In one implementation, step 7250 computes centralSlopeFlatNegSlope and postCentralActualAbovePredFlatNegSlope as follows:

centralSlopeFlatNegSlope=FuzzyMember(
centralSlope, −0.45, False, −0.3, True, 0.1, True, 0.2, False)
postCentralActualAbovePredFlatNegSlope=
FuzzyMember(
postCentralActualAbovePredicted, 0.0, False, 0.2, True)

Step 7250 computes the fuzzy truth variable flatMoreNegSlopeHighPostCentral as the fuzzy AND of two fuzzy truth variables centralSlopeFlatMoreNegSlopeHighPostCentral and postCentralActualAbovePredFlatMoreNegSlopeHighPostCentral, obtained from the central part features centralSlope (CF2) and postCentralActualAbovePredicted (CF4) respectively. The two fuzzy truth variables that contribute to flatMoreNegSlopeHighPostCentral indicate respectively that the inspiratory waveform has a slightly more negative slope in the central part than flatNegSlope and has a peak in the post-central part. In one implementation, step 7250 computes centralSlopeFlatMoreNegSlopeHighPostCentral and postCentralActualAbovePredFlatMoreNegSlopeHighPostCentral as follows:

centralSlopeFlatMoreNegSlopeHighPostCentral=
FuzzyMember(
centralSlope, −0.55, False, −0.45, True, 0.1, True, 0.2, False)
postCentralActualAbovePredFlatMoreNegSlopeHighPostCentral=
FuzzyMember(
postCentralActualAbovePredicted, 0.2, False, 0.3, True)

The fuzzy truth variable flatMNegSlopePostCentralHigh (FL5) computed by step 7250 indicates that the inspiratory waveform is reasonably linear in the central part and either has a slight negative slope in the central part and is concave up in the post-central part, or has a more negative slope in the central part and has a peak in the post-central part.

Step 7260 computes the flow limitation fuzzy truth variable FL6, named concaveAndFlattish, as the fuzzy AND of two fuzzy truth variables centralSlopeConcaveAndFlattishFuzzy and centralConcavityConcaveAndFlattishFuzzy, obtained from the central part features centralSlopeConcaveAndFlattish (CF7) and centralConcavityConcaveAndFlattish (CF8) respectively. The two fuzzy truth variables that contribute to concaveAndFlattish indicate respectively that the central part of the inspiratory waveform is approximately horizontal and concave upwards. The flow limitation fuzzy truth variable concaveAndFlattish (FL6) is somewhat different from the first flow limitation fuzzy truth variable flattishMaybeConcave (FL1) on account of its dependence on central part features CF7 and CF8 that are computed over a slightly earlier definition of the central part than CF2 and CF6, which contribute to flattishMaybeConcave. That is, concaveAndFlattish indicates a slightly earlier appearance of horizontality and concavity than flattishMaybeConcave.

In one implementation, step 7260 computes centralSlopeConcaveAndFlattishFuzzy and centralConcavityConcaveAndFlattishFuzzy as follows:

centralSlopeConcaveAndFlattishFuzzy=FuzzyMember(
centralSlopeConcaveAndFlattish,
−0.4, False, −0.2, True, 0.2, True, 0.4, False)
centralConcavityConcaveAndFlattishFuzzy=
FuzzyMember(
centralConcavityConcaveAndFlattish,
0.3, False, 0.4, True)

FIG. 7E is a flow chart illustrating a method 7400 that may be used to implement step 7030 of the method 7000 in one form of the present technology. As mentioned above, step 7030 computes a fuzzy truth variable fuzzyLateFlatness that indicates that indicates a degree of "chairness" of the inspiratory waveform.

The method 7400 starts at step 7410, which checks whether the inspiratory time Ti is greater than an inspiratory time threshold and a typical recent ventilation Vtyp (returned by the typical recent ventilation determination algorithm 4328, described below) is greater than zero. In one implementation, the inspiratory time threshold is 0.5. If not ("N"), step 7440 sets fuzzyLateFlatness to "fuzzy false", and the method 7400 concludes. Otherwise ("Y"), step 7420 computes start and end locations of a "late section" of the inspiratory waveform. The aim of step 7420 is to define the late section so as to exclude any early peak in the inspiratory waveform. In one implementation, the late section is defined using rise time and fall time parameters of the pressure waveform template determined by the waveform determination algorithm 4322. In one such implementation, the start location of the late section is 1.25 multiplied by the rise time, and the end location is one quarter of the fall time back from the end of the inspiratory waveform. Other implementations of step 7420 defining the "late section" may be contemplated. For example, step 7420 may test a section somewhat later than the above-defined "late section" for being a reasonable approximation to a straight line with close to zero gradient, and if this is found, search backward to find the junction of this approximation with the rapid descent from the initial peak, using for example a criterion which is approximately equivalent to a large positive smoothed second derivative at the junction to locate this junction, then consider the late section to start approximately at this junction. This approach is more computationally intensive than the approach previously described.

The method 7400 then checks whether the duration of the late section defined at step 7420 is above a minimum fraction of the inspiratory time Ti. In one implementation the minimum fraction is 0.25. If not ("N"), the late section is deemed too short for a reliable analysis, and the method 7400 proceeds to step 7440, which sets fuzzyLateFlatness to "fuzzy false", and the method 7400 concludes. Otherwise ("Y"), the next step 7450 computes a normalising factor normFactorTypVent from the typical recent ventilation Vtyp, such that normFactorTyptVent generally increases as Vtyp increases. In one implementation, suitable for when Vtyp is an alveolar ventilation, step 7450 computes normFactorTypVent as Vtyp/4.5.

Step 7455 then computes a linear approximation to the inspiratory waveform over the late section. Step 7455 may use linear regression to compute the linear approximation, which is characterised by the mean flow flowMean, the slope flowSlope, and the root mean squared prediction error rootMeanSqFlowPredErr. Step 7455 then computes normalised versions of these three parameters by dividing each by the normalising factor normFactorTyp Vent:

lateFlowMean=flowMean/normFactorTypVent
lateSlope=flowSlope/normFactorTypVent
lateFlatness=rootMeanSqFlowPredErr/normFactorTypVent "Flatness" here refers to the extent to which the late section resembles a straight line, with no implications about its gradient, and the value of lateFlatness is zero when the late section is actually a straight line.

At the next step 7460, the method 7400 computes a quantity flowAboveLateBeforeLate that indicates by how much the inspiratory waveform before the late section exceeds the back projection of the linear approximation to the late section of the inspiratory waveform computed at step 7455, i.e. indicates the size of an early peak in the inspiratory waveform. To computeflowAboveLateBeforeLate, the earliest location before the late section at which the respiratory flow rate Qr exceeds the back projection of the linear approximation to the late section is found. The difference between the respiratory flow rate Qr and the linear approximation is then averaged between this location and the start location of the late section. The average is then normalised by the normalising factor normFactorTypVent to obtain flowAboveLateBeforeLate. Step 7460 then computes a fuzzy truth variable flowAboveLateBeforeLateAdequate from the value of flowAboveLateBeforeLate such that flowAboveLateBeforeLateAdequate is fuzzy false until flowAboveLateBeforeLate exceeds a threshold that generally increases with the mean flow rate of the late section lateFlowMean (which was computed at step 7455). The effect of the dependence of flowAboveLateBeforeLateAdequate on lateFlowMean is that larger early peaks are required to causefuzzyLateFlatness to be fuzzy true as the mean flow rate of the late section increases.

In one implementation, step 7460 computes flowAboveLateBeforeLateAdequate as follows:

flowAboveLateBeforeLateAdequate = FuzzyMember(
flowAboveLateBeforeLate,
LOWER_THRESH, False,
UPPER_THRESH, True
)

where LOWER_THRESH and UPPER_THRESH are constant thresholds equal in one implementation to 0.5*lateFlowMean and lateFlowMean respectively. In one implementation, the thresholds have minimum values of 2.25 and 4.5 litres/minute respectively, regardless of the value of lateFlowMean.

The method 7400 proceeds to step 7465, which computes a fuzzy truth variable lateFlatnessFuzzyComp which turns from true to false as lateFlatness increases, i.e. the late section becomes less linear. In one implementation, step 7465 computes lateFlatnessFuzzyComp as follows:

```
lateFlatnessFuzzyComp = FuzzyMember(
    lateFlatness,
    LOWER_FLATNESS_THRESH, True,
    UPPER_FLATNESS_THRESH, False
    )
``` where LOWER_FLATNESS_THRESH and UPPER_FLATNESS_THRESH are constant thresholds equal in one implementation to 0.6 and 0.9 respectively.

The next step 7470 computes a fuzzy truth variable lateSlopeFuzzyComp that is only true when lateSlope is "moderate", i.e. within a certain range. That is, large positive or negative values of lateSlope may cause lateSlopeFuzzyComp to be false. In one implementation, step 7470 computes lateSlopeFuzzyComp as follows:

```
lateSlopeFuzzyComp = FuzzyMember(
    lateSlope,
    LOWER_SLOPE_THRESH, False,
    UPPER_SLOPE_THRESH, True,
    6.0, True,
    9.0, False,
    )
``` where LOWER_SLOPE_THRESH and UPPER_SLOPE_THRESH are thresholds. In one implementation, the thresholds generally become more negative as late-FlowMean increases, meaning that larger negative slopes are permitted within the definition of "moderate" as the mean flow rate of the late section increases. In one implementation, step 7470 computes LOWER_SLOPE_THRESH and UPPER_SLOPE_THRESH as follows:

LOWER_SLOPE_THRESH=−9.0−3*slope ThresholdExtension

UPPER_SLOPE_THRESH=−6.0−3*slope ThresholdExtension where slopeThresholdExtension is a real number that decreases from 1 to 0 as lateFlowMean increases. In one implementation, step 7470 computes slopeThresholdExtension as follows:

```
slopeThresholdExtension = FuzzyDeweight(
    lateFlowMean,
    0.6, 1.0,
    0.9, 0.0
    )
```

The final step 7475 of the method 7400 computesfuzzyLateFlatness as the fuzzy AND of the fuzzy truth variables flowAboveLateBeforeLateAdequate, lateFlatnessComp, and lateSlopeFuzzyComp computed at steps 7460, 7465, and 7470 respectively.

7.4.3.2.5 M-Shape Detection

In one form of the present technology, the therapy engine 4320 module executes one or more algorithms to detect "M-shape" in the inspiratory waveform. In one form, the M-shape detection algorithm 4326 receives as an input a respiratory flow rate signal Qr and provides as an output a measure indicative of the extent to which each inspiratory waveform exhibits M-shape.

M-shaped inspiratory waveforms with tidal volumes or other breathwise ventilation values not much greater than typical recent values are indicative of flow limitation. Such inspiratory waveforms have a relatively rapid rise and fall and a dip or "notch" in flow approximately in the centre, the dip being due to flow limitation (see FIGS. 6E and 6F). At higher tidal volumes or breathwise ventilation values, such waveforms are generally behavioural, i.e. micro-arousals during sleep, or sighs, and are not indicative of flow limitation.

To detect M-shaped waveforms, the M-shape detection algorithm 4326 determines the similarity of the inspiratory waveform to a waveform which is broadly M-shaped.

FIG. 7F is a flow chart illustrating a method 7500 that may be used to implement the M-shape detection algorithm 4326 in one form of the present technology.

Since the notch may not be at the centre of the inspiratory waveform, the method 7500 attempts to find the location of the notch, and then linearly time-distorts the waveform so that the notch is at the centre of the waveform. To find the notch, the first step 7510 performs a modified convolution of the normalised inspiratory waveform $f(t)$ (wherein the normalisation is division by the mean) with a V-shaped kernel V(t) of length Ti/2, centred on zero, where Ti is the inspiratory time:

$$V(t) = 8\left|\frac{t}{T_i}\right| - 1$$

The modified convolution is based on separate convolutions with the left and right halves of the kernel V(t). The left half convolution is calculated as $$I_L(\tau) = \int_{-\frac{T_i}{4}}^{0} V(t)f(t-\tau)dt$$

and the right half convolution as $$I_R(\tau) = \int_{0}^{\frac{T_i}{4}} V(t)f(t-\tau)dt$$

The modified convolution I(t) is computed as a combination of the left and right half convolutions IL(t) and IR(t) such that if either of the left and right half convolutions is zero, the result is zero, regardless of the other quantity, and if both are 1, the result is 1. Thus constrained, the combination of the left and right half convolutions resembles a logical "and" function in some sense, hence is given the name "V-anded convolution". In one implementation, the combination is a modified geometric mean of the left and right half convolutions:

$$I(\tau) = \begin{cases} \sqrt{I_L(\tau)I_R(\tau)}, & I_L(\tau) > 0 \text{ and } I_R(\tau) > 0 \\ 0 & \text{otherwise} \end{cases} \quad (1)$$

The above constraint provides a condition that the inspiratory waveform to the left of the posited notch is generally increasing leftwards, and that to the right of the notch is generally increasing rightwards. This provides more specificity than simply summing the left and right integrals. In the implementation given in equation (1), the integrals of the product of the time-shifted normalised inspiratory waveform with each half-V must be strictly positive, otherwise the V-anded convolution is zero. This prevents a variety of pathologies, for example, when the part of the inspiratory flow to the left of the centre of the V does not actually increase leftwards, but the integral of the right half of the V waveform is so large that it overwhelms an actually decreasing left half.

The V-anded convolution is performed with the position of the centre of the kernel V(t) ranging from Ti/4 to 3Ti/4, thus yielding results for the central half of the inspiratory waveform.

Step 7520 finds the location at which the modified convolution I(t) peaks, and if the height of this peak is greater than a threshold, a notch is deemed to exist at the location $t_{notch}$ of the centre of the kernel V(t) at which this peak is located. In one implementation, the threshold is set to 0.15.

If a notch is found by step 7520 ("Y") at the location $t_{notch}$, the inspiratory waveform $f(t)$ is then, at step 7530, time distorted or "symmetrised" so that half the waveform is to the left of $t_{notch}$ and half is to the right. This operation gives a time-distorted or "symmetrised" version G(t) of the inspiratory waveform $f(t)$:

$$G(t) = \begin{cases} f\left(\dfrac{t}{\left(\frac{T}{2}\right)} t_{notch}\right), & t < \dfrac{T}{2} \\ f\left(t_{notch} + \left(\dfrac{t - \frac{T}{2}}{\frac{T}{2}}\right)(T - t_{notch})\right) & t \geq \dfrac{T}{2} \end{cases}$$

If no notch is found at step 7520 ("N"), step 7535 sets G(t) to the inspiratory waveform $f(t)$, since some waveforms that do not exhibit a detectable notch may still have M-shaped flow limitation.

To detect M-shaped flow limitation in the symmetrised waveform G(t), first and third sinusoidal harmonic functions of half-width Ti are first defined as $$F_1(t) = \sin\left(\pi \dfrac{t}{Ti}\right)$$

and $$F_3(t) = \sin\left(3\pi \dfrac{t}{Ti}\right)$$

These two harmonic functions are orthogonal on [0, Ti]. For t in [0, Ti], $F_3(t)$ is broadly similar to an M-shaped inspiratory waveform, and Fi(t) is broadly similar to a normal inspiratory waveform. Hence the extent to which the symmetrised waveform G(t) resembles $F_3(t)$ is an indicator of how much the waveform resembles an M. Step 7540 calculates this extent. In one implementation, step 7540 calculates the power in the first harmonic of the symmetrised waveform G(t) as the square of the inner product of the first harmonic function Fi with the symmetrised waveform G(t), and the power in the third harmonic of the symmetrised waveform G(t) as the square of the inner product of the third harmonic function $F_3$ with the symmetrised waveform G(t). Both inner products are calculated over the inspiratory interval [0, Ti]. Step 7540 then computes the extent to which the symmetrised waveform G(t) resembles $F_3(t)$ as the ratio M3Ratio of the power in the third harmonic of the symmetrised waveform G(t) to the sum of the powers in the first and third harmonics of the symmetrised waveform G(t):

$$M3Ratio = \dfrac{\langle F_3, G \rangle_{[0,Ti]}^2}{\langle F_1, G \rangle_{[0,Ti]}^2 + \langle F_3, G \rangle_{[0,Ti]}^2}$$

When M3Ratio is large, the inspiratory waveform typically resembles an M. But M3Ratio can also be large if the waveform is very asymmetric, with a much higher mean flow in either the first or second half of the waveform than in the other half. To exclude this possibility, step 7540 also calculates a measure Symm of the symmetry of the inspiratory waveform $f(t)$ about the notch location. In one implementation, step 7540 calculates the third harmonic components of the first and second halves of the symmetrised waveform G(t):

$$M_{3L} = \langle F_3, G \rangle_{[0, \frac{Ti}{2}]}$$

$$M_{3R} = \langle F_3, G \rangle_{[\frac{Ti}{2}, Ti]}$$

Step 7540 then calculates the measure Symm as the ratio of the lesser of these components to the sum of their absolute values:

$$Symm = \dfrac{\min(M_{3L}, M_{3R})}{|M_{3L}| + |M_{3R}|}$$

Step 7550 then tests whether the measure Symm is less than a low threshold, set in one implementation to 0.3. If so ("Y"), the inspiratory waveform is deemed not to be symmetrically M-shaped, and a quantity M3SymmetryRatio, which is a measure of the extent to which the inspiratory waveform is symmetrically M-shaped, is set equal to zero at step 7560. Otherwise ("N"), M3SymmetryRatio is set equal to M3Ratio at step 7570.

The final step 7580 computes a variable RxProportion from M3SymmetryRatio so as to generally increase from 0 to 1 as M3SymmetryRatio increases. In one implementation, step 7580 computes RxProportion as follows:

```
RxProportion = FuzzyDeweight(
    M3SymmetryRatio,
    LOWER_M3_SYMMETRYRATIO_THRESH, 0.0,
    UPPER_M3_SYMMETRYRATIO_THRESH, 1.0
    )
``` where LOWER_M3SYMMETRYRATIO_THRESH and UPPER_M3SYMMETRYRATIO_THRESH are constants, equal in one implementation to 0.17 and 0.3 respectively. The variable RxProportion is an indicator in the range [0, 1] of the degree of M-shape of the inspiratory portion of the respiratory flow rate waveform.

7.4.3.2.6 Apnea Detection

In one form of the present technology, the therapy engine module 4320 executes an apnea detection algorithm 4325 to detect apneas.

In one form, the apnea detection algorithm 4325 receives as an input a respiratory flow rate signal Qr and provides as an output a series of events indicating starts and ends of detected apneas.

FIG. 7G is a flow chart illustrating a method 7600 of detecting apneas that may be used to implement the apnea detection algorithm 4325 in one form of the present technology.

The method 7600 generally looks for low ventilation in relation to an expected normal ventilation Vnorm. In some implementations, the expected normal ventilation Vnorm may be the typical recent ventilation Vtyp returned by the typical recent ventilation determination algorithm 4328, described below.

Ventilation is measured at two different timescales, one comparable to a breath and one of several breaths' duration, and low ventilation in relation to the expected normal ventilation Vnorm at either timescale indicates an apnea is in progress. The method 7600 contains hysteresis, in that if an apnea has previously been determined to be in progress but neither of the two criteria that indicate an apnea is in progress is true, a further criterion derived from the ventilation relative to expected normal ventilation Vnorm must be true for the apnea to have ended. The hysteresis of the method 7600 gives the method 7600 greater robustness to transient increases in respiratory flow rate than previous methods of detecting apneas.

The method 7600 also returns an effective duration for the apnea for treatment purposes. The effective duration of the apnea is by default the total duration of its closed-airway portions, that is, the sum of the elapsed time between the commencement of each closed-airway portion of the apnea and its termination. However, the effective duration of the apnea may be reduced from this default "closed duration" value by either or both of two separate deweighting factors, one derived from the ventilation relative to the expected normal ventilation Vnorm, and one derived from the estimated leak flow rate Ql during the apnea. The effect of this deweighting is that to the extent that leak is large, and/or the ventilation approaches the expected normal ventilation Vnorm during the apnea, the effective duration of the apnea is shorter than its closed duration, so the prescribed EPAP increase is less.

The method 7600 starts at step 7610, which computes a short-time ventilation Vshort as the mean over the most recent "short interval" of the instantaneous ventilation Vint returned by the ventilation determination algorithm 4323. In one implementation, the short interval is two seconds. Step 7610 also computes a "very fast" relative ventilation error veryFastRelVentError as a relative difference between the "very fast ventilation" VveryFast obtained from the ventilation determination algorithm 4323 and the expected normal ventilation Vnorm. Step 7610 computes the very fast relative ventilation error veryFastRelVentError as follows:

$$veryFastRelVentErr = (VveryFast - Vnorm)/Vnorm$$

The method 7600 then proceeds to check at step 7615 whether the short-time ventilation Vshort is less than or equal to than a low fraction of the expected normal ventilation Vnorm. In one implementation the low fraction is set to 0.2. If so ("Y"), an apnea is detected. If not ("N"), the next step 7620 checks whether veryFastRelVentError is less than or equal to an apnea threshold, equal in one implementation to −0.95. The check at step 7620 is equivalent to determining whether the very fast ventilation VveryFast is less than a small fraction of the expected normal ventilation Vnorm, the small fraction in this case being 0.05. If so ("Y"), an apnea is detected.

The method 7600 maintains the current state of apnea as a Boolean indicator inApnea (which is initialised to False at the start of therapy). If either apnea start criterion (tested in steps 7615 and 7620) is satisfied ("Y"), the method 7600 checks at step 7630 whether an apnea was already in progress by checking whether inApnea is True. If not ("N"), the next step 7635 issues an Apnea Start event and sets inApnea to True to indicate that the patient 1000 has just entered an apnea state. Step 7645 then sets the effective duration of the apnea to zero. The effective duration of the apnea is stored in a variable effectiveApneaDuration that is maintained as long as the apnea state persists.

The next step 7670 sets a variable called intVentErrAboveThresh to zero. This variable, which holds a running total of the amount by which the very fast relative ventilation error veryFastRelVentError computed at step 7610 exceeds the apnea threshold, is used to confirm that an apnea has indeed ended if neither of the two apnea start criteria tested at 7615 and 7620 is satisfied.

If the check at step 7630 finds that the patient 1000 is already experiencing an apnea ("Y"), the method 7600 proceeds directly to step 7670 to set the running total intVentErrAboveThresh to zero as described above. The method 7600 then proceeds to step 7680 described below.

If neither of the apnea start criteria are satisfied ("N" at steps 7615 and 7620), the method 7600 checks whether an apnea is already in progress by checking at step 7640 whether inApnea is True. If not ("N"), the method 7600 concludes at step 7655. Otherwise ("Y"), it is possible that the current apnea has ended. However, as mentioned above, the method 7600 confirms this by proceeding to step 7650 which updates the running total intVentErrAboveThresh by adding the current difference between veryFastRelVentError and the apnea threshold, provided that difference is greater than zero.

Step 7660 then checks an apnea end criterion, namely whether the running total intVentErrAboveThresh is greater than a threshold. In one implementation, this threshold is set to 0.15. If the apnea end criterion is satisfied ("Y"), the apnea is ended, so step 7665 ends the apnea state by issuing an Apnea End event and sets inApnea to false. The method 7600 then concludes.

If the apnea end criterion is not satisfied, i.e. the running total intVentErrAbove Thresh is not greater than the threshold ("N" at step 7660), the apnea is still in progress, and the method 7600 proceeds to step 7680 described below.

Step 7680 computes a deweighting factor apneaTimeWeighting from veryFastRelVentError such that apneaTimeWeighting decreases from 1 to 0 as veryFastRelVentError increases above the apnea threshold. In one implementation, step 7680 computes apneaTimeWeighting as follows:

```
apneaTimeWeighting = FuzzyDeweight(
    veryFastRelVentError,
    APNEA_THRESHOLD, 1.0,
    APNEA_THRESHOLD_PLUS_A_BIT, 0.0
    )
``` where APNEA_THRESHOLD is the apnea threshold of step 7620 and APNEA_THRESHOLD_PLUS_A_BIT is a threshold that is set slightly higher than APNEA_THRESHOLD, equal in one implementation to APNEA_THRESHOLD+0.05. The deweighting factor apneaTimeWeighting discounts the contribution of the current time instant to the final effective duration of the apnea.

Step 7685 then computes a second deweighting factor leakDeweighting, based on the leak flow rate estimate Ql from the leak flow rate estimation algorithm 4316. In one implementation, step 7685 computes LeakDeweighting such that as the estimated leak flow rate increases, LeakDeweighting decreases from 1 to 0.

$$\begin{aligned}\text{LeakDeweighting} = \text{FuzzyDeweight}(\\ \text{Ql},\\ \text{LOWER\_LEAK\_THRESH}, 1.0,\\ \text{UPPER\_LEAK\_THRESH}, 0.0\\ )\end{aligned}$$

where LOWER_LEAK_THRESH and UPPER_LEAK_THRESH are constants, equal in one implementation to 48 litres/minute and 60 litres/minute respectively.

Finally, at step 7690, the method 7600 updates the effective duration of the apnea effectiveApneaDuration taking into account the two deweighting factors apneaTimeWeighting and LeakDeweighting and the airway patency determined by the airway patency determination algorithm 4327 (described below).

In one implementation, step 7690 updates the effective duration of the apnea by incrementing the current value of effectiveApneaDuration by the product of the two deweighting factors apneaTimeWeighting and LeakDeweighting, if the airway is currently determined to be closed. Otherwise, step 7690 does not update the effective duration of the apnea.

The final value of effectiveApneaDuration returned by the apnea detection algorithm 4325 for a completed apnea will be in units of time of duration equal to the apnea detection interval. The apnea detection interval is the reciprocal of the frequency at which the apnea detection algorithm 4325 is executed by the therapy engine module 4320.

7.4.3.2.7 Typical Recent Ventilation Determination

In one form of the present technology, the central controller 4230 takes as input the measure of current ventilation, Vent, and executes one or more typical recent ventilation determination algorithms 4328 for the determination of a value Vtyp indicative of the typical recent ventilation of the patient 1000.

The typical recent ventilation Vtyp is the value around which the distribution of the measure of current ventilation Vent over multiple time instants over some predetermined timescale tends to cluster, that is, a measure of the central tendency of the measure of current ventilation over recent history. In one implementation of the typical recent ventilation determination algorithm 4328, the recent history is of the order of several minutes, but in any case should be longer than the timescale of Cheyne-Stokes waxing and waning cycles. The typical recent ventilation determination algorithm 4328 may use any of the variety of well-known measures of central tendency to determine the typical recent ventilation Vtyp from the measure of current ventilation, Vent. One such measure is the output of a low-pass filter on the measure of current ventilation Vent, with time constant equal to one hundred seconds.

7.4.3.2.8 Airway Patency Determination

In one form of the present technology, the central controller 4230 executes an airway patency determination algorithm 4327 for the determination of airway patency. In some implementations, the airway patency determination algorithm 4327 returns either "closed" or "open", or equivalent Boolean values, e.g. "true" indicating closed and "false" indicating open.

As described above, in the absence of spontaneous triggering, the RPT device 4000 delivers backup breaths at the backup rate Rb. Backup breaths delivered during an apnea state as detected by the apnea detection algorithm 4325 are referred to as "probe breaths".

Probe breaths may have the same amplitude as normal backup breaths (the pressure support value A), but may have their own timing parameters, i.e. special values of Timin and Timax referred to as Timin_PB and Timax_PB. The values of Timin_PB and Timax_PB may be derived from other settings of the RPT device 4000. In one implementation, Timin_PB and Timax_PB are defined as $$Timin\_PB = \text{Max}(0.1, \text{Min}(1.2, 0.4 * Tbackup)) \quad (2)$$

$$Timax\_PB = \text{Min}(\text{Max}(Timax, Timin\_PB), 0.4 * Tbackup)) \quad (3)$$

The main reason for modifying Timin for probe breaths is to avoid the probe breath being early cycled such that the probe breath duration would become too short to provide reliable information relative to the state of the upper airway.

In some implementations, the airway patency determination algorithm 4327 is not invoked when the pressure support A (see below) of the therapy is above a threshold, for example 10 cmH$_2$O. For pressure support A above this threshold, any apnea is deemed to be a closed airway apnea.

The airway patency determination algorithm 4327 analyses the respiratory flow rate Qr in response to the probe breaths delivered while the RPT device 4000 is in an apnea state to determine the patency of the airway during the apnea. The opened/closed airway determination is based on analysing the shape of the inspiratory and expiratory portions of the respiratory flow rate signal Qr in response to the probe breaths. Generally speaking, a "decreasing" portion is indicative of an open airway, while a "plateauing" portion is indicative of a closed airway.

FIGS. 7H and 7I contain a flow chart illustrating a method 7700 that may be used to implement the airway patency determination algorithm 4327 in one form of the present technology. The method 7700 takes as inputs the inspiratory portion of the respiratory flow rate waveform (the inspiratory waveform) and the expiratory portion of the respiratory flow rate waveform (the expiratory waveform) in response to a probe breath. The method 7700 starts at step 7710, which "trims" the inspiratory and expiratory waveforms. The purpose of trimming is to remove the "initial rush" of flow as gaseous compression and compliant elements in the airpath take up some volume. In one implementation, step 7710 trims the inspiratory waveform to the "late section" of the inspiratory waveform as defined above in relation to the "chairness" detection step 7030 of the method 7000. In such an implementation, the start location of the late section is 1.25 multiplied by the rise time, and the end location of the late section is one quarter of the fall time back from the end of the inspiratory waveform. The expiratory portion may be trimmed in similar fashion, interchanging rise time and fall time.

Step 7720 follows, at which linear regression is performed on the trimmed inspiratory and expiratory waveforms. Linear regression finds the "best" (in a least-squares sense) straight-line approximation to a function over an interval, returning the following parameters: gradient, y-intercept (initial value), mean value, and correlation coefficient (which indicates the "goodness of fit" of the straight-line approximation). At the next step 7730, the method 7700 computes a mean value Qmean of the absolute value of the respiratory flow rate Qr over the trimmed inspiratory and expiratory waveforms. Step 7730 then divides this value Qmean by the typical recent ventilation Vtyp calculated by the typical recent ventilation determination algorithm 4328 to obtain an value Sz indicative of the size of the response to the probe breath in relation to the level of current ventilation. Step 7740 then determines an upper threshold and a lower threshold with which the breath size indicator value Sz is to be compared. In some forms of step 7740, the lower threshold is a function of the current pressure support A (see below), which is the amplitude of the delivered probe breath. In one such form, the lower threshold is the value of A clipped to the range [4 cm $H_2O$, 8 cm $H_2O$] and divided by 20 cm $H_2O$. The lower threshold will therefore range from 0.2 to 0.4 under such an implementation. In one implementation of step 7740, the upper threshold is set to 0.75.

Step 7750 then compares the breath size indicator value Sz computed at step 7730 with the lower threshold. If the breath size indicator value Sz is below the lower threshold ("Y"), the method 7700 concludes at step 7770 by returning the value "closed" as the respiratory flow rate size is too small for the airway to be deemed open. Otherwise ("N"), the method 7700 proceeds to step 7760, which determines whether the breath size indicator value Sz is above the upper threshold. If so ("Y"), the method 7700 concludes at step 7770 by returning the value "open" as the respiratory flow rate size is too large for the airway to be deemed closed. If not ("N"), the method 7700 proceeds to step 7790, which computes a value Sz_rel for the breath size indicator value Sz relative to the lower and upper thresholds as follows:

$$Sz\_rel = (Sz - \text{lower threshold})/(\text{upper threshold} - \text{lower threshold})$$

The relative breath size indicator value Sz_rel ranges from 0 (when the breath size indicator value Sz is equal to the lower threshold) to 1 (when the breath size indicator value Sz is equal to the upper threshold).

The method 7700 then continues from step 7810 in FIG. 7I for a final determination of the airway patency based on the relative breath size indicator value Sz_rel and the straight-line approximations to the trimmed inspiratory and expiratory waveforms found in step 7720 (which may in some implementations take place after the steps 7730 to 7790).

In step 7810, the method 7700 computes the "final value" of the straight-line approximation to the trimmed inspiratory waveform. The final value may be computed by adding the y-intercept (initial value) to the product of the gradient and the duration of the trimmed inspiratory portion. Step 7810 then computes an "inspiratory flatness ratio" as the ratio of the final value to the initial value of the straight-line approximation to the trimmed inspiratory waveform.

In the next step 7820, the method 7700 computes the "final value" of the straight-line approximation to the trimmed expiratory waveform. The final value may be computed by adding the y-intercept (initial value) to the product of the gradient and the duration of the trimmed expiratory portion. Step 7820 then computes an "expiratory flatness ratio" as the ratio of the final value to the initial value of the straight-line approximation to the trimmed expiratory waveform.

Step 7830 follows, at which the method 7700 computes inspiratory and expiratory thresholds with which the inspiratory and expiratory flatness ratios respectively are to be compared. If either ratio falls below its corresponding threshold, the airway is determined to be open; otherwise, the airway is determined to be closed.

In one implementation of step 7830, the thresholds may be computed so as to be linearly increasing as the relative breath size indicator value Sz_rel increases from 0 to 1. For example, $$\text{inspiratory\_threshold} = Sz\_rel \tag{4}$$

$$\text{expiratory\_threshold} = Sz\_rel \tag{5}$$

The effect of this is that for probe breaths whose size indicator value Sz is large enough to be close to the upper threshold above which the airway is determined to be open in step 7780, the inspiratory and expiratory thresholds will be close to 1, so the inspiratory and expiratory flatness ratios are more likely to be below threshold, and the airway to be determined to be open. Conversely, for probe breaths whose size indicator value Sz is small enough to be close to the lower threshold below which the airway is determined to be closed in step 7770, the inspiratory and expiratory thresholds will be close to 0, so the inspiratory and expiratory flatness ratios are more likely to be above threshold, and the airway determined to be closed.

In some implementations, this latter determination may qualified by adjusting the inspiratory and expiratory thresholds based on the "goodness of fit" of the straight-line approximations to the inspiratory and expiratory waveforms. To the extent that the straight-line approximation is a "good fit", as quantified by the correlation coefficient, the lowest value of the threshold is proportionally greater than zero, making an "open" determination more likely even for relatively small breaths. In one such implementation, a "goodness of fit" parameter is computed for the inspiratory waveform as $$\text{insp\_goodness} = \text{InterpOnInterval}(\text{Insp\_corrcoefft}, -0.95, 0.5, -0.8, 0.0)$$

which is equal to 0.5 when the inspiratory correlation coefficient is below −0.95 (indicating a good fit), equal to 0 when the inspiratory correlation coefficient is above −0.8, and linearly decreasing from 0.5 to 0 when the inspiratory correlation coefficient is above −0.95 and below −0.8.

In this implementation, a "goodness of fit" parameter is computed for the expiratory waveform as $$\text{exp\_goodness} = \text{InterpOnInterval}(\text{Exp\_corrcoefft}, 0.8, 0, 0.95, 0.5)$$

which is equal to 0.5 when the expiratory correlation coefficient is above 0.95 (indicating a good fit), equal to 0 when the expiratory correlation coefficient is below 0.8, and linearly increasing from 0 to 0.5 when the expiratory correlation coefficient is above 0.8 and below 0.95.

In this implementation, equations (4) and (5) for the inspiratory and expiratory thresholds are modified as follows:

$$\text{inspiratory\_threshold} = \text{insp\_goodness} + (1 - \text{insp\_goodness}) * Sz\_rel$$

$$\text{expiratory\_threshold} = \text{exp\_goodness} + (1 - \text{exp\_goodness}) * Sz\_rel$$

In this implementation, the inspiratory and expiratory thresholds linearly increase from 0 to 1 as Sz_rel increases from 0 to 1 when the "goodness of fit" is poor, but when it is good, the thresholds linearly increase from 0.5 to 1 as Sz_rel increases from 0 to 1. Thus for any given value of Sz_rel, the better the straight-line fit, the higher are the thresholds, increasing the chance that the airway will be found to be open for reasonably "linear" breaths.

Returning to the method 7700, at step 7840 the inspiratory flatness ratio is compared with the inspiratory threshold. If the inspiratory flatness ratio is below the inspiratory threshold ("Y"), at step 7870 the airway is determined to be open and the method 7700 concludes. Otherwise ("N"), at step 7850 the expiratory flatness ratio is compared with the expiratory threshold. If the expiratory flatness ratio is below the expiratory threshold ("Y"), at step 7870 the airway is determined to be open and the method 7700 concludes. Otherwise ("N"), at step 7860 the airway is determined to be closed and the method 7700 concludes.

7.4.3.2.9 Determination of Therapy Parameters

In some forms of the present technology, the central controller 4230 executes one or more therapy parameter determination algorithms 4329 for the determination of one or more therapy parameters using the values returned by one or more of the other algorithms in the therapy engine module 4320.

In one form of the present technology, the therapy parameter is an instantaneous treatment pressure Pt. In one implementation of this form, the therapy parameter determination algorithm 4329 determines the treatment pressure Pt as follows:

$$Pt = A\Pi(\Phi, t) + P_0 \tag{6}$$

where A is the amount of "pressure support", $\Pi(\Phi,t)$ is the waveform template value (in the range 0 to 1) at the current values $\Phi$ of phase and t of time, and $P_0$ is a base pressure.

By determining the treatment pressure Pt using equation (6) and applying it as a set point in the controller 4230 of the RPT device 4000, the therapy parameter determination algorithm 4329 oscillates the treatment pressure Pt in synchrony with the spontaneous respiratory effort of the patient 1000. That is, based on the typical waveform templates $\Pi(\Phi)$ described above, the therapy parameter determination algorithm 4329 increases the treatment pressure Pt at the start of, or during, or inspiration and decreases the treatment pressure Pt at the start of, or during, expiration. The (non-negative) pressure support A is the amplitude of the oscillation.

If the waveform determination algorithm 4322 provides the waveform template $\Pi(\Phi)$ as a lookup table, the therapy parameter determination algorithm 4329 applies equation (6) by locating the nearest lookup table entry to the current value $\Phi$ of phase returned by the phase determination algorithm 4321, or by interpolation between the two entries straddling the current value $\Phi$ of phase.

The values of the pressure support A and the base pressure $P_0$ may be determined by the therapy parameter determination algorithm 4329 depending on the chosen respiratory pressure therapy mode in the manner described below.

7.4.3.3 Therapy Control Module

Therapy control module 4330 in accordance with one aspect of the present technology receives as inputs the therapy parameters from the therapy parameter determination algorithm 4329 of the therapy engine module 4320, and controls the pressure generator 4140 to deliver a flow of air in accordance with the therapy parameters.

In one form of the present technology, the therapy parameter is a treatment pressure Pt, and the therapy control module 4330 controls the pressure generator 4140 to deliver a flow of air whose mask pressure Pm at the patient interface 3000 is equal to the treatment pressure Pt.

7.4.3.4 Detection of Fault Conditions

In one form of the present technology, the central controller 4230 executes one or more methods for the detection of fault conditions. The fault conditions detected by the one or more methods may include at least one of the following:
Power failure (no power, or insufficient power)
Transducer fault detection
Failure to detect the presence of a component
Operating parameters outside recommended ranges (e.g. pressure, flow rate, temperature, $PaO_2$)
Failure of a test alarm to generate a detectable alarm signal.

Upon detection of the fault condition, the corresponding algorithm signals the presence of the fault by one or more of the following:
Initiation of an audible, visual &/or kinetic (e.g. vibrating) alarm
Sending a message to an external device
Logging of the incident

7.5 Humidifier

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

7.6 Respiratory Pressure Therapy Modes

Various respiratory pressure therapy modes may be implemented by the RPT device 4000 depending on the values of the parameters A and $P_0$ in the treatment pressure equation (6) used by the therapy parameter determination algorithm 4329 in one form of the present technology.

7.6.1 CPAP Therapy

In some implementations, the pressure support A is identically zero, so the treatment pressure Pt is identically equal to the base pressure $P_0$ throughout the respiratory cycle. Such implementations are generally grouped under the heading of CPAP therapy. In such implementations, there is no need for the therapy engine module 4320 to determine phase $\Phi$ or the waveform template $\Pi(\Phi)$.

7.6.2 Ventilation Therapy

In other implementations, the value of pressure support A in equation (6) may be positive. Such implementations are known as ventilation therapy. In some forms of ventilation therapy, known as fixed pressure support ventilation therapy, the pressure support A is fixed at a predetermined value, e.g. 10 cm H$_2$O. The predetermined value of pressure support A is a setting of the RPT device 4000, and may be set for example by hard-coding during configuration of the RPT device 4000 or by manual entry through the input device 4220.

The value of the pressure support A may be limited to a range defined as [Amin, Amax]. The pressure support limits Amin and Amax are settings of the RPT device 4000, set for example by hard-coding during configuration of the RPT device 4000 or by manual entry through the input device 4220. A minimum pressure support Amin of 3 cm H$_2$O is of the order of 50% of the pressure support required to perform all the work of breathing of a typical patient in the steady state. A maximum pressure support Amax of 12 cm H$_2$O is approximately double the pressure support required to perform all the work of breathing of a typical patient, and therefore sufficient to support the patient's breathing if they cease making any efforts, but less than a value that would be uncomfortable or dangerous.

7.6.2.1 Auto-Titration of the EPAP

In ventilation therapy modes, the base pressure P$_0$ is sometimes referred to as the EPAP. The EPAP may be a constant value that is prescribed or determined via a process known as titration. Such a constant EPAP may be set for example by hard-coding during configuration of the RPT device 4000 or by manual entry through the input device 4220. This alternative is sometimes referred to as fixed-EPAP ventilation therapy. Titration of the constant EPAP for a given patient may be performed by a clinician with the aid of a PSG study carried out during a titration session.

Alternatively, the therapy parameter determination algorithm 4329 may repeatedly compute the EPAP during ventilation therapy. In such implementations, the therapy parameter determination algorithm 4329 repeatedly computes the EPAP as a function of indices or measures of upper airway instability returned by the respective algorithms in the therapy engine module 4320, such as one or more of inspiratory flow limitation and apnea. Because the repeated computation of the EPAP resembles the manual adjustment of the EPAP by a clinician during titration of the EPAP, this process is also sometimes referred to as auto-titration of the EPAP, and the overall therapy is known as auto-titrating EPAP ventilation therapy, or auto-EPAP ventilation therapy.

The role of airway patency is particularly important in auto-EPAP ventilation therapy. When the pressure support A is greater than some threshold (e.g. 10 cm H$_2$O), if the apnea detection algorithm 4325 detects an apnea, it may be inferred that the airway is closed, since otherwise the pressure support A would be large enough to generate some sort of respiratory airflow and an apnea would not have been detected.

However, when the pressure support A is less than the threshold, if the apnea detection algorithm 4325 detects an apnea, the RPT device 4000 cannot immediately infer that the airway is closed. The airway patency determination algorithm 4327 therefore repeatedly determines a measure of airway patency while the RPT device 4000 is in an apnea state. While the apnea state persists, the apnea detection algorithm 4325 accumulates the duration over which the upper airway is determined to be closed. This accumulated duration is defined as the effective duration of the apnea.

At the conclusion of the apnea state, the RPT device 4000 determines an EPAP increment (prescription) from the effective duration of the apnea. The longer is the effective duration of the apnea, the greater is the increment.

FIG. 8A is a flow chart illustrating a method 8000 of auto-titrating the EPAP suitable for use in conjunction with non-invasive ventilation therapy. The method 8000 may be repeatedly implemented as part of the therapy parameter determination algorithm 4329.

The method 8000 auto-titrates the EPAP by maintaining and updating a "desired" EPAP value, which is a target value or set point towards which the actual EPAP is repeatedly adjusted. The desired EPAP is updated depending on the extent of inspiratory flow limitation determined by the inspiratory flow limitation determination algorithm 4324, M shape determined by the M-shape detection algorithm 4326, recent apneas detected by the apnea detection algorithm 4325, and the current EPAP.

The method 8000 auto-titrates the EPAP within a range [EPAPmin, EPAPmax]. The EPAP lower and upper limits EPAPmin and EPAPmax are settings of the RPT device 4000, set for example by hard-coding during configuration of the RPT device 4000 or by manual entry through the input device 4220.

There are interdependencies between the pressure support limits Amax and Amin, the EPAP limits EPAPmin and EPAPmax, and Plimit, where Plimit is an overall maximum pressure deliverable by the RPT device 4000. These interdependencies may be expressed as $$\text{EPAPMin} + A\text{Max} \leq P\text{limit}$$

$$\text{EPAPMax} + A\text{min} \leq P\text{limit}$$

During auto-EPAP ventilation therapy, pressure support A may be reduced (no lower than Amin) to allow the EPAP to increase to stabilise the upper airway. In other words, first priority is given to maintaining a stable upper airway with an appropriate EPAP, then to providing ventilation therapy.

The method 8000 starts at step 8010, which computes an increase ShapeRxIncrease to the EPAP based on abnormal inspiratory waveform shape, specifically the extent of inspiratory flow limitation determined by the inspiratory flow limitation determination algorithm 4324 and M-shape determined by the M-shape detection algorithm 4326. Step 8010 is referred to as the "Shape Doctor" as its output ShapeRxIncrease is a "prescription" based on the shape of the inspiratory portion of the respiratory flow rate waveform. Step 8010 is described in more detail below with reference to FIG. 8B.

The next step 8020 computes an increase ApneaRxIncrease to the EPAP based on one or more recent apneas detected by the apnea detection algorithm 4325. Step 8020 is referred to as the "Apnea Doctor" as its output ApneaRxIncrease is a "prescription" based on the severity of the one or more recent apneas. Step 8020 is described in more detail below with reference to FIG. 8E.

Step 8030 follows, at which the EPAP auto-titration method 8000 updates the desired EPAP using the current EPAP value and the increases ShapeRxIncrease and ApneaRxIncrease prescribed by the Shape Doctor (step 8010) and the Apnea Doctor (step 8020). Step 8030 is described in more detail below with reference to FIG. 8G.

The final step 8040 slews the current EPAP to the desired EPAP at a slew rate of either 1 cm H$_2$O per second (for increases in the current EPAP) or −1 cm H$_2$O (for decreases in the current EPAP). In one implementation, the current EPAP is not increased during inspiration (i.e. when the phase is between 0 and 0.5), but it may be decreased during inspiration.

7.6.2.1.1 Shape Doctor

FIG. 8B is a flow chart illustrating a method 8100 that may be used to implement step 8010 (the "Shape Doctor") of the method 8000.

The method 8100 starts at step 8105, which checks whether the expected normal ventilation Vnorm is less than a threshold, in one implementation set to 1 litre/minute. As mentioned above, the expected normal ventilation Vnorm may be the typical recent ventilation Vtyp returned by the typical recent ventilation determination algorithm 4328. If so ("Y"), step 8110 sets ShapeRxIncrease to zero, because such a low value indicates some kind of error condition, and it would be unwise to proceed with calculation of an EPAP increase.

Otherwise ("N"), step 8115 computes the current inspiratory and expiratory tidal volumes Vi and Ve from the respiratory flow rate signal Qr. Step 8120 averages the two tidal volumes Vi and Ve to obtain the average tidal volume Vt. The next step 8125 computes the "breathwise ventilation" (in litres/min) by multiplying the average tidal volume Vt by sixty seconds and dividing by the duration Ttot of the current breath. Step 8130 then divides the breathwise ventilation by the expected normal ventilation Vnorm to obtain a (unitless) value for the relative ventilation (relativeVentilation). If relativeVentilation is significantly less than one, the current breath is small in relation to the expected normal ventilation Vnorm, indicating significant breathwise hypoventilation. Step 8135 formalises this relation by computing a variable signifcantBreathHypoventilation that decreases from 1 to 0 as relativeVentilation increases above a hypoventilation threshold. In one implementation, step 8135 computes signifcantBreathHypoventilation as follows:

$$\text{significantBreathHypoventilation} = \text{FuzzyDeweight}(\\
\text{relativeVentilation},\\
\text{LOWER\_HYPOVENT\_THRESH}, 1.0,\\
\text{UPPER\_HYPOVENT\_THRESH}, 0.0\\
)$$

where LOWER_HYPOVENT_THRESH and UPPER_HYPOVENT_THRESH are constant thresholds, equal in one implementation to 0.2 and 0.8 respectively.

Conversely, if relativeVentilation is significantly greater than one, the current breath is large in relation to the expected normal ventilation Vnorm, indicating significant breathwise hyperventilation.

At the next step 8140, the method 8100 computes a variable recentBreathFlowLimitedHypovent from the current and recent values of signifcantBreathHypoventilation. The general effect of step 8140 is that recentBreathFlowLimitedHypovent is higher when there has been a recent persistence of significant breathwise hypoventilation in conjunction with flow-limited or M-shaped inspiratory waveforms over multiple breaths, rather than just a single-breath instance thereof. Step 8140 will be described in more detail below with reference to FIG. 8C.

The method 8000 continues at step 8145, which computes a fuzzy truth variable mShapeRxProportion reflecting the (real-valued) M-shape indicator variable RxProportion returned by the M-shape detection algorithm 4326. In one implementation, step 8145 takes the maximum of RxProportion and 0, in other words puts a floor of 0 under the value of RxProportion. Step 8150 then computes a fuzzy truth variable flowLimitedValue as the "fuzzy OR" of the fuzzy truth variables mShapeRxProportion (indicating the degree of M-shape) and flowLimitation (indicating the degree of flow limitation).

The next step 8155 computes a flow limitation threshold flowLimitedThreshold with which flowLimitedValue is to be compared. The flow limitation threshold flowLimitedThreshold is computed from the current value of EPAP in such a way that the flow limitation thresholdflowLimitedThreshold increases as the current value of EPAP increases. By this means, the degree of abnormality of inspiratory waveform shape required for the Shape Doctor to prescribe an increase of EPAP increases as EPAP itself increases. In one implementation, step 8155 computes flowLimitedThreshold as follows:

$$\text{flowLimitedThreshold} = \text{FuzzyDeweight}(\\
\text{EPAP},\\
\text{LOWER\_EPAP\_THRESH}, 0.0,\\
\text{MIDDLE\_EPAP\_THRESH}, 0.3,\\
\text{UPPER\_EPAP\_THRESH}, 0.8\\
)$$

where LOWER_EPAP_THRESH, MIDDLE_EPAP_THRESH, and UPPER_EPAP_THRESH are constant thresholds, equal in one implementation to 14 cm $H_2O$, 18 cm $H_2O$, and 20 cm $H_2O$ respectively.

The Shape Doctor's prescribed EPAP increase, ShapeRxIncrease, is set proportional to the amount (if any) by which between flowLimitedValue exceeds flowLimitedThreshold. The increase may be set as a function of one or more multipliers, such as a dynamically computed multiplier. Thus, the method 8100 may first compute any one or more of the following three multipliers on the constant of proportionality, and which may collectively be considered a multiplier. For example, step 8160 computes a base pressure-related multiplier flowLimitedRxMultiplier such that flowLimitedRxMultiplier, and hence the final prescription ShapeRxIncrease, generally decreases as the current EPAP increases. In one implementation, flowLimitedRxMultplier is computed as follows:

$$\text{flowLimitedRxMultiplier} = \text{FuzzyDeweight}(\\
\text{EPAP},\\
\text{LOWER\_MULT1\_THRESH}, 1.0,\\
\text{MIDDLE\_MULT1\_THRESH}, 0.7,\\
\text{MIDDLE2\_MULT1\_THRESH}, 0.4,\\
\text{UPPER\_MULT1\_THRESH}, 0.0,\\
)$$

where LOWER_MULT1_THRESH, MIDDLE_MULT1_THRESH, MIDDLE2_MULT1_THRESH, and UPPER_MULT1_THRESH are constant thresholds, equal in one implementation to 10 cm $H_2O$, 15 cm $H_2O$, 19 cm $H_2O$, and 20 cm $H_2O$ respectively.

Step 8165 computes a leak-related multiplier leakRxMultiplier such that leakRxMultiplier, and hence the prescription ShapeRxIncrease, generally decreases as the leak flow rate estimate Ql (from the leak flow rate estimation algorithm 4316) increases. In one implementation, leakRxMultiplier is computed as follows:

```
leakRxMultiplier = FuzzyDeweight(
    Ql,
    LOWER_LEAK_THRESH, 1.0,
    UPPER_LEAK_THRESH, 0.0
)
``` where LOWER_LEAK_THRESH and UPPER_LEAK_THRESH are constant thresholds, set in one implementation to 30 litres/minute and 60 litres/minute respectively.

Step 8170 then computes a ventilation-related multiplier flowLimRxPropRelVent based on the current breathwise ventilation relative to the expected normal ventilation Vnorm (expressed in relativeVentilation, computed at step 8130), the amount of flow limitation or M-shape (expressed in flowLimitedValue, computed at step 8150), and/or the amount of recent persistent flow-limited significant breathwise hypoventilation (expressed in recentBreathFlowLimitedHypovent, computed at step 8140). Step 8170 is described in more detail below with reference to FIG. 8D.

The final step 8175 computes the Shape Doctor's prescription ShapeRxIncrease by first checking whether flowLimitedValue exceeds flowLimitedThreshold. If not, ShapeRxIncrease is set to zero. Otherwise, step 8175 computes ShapeRxIncrease as follows:

ShapeRxIncrease=(flowLimitedValue−flowLimitedThreshold)*
flowLimitedRxMultiplier*leakRxMultiplier*
flowLimRxPropRelVent*EPAP_GAIN where EPAP_GAIN is a constant. In one implementation, EPAP_GAIN is set to 0.2 cm H$_2$O.

FIG. 8C is a flow chart illustrating a method 8200 that may be used to implement step 8140 of the method 8100 that computes a variable named recentBreathFlowLimitedHypovent. As mentioned above, the general effect of step 8140 is that recentBreathFlowLimitedHypovent is higher when there has been a recent persistence of flow-limited or M-shaped significant breathwise hypoventilation over multiple breaths, rather than just a single-breath instance thereof.

The method 8200 starts at step 8210, which computes a variable OHV by multiplying the maximum of the M-shape indicator RxProportion and the flow limitation indicator flowLimitation by signifcantBreathHypoventilation, which was computed at step 8135. OHV stands for obstructive (i.e. flow-limited) hypoventilation, of which the value of OHV is indicative for the current breath. Step 8210 stores the value of OHV at a current location in a circular buffer representing a smallish number of recent breaths. In one implementation, the circular buffer contains eight entries. Step 8220 then checks whether the circular buffer is full. If not ("N"), the method 8200 at step 8230 sets recentBreathFlowLimitedHypovent to zero as there is not enough stored information to indicate a recent persistence of flow-limited or M-shaped significant breathwise hypoventilation. Otherwise ("Y"), step 8240 applies adjacency weighting to each entry in the circular buffer. The adjacency weighting is a function of the entry and its predecessor entry in the circular buffer such that the adjacency weighted entry is highest when both entries are approximately equal and close to one. In one implementation, step 8240 computes the adjacency-weighted OHV as adjacencyWeightedOHV=OHV+(1−OHV)*Min(OHV, OHVPrev)

where OHVPrev is the predecessor entry of the current entry OHV in the circular buffer. In other implementations, other functions of OHV and OHVPrev may be used at step 8240, such as an arithmetic or geometric mean.

The next step 8250 of the method 8200 sums the squared values of adjacencyWeightedOHV over the circular buffer. In one implementation, each squared value is weighted by a weight that is highest for the current entry and decreases towards zero as the entries become less recent. In one implementation, the weightings (working backward through the circular buffer) are {1, 0.95, 0.9, 0.8, 0.7, 0.55, 0.4, 0.25}.

Finally, step 8260 computes recentBreathFlowLimitedHypovent as the square root of the sum of the (weighted) squared values divided by the sum of the weights used at step 8250 (if used, otherwise divided by the number of squared values). In other words, recentBreathFlowLimitedHypovent is a root mean squared value of the recent adjacency-weighted values of a flow-limited significant hypoventilation indicator (possibly with greatest weight given to the most recent value).

FIG. 8D is a flow chart illustrating a method 8300 that may be used to implement step 8170 of the method 8100. As mentioned above, the step 8170 computes the ventilation-related multiplier flowLimRxPropRelVent on the final prescription of the Shape Doctor based on the indicator relativeVentilation of the relative size of the current breath, the amount of flow limitation or M-shape (expressed in flowLimitedValue), and the indicator recentBreathFlowLimitedHypovent of the amount of recent persistent flow-limited breathwise hypoventilation.

The general effect of step 8170 is that flowLimRxPropRelVent generally has a neutral value of 1 but tends to decrease below 1 as the relative ventilation exceeds a flow limitation threshold that increases with the amount of flow limitation or M-shape. That is, the Shape Doctor's prescription tends to be discounted if relative hyperventilation is occurring. However, the amount of relative hyperventilation needed to discount the Shape Doctor's prescription increases as the severity of flow limitation or M-shape increases. If the relative ventilation is significantly less than one, flowLimRxPropRelVent increases, possibly above 1, thereby amplifying the Shape Doctor's prescription, in general proportion to the indicator recentBreathFlowLimitedHypovent of a recent persistence of flow-limited or M-shaped significant breathwise hypoventilation.

The method 8300 starts at step 8310, which checks whether the value of relativeVentilation (computed at step 8130) is greater than or equal to one, i.e. the breathwise ventilation is greater than or equal to the expected normal ventilation Vnorm. If so ("Y"), the method 8300 proceeds to step 8320, which computes a variable severeFlowLimitation to generally increase from 0 to 1 as the amount of flow limitation or M-shape, expressed in the variableflowLimitedValue, increases. In one implementation, step 8320 computes severeFlowLimitation as follows:

```
severeFlowLimitation = FuzzyDeweight(
    flowLimitedValue,
    LOWER_FL_THRESH, 0.0,
    UPPER_FL_THRESH, 1.0
)
``` where LOWER_FL_THRESH and UPPER_FL_THRESH are constant thresholds, equal in one implementation to 0.7 and 0.9 respectively.

The next step 8330 computes lower and upper relative ventilation thresholds lowerRelVentThreshold and upperRelVentThreshold on relative ventilation from the value of severeFlowLimitation computed at step 8320. The lower and upper relative ventilation thresholds lowerRelVent-Threshold and upperRelVentThreshold are at least 1.0 and increase generally proportionally to severeFlowLimitation. In one implementation, step 8330 computes the lower and upper relative ventilation thresholds lowerRelVentThreshold and upperRelVentThreshold from severeFlowLimitation as follows:

lowerRelVentThreshold=1+0.7*severeFlowLimitation upperRelVentThreshold=1.5+0.7*severeFlowLimitation Finally, step 8340 computes flowLimRxPropRelVent so as to generally decrease from 1 to 0 as relativeVentilation increases in relation to the lower and upper relative ventilation thresholds lowerRelVentThreshold and upperRelVentThreshold computed at step 8330. In one implementation, step 8340 computes flowLimRxPropRelVent as follows:

flowLimRxPropRelVent = FuzzyDeweight(
 relativeVentilation,
 lowerRelVentThreshold, 1.0,
 upperRelVentThreshold, 0.0
 )

Returning to step 8310, if step 8310 found that relativeVentilation was less than 1 ("N"), step 8350 checks whether the current breath is a significant hypoventilation, by checking whether the variable signifcantBreathHypoventilation, computed at step 8135, is greater than 0. (In an implementation described above, signifcantBreathHypoventilation is greater than zero only if relativeVentilation is less than UPPER_HYPOVENT_THRESH). If not ("N"), step 8370 sets flowLimRxPropRelVent to a neutral value of 1.0. Otherwise ("Y"), step 8360 computes flowLimRxPropRelVent to generally increase in proportion to the indicator recentBreathFlowLimitedHypovent of a recent persistence of flow-limited or M-shaped significant breathwise hypoventilation. In one implementation, step 8360 computes flowLimRxPropRelVent as follows:

flowLimRxPropRelVent=0.5+2*recentBreathFlowLimitedHypovent

The method 8300 then concludes.

7.6.2.1.2 Apnea Doctor

FIG. 8E is a flow chart illustrating a method 8400 that may be used to implement step 8020 (the "Apnea Doctor") of the method 8000.

As mentioned above, the purpose of the Apnea Doctor is to compute a prescribed EPAP increase ApneaRxIncrease based on apneas detected by the apnea detection algorithm 4325.

In one implementation, the apnea detection algorithm 4325 places its detected apneas (each characterised by start time, end time, and effective duration) in a single list of pending apneas as soon as they are ended.

The method 8400 therefore starts at step 8410 by sorting the list of pending apneas in ascending order of their start times. The next step 8420 removes any duplicates (i.e. apneas with the same start and end times) from the sorted list of pending apneas. Step 8430 follows, which removes from the sorted list any apneas that have already been processed by the Apnea Doctor.

At the next step 8440, the method 8400 resolves the (possibly overlapping) apneas in the sorted list into non-overlapping apneas. Step 8450 then processes the completed apneas in the sorted, non-overlapping list in ascending order of start time. The processing of an apnea at step 8450 is described in more detail below with reference to FIG. 8F. The processing of the apneas in the list at step 8450 results in a prescribed EPAP due to apneas, prescribedEPAP. Step 8460 then computes a prescribed EPAP increase due to apneas, ApneaRxIncrease, from prescribedEPAP and the current value of EPAP. In one implementation, step 8460 computes ApneaRxIncrease as follows:

ApneaRxIncrease=prescribedEPAP−EPAP−ShapeRxIncrease   (7)

In one implementation, step 8460 clips ApneaRxIncrease below to zero, so that ApneaRxIncrease cannot be negative. In an alternative implementation, step 8460 computes ApneaRxIncrease as follows:

ApneaRxIncrease=prescribedEPAP−EPAP   (8)

If step 8460 uses equation (7) to compute ApneaRxIncrease, the effect, when step 8030 computes the desired EPAP as described below, is to increase the desired EPAP by the greater of ApneaRxIncrease and ShapeRxIncrease. If step 8460 uses equation (8) to compute ApneaRxIncrease, the effect, when step 8030 computes the desired EPAP, is to increase the desired EPAP by the sum of ApneaRxIncrease and ShapeRxIncrease.

Step 8460 may also use the desired EPAP rather than the current EPAP in equations (7) and (8).

The method 8400 then concludes.

FIG. 8F is a flow chart illustrating a method 8500 of processing an apnea that may be used to implement step 8450 of the method 8400. The output of the method 8500 is a prescribed EPAP increase for the apnea, singleApneaIncrease, that broadly increases with the effective duration of the apnea.

One implementation of step 8450 of the method 8400 executes the method 8500 once for each apnea in the list. In this implementation, before the first iteration of the method 8500 to process the first apnea in the list, step 8450 sets the prescribed EPAP due to apneas (the output of step 8450), prescribedEPAP, to zero. After each iteration of the method 8500, step 8450 increments prescribedEPAP by the value of singleApneaIncrease returned by that iteration.

The method 8500 starts at step 8510, which determines whether the effective duration of the apnea is greater than or equal to a duration threshold, equal in one implementation to nine seconds. If not ("N"), the method 8500 ends at step 8590, which sets the prescribed EPAP increase singleApneaIncrease for the apnea to 0. Otherwise ("Y"), the method 8500 proceeds to step 8520, which computes a variable called HighApneaRolloffPressure, which is the value to which the method 8500 would increase the current EPAP if the apnea were infinite in effective duration. In one implementation, step 8520 computes HighApneaRolloffPressure as the maximum of EPAPmax+2 cm $H_2O$, and a minimum value of HighApneaRolloffPressure, a constant which in one implementation is set to 12 cm $H_2O$. HighApneaRolloffPressure may therefore be greater than the value of EPAPmax. The next step 8530 computes a rate constant for the approach of the EPAP to the HighApneaRolloffPressure, so as to generally decrease as HighApneaRolloffPressure increases. In one implementation of step 8530, the rate constant k (in units of $s^{-1}$) is computed as follows:

k=(1.333/60)*(10/HighApneaRolloffPressure)

Step 8540 follows, at which the method 8500 computes a variable EPAPIncreaseWeightingFactor so as to generally increase from 0 asymptotically towards 1 with the effective duration of the apnea. In one implementation, step 8540 computes EPAPIncreaseWeightingFactor using the rate constant k as follows:

EPAPIncreaseWeightingFactor=1−exp(−k*effectiveDuration)

The method 8500 concludes with step 8550, which computes singleApneaIncrease as the product of EPAPIncreaseWeightingFactor and the difference between HighApneaRolloffPressure and the current value of prescribedEPAP:

singleApneaIncrease=EPAPIncreaseWeightingFactor*(HighApneaRolloffPressure−prescribedEPAP)

FIG. 8G is a flow chart illustrating a method 8600 that may be used to implement step 8030 of the method 8000. As mentioned above, step 8030 updates the desired EPAP using the current EPAP and the EPAP increases ShapeRxIncrease and ApneaRxIncrease prescribed by the Shape Doctor (step 8010) and the Apnea Doctor (step 8020) respectively.

The method 8600 starts at step 8610, which checks whether ShapeRxIncrease or ApneaRxIncrease is greater than zero. If so ("Y"), step 8620 increases the desired EPAP by the sum of ShapeRxIncrease and ApneaRxIncrease. The next step 8630 then clips the increased desired EPAP to the range [EPAPmin, EPAPmax]. This is to say, step 8630 sets the desired EPAP to the minimum of its incremented value from step 8620 and EPAPmax, and to the maximum of its incremented value from step 8620 and EPAPmin.

If step 8610 found that neither the Shape Doctor nor the Apnea Doctor prescribed a positive increase in the EPAP ("N"), the method 8600 exponentially decays the desired EPAP towards EPAPmin. First, a decay factor decayFactor to scale the exponential decay is computed. This computation is done in one of two branches, conditioned on whether the current value of EPAP exceeds EPAPmin by 4 cm H$_2$O or less (checked at step 8640). If so ("Y"), the step 8650 sets decayFactor to the difference between the current EPAP and EPAPmin. If not ("N"), step 8660 computes decayFactor to rise more slowly as the difference between the current EPAP and EPAPmin increases. In one implementation of step 8660, the value of decayFactor is computed as follows, where the units of pressure are cm H$_2$O:

decayFactor=4+0.5*((current EPAP−EPAPmin)−4)

Finally, at step 8670 which follows either step 8660 or step 8650, the method 8600 reduces the desired EPAP by an amount that is proportional to the value of decayFactor computed at step 8650 or step 8660:

desired EPAP=desired EPAP−decayFactor*(1−exp(−timeDiff/timeConstant))

where timeDiff is the time elapsed (in seconds) since the last update of the desired EPAP, and timeConstant is the time constant of the decay, in seconds. In one implementation, timeConstant is 20 minutes*60.

FIG. 9A contains a graph 9000 illustrating an example of the behaviour of the EPAP auto-titration method 8000 of FIG. 8A in response to episodes of flow limitation. The graph 9000 contains a trace 9010 of treatment pressure Pt with fixed pressure support as indicated by the arrow 9015. The treatment pressure trace 9010 shows an increase 9025 in the EPAP in response to a first episode 9020 of flow limitation. Following the increase 9025 in the EPAP, a second episode 9030 of flow limitation occurs. The second episode 9030 results in a second increase 9035 in the EPAP. This second increase 9035 in the EPAP successfully resolves the flow limitation, resulting in an episode 9040 of normal breathing, which causes a gradual decrease 9045 of the EPAP. The dashed line 9050 indicates an upper limit EPAPmax on the EPAP. The dashed line 9060 indicates an overall upper limit Plimit on the treatment pressure Pt. The dashed line 9070 indicates a lower limit EPAPmin on the EPAP.

FIG. 9B contains a graph 9100 illustrating an example of the behaviour of the EPAP auto-titration method 8000 of FIG. 8A in response to a closed apnea. The graph 9100 contains an upper trace 9105 of treatment pressure Pt, and a lower trace 9110 of respiratory flow rate Qr. An apnea 9115 is detected, during which three probe breaths 9120 are delivered, each of duration Ti. Analysis of the respiratory flow rate Qr by the airway patency determination algorithm 4327 determines that the apnea 9115 is closed. At the termination 9125 of the apnea, the EPAP is increased at a fixed rate of 1 cm H$_2$O/sec during successive inspiratory portions 9130 until it reaches the desired EPAP 9135.

FIG. 9C contains a graph 9200 illustrating an example of the behaviour of the airway patency determination algorithm 4327 of FIG. 7H in response to a mixed apnea. The graph 9200 contains a trace 9205 of treatment pressure Pt, a trace 9210 of respiratory flow rate Qr, a trace 9215 indicative of the output of the airway patency determination algorithm 4327, and a trace 9220 indicative of the output of the apnea detection algorithm 4325. At the instant 9225, the respiratory flow rate falls dramatically, and the apnea detection trace 9220 rises shortly afterward at 9230 indicating an apnea state has been detected. The treatment pressure trace 9205 shows the delivery of the resulting series of probe breaths, the first probe breath being 9208. Analysis of the respiratory flow rate Qr by the airway patency determination algorithm 4327 determines that the apnea is initially closed, so the airway patency trace 9215 rises at the point 9235 to a value indicative of a closed airway. The flow rate trace 9210 then at the point 9240 begins to show a significant response to the probe breaths, for example the probe breath 9243. Analysis of the respiratory flow rate Qr by the airway patency determination algorithm 4327 determines that the apnea is open, so the airway patency trace 9215 falls at the point 9245 to a value indicative of an open airway. The flow rate trace 9210 then at the point 9250 begins to show no significant response to the probe breaths, for example the probe breath 9253. Analysis of the respiratory flow rate Qr by the airway patency determination algorithm 4327 determines that the apnea is closed, so the airway patency trace 9215 returns at the point 9255 to the value indicative of a closed airway.

FIG. 9D contains expansions of various sections of the graph 9200 of FIG. 9C. The trace 9300 is an expansion of the treatment pressure trace 9205 during the probe breath 9208, and the trace 9310 is an expansion of the respiratory flow rate trace 9210 during that probe breath 9208. The breath size indicator Sz for the probe breath 9208, as computed by step 7730 using the respiratory flow rate trace 9310, was below the lower threshold computed by step 7740, and the method 7700 therefore determined that the airway was closed at step 7770.

The trace 9320 is an expansion of the treatment pressure trace 9205 during the probe breath 9243, and the trace 9330 is an expansion of the respiratory flow rate trace 9210 during that probe breath 9243. The arrow 9321 indicates the extent of the trimmed inspiratory waveform returned by step 7710. The straight-line approximation 9322 to the trimmed inspiratory waveform has y-intercept 9324 and final value 9326. The inspiratory flatness ratio, computed at step 7810 as the ratio of 9326 to 9324, was found at step 7840 to be below the inspiratory threshold, so the method 7700 determined that the airway was open at step 7870.

The trace 9340 is an expansion of the treatment pressure trace 9205 during the probe breath 9253, and the trace 9350 is an expansion of the respiratory flow rate trace 9210 during that probe breath 9253. The arrow 9331 indicates the extent of the trimmed inspiratory waveform returned by step 7710. The straight-line approximation 9332 to the trimmed inspiratory waveform has y-intercept 9334 and final value 9336. The inspiratory flatness ratio, computed at step 7810 as the ratio of 9336 to 9334, was found at step 7840 to be above the inspiratory threshold, and the expiratory flatness ratio was likewise found at step 7850 to be above the expiratory threshold, so the method 7700 determined that the airway was closed at step 7860.

7.7 Glossary

For the purposes of the present technology disclosure, in certain forms of the present technology, one or more of the following definitions may apply. In other forms of the present technology, alternative definitions may apply.

7.7.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Respiratory Pressure Therapy (RPT): The application of a supply of air to an entrance to the airways at a treatment pressure that is typically positive with respect to atmosphere.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during expiration, and slightly lower during inspiration. In some forms, the pressure will vary between different respiratory cycles of the patient, for example, being increased in response to detection of indications of partial upper airway obstruction, and decreased in the absence of indications of partial upper airway obstruction.

Patient: A person, whether or not they are suffering from a respiratory disorder.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

7.7.2 Aspects of the Respiratory Cycle

Apnea: According to some definitions, an apnea is said to have occurred when flow falls below a predetermined threshold for a duration, e.g. 10 seconds. A closed apnea will be said to have occurred when, despite patient effort, some obstruction of the airway does not allow air to flow. An open apnea will be said to have occurred when an apnea is detected that is due to a reduction in breathing effort, or the absence of breathing effort, despite the airway being open (patent). A mixed apnea occurs when a reduction or absence of breathing effort coincides with an obstructed airway.

Breathing rate: The rate of spontaneous respiration of a patient, usually measured in breaths per minute.

Duty cycle, or inspiratory fraction: The ratio of inspiratory time, Ti, to total breath time, Ttot.

Effort (breathing): Breathing effort will be said to be the work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of a breathing cycle it may be described as inspiratory flow limitation. Where flow limitation occurs during an expiratory portion of the breathing cycle it may be described as expiratory flow limitation.

Types of flow-limited inspiratory waveforms:
  (i) (Classically) Flattened: Having a rise followed by a relatively flat portion, followed by a fall.
  (ii) M-shaped: Having two local peaks, one at the early part, and one at the late section, and a relatively flat portion between the two peaks.
  (iii) Chair-shaped: Having a single local peak, the peak being at the early part, followed by a relatively flat portion.
  (iv) Reverse-chair shaped: Having a relatively flat portion followed by single local peak, the peak being at the late section.

Hypopnea: A reduction in flow, but not a cessation of flow. In one form, a hypopnea may be said to have occurred when there is a reduction in flow below a threshold rate for a duration. A central hypopnea may be said to have occurred when a hypopnea is detected that is due to a reduction in breathing effort.

Hyperpnea: An increase in flow to a level higher than normal flow rate.

Hypoventilation: Hypoventilation is said to occur when the amount of gas exchange taking place over some timescale is below the current requirements of the patient.

Hyperventilation: Hyperventilation is said to occur when the amount of gas exchange taking place over some timescale is above the current requirements of the patient.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peakflow rate (Qpeak): The maximum value of flow rate during the inspiratory portion of the respiratory flow rate waveform.

Respiratoryflow rate, airflow rate, patient airflow rate, respiratory airflow rate (Qr): These synonymous terms may be understood to refer to the RPT device's estimate of respiratory airflow rate, as opposed to "true respiratory flow" or "true respiratory airflow", which is the actual respiratory flow rate experienced by the patient, usually expressed in litres per minute.

Tidal volume (Vt): The volume of air inspired or expired per breath during normal breathing, when extra effort is not applied. This quantity may be more specifically defined as inspiratory tidal volume (Vi) or expiratory tidal volume (Ve).

Inspiratory Time (Ti): The duration of the inspiratory portion of the respiratory flow rate waveform.

Expiratory Time (Te): The duration of the expiratory portion of the respiratory flow rate waveform.

Total (breath) Time (Ttot): The total duration between the start of the inspiratory portion of one respiratory flow rate waveform and the start of the inspiratory portion of the following respiratory flow rate waveform.

Typical recent ventilation: The value of ventilation around which recent values over some predetermined timescale tend to cluster, that is, a measure of the central tendency of the recent values of ventilation.

Upper airway obstruction (UAO): includes both partial and total upper airway obstruction. This may be associated with a state of flow limitation, in which the level of flow increases only slightly or may even decrease as the pressure difference across the upper airway increases (Starling resistor behaviour).

Ventilation (Vent): A measure of the total amount of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

7.7.3 RPT Device Parameters

Flow rate: The instantaneous volume (or mass) of air delivered per unit time. While flow rate and ventilation have the same dimensions of volume or mass per unit time, flow rate is measured over a much shorter period of time. In some cases, a reference to flow rate will be a reference to a scalar quantity, namely a quantity having magnitude only. In other cases, a reference to flow rate will be a reference to a vector quantity, namely a quantity having both magnitude and direction. Where it is referred to as a signed quantity, a flow rate may be nominally positive for the inspiratory portion of a breathing cycle of a patient, and hence negative for the expiratory portion of the breathing cycle of a patient. Flow rate will be given the symbol Q. 'Flow rate' is sometimes shortened to simply 'flow'. Total flow rate, Qt, is the flow rate of air leaving the RPT device. Vent flow rate, Qv, is the flow rate of air leaving a vent to allow washout of expired gases. Leak flow rate, Ql, is the flow rate of leak from a patient interface system. Respiratory flow rate, Qr, is the flow rate of air that is received into the patient's respiratory system.

Leak: The word leak will be taken to be an unintended flow of air. In one example, leak may occur as the result of an incomplete seal between a mask and a patient's face. In another example leak may occur in a swivel elbow to the ambient.

Pressure: Force per unit area. Pressure may be measured in a range of units, including cm $H_2O$ (centimetres of water), g-f/cm$^2$, and hectopascals (hPa). 1 cm $H_2O$ is equal to 1 g-f/cm$^2$ and is approximately 0.98 hPa. In this specification, unless otherwise stated, pressure is given in units of cm $H_2O$. The pressure in the patient interface is given the symbol Pm, while the treatment pressure, which represents a target value to be achieved by the mask pressure Pm at the current instant of time, is given the symbol Pt.

7.7.4 Terms for Ventilators

Backup rate: A parameter of a ventilator that establishes the minimum breathing rate (typically in number of breaths per minute) that the ventilator will deliver to the patient, if not triggered by spontaneous respiratory effort.

Cycling: The termination of a ventilator's inspiratory phase. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired mask pressure which the ventilator will attempt to achieve at a given time.

End expiratory pressure (EEP): Desired mask pressure which the ventilator will attempt to achieve at the end of the expiratory portion of the breath. If the pressure waveform template I(D) is zero-valued at the end of expiration, i.e. $\Pi(\Phi)=0$ when $\Phi=1$, the EEP is equal to the EPAP.

Inspiratory positive airway pressure (IPAP): Maximum desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP−EPAP). In some contexts pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Spontaneous/Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggering: When a ventilator delivers a breath of air to a spontaneously breathing patient, it is said to be triggered to do so at the initiation of the respiratory portion of the breathing cycle by the patient's efforts.

Ventilator: A mechanical device that provides pressure support to a patient to perform some or all of the work of breathing.

7.7.5 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

7.7.6 Mathematical Terms

Fuzzy logic is used in a number of places in this disclosure. The following is used to indicate a fuzzy membership function, which outputs a "fuzzy truth variable" in the range [0, 1], 0 representing "fuzzy false" and 1 representing "fuzzy true":

FuzzyMember (ActualQuantity, ReferenceQuantity1, FuzzyTruthValueAtReferenceQuantity1, ReferenceQuantity2, FuzzyTruthValueAtReferenceQuantity2, . . . , ReferenceQuantityN, FuzzyTruthValueAtReferenceQuantityN)

A fuzzy membership function is defined as $$FuzzyMember(x, x_1, f_1, x_2, f_2, \ldots, x_N, f_N) =$$
$$\begin{cases} f_1, & x < x_1 \\ f_N, & x \geq x_N \\ InterpOnInterval(x, x_k, f_k, x_{k+1}, f_{k+1}), & x_k \leq x < x_{k+1}, 1 \leq k \leq N \end{cases}$$

where $$InterpOnInterval(x, x_k, f_k, x_{k+1}, f_{k+1}) =$$
$$\begin{cases} f_k + \dfrac{(f_{k+1} - f_k)(x - x_k)}{x_{k+1} - x_k}, & x_k \neq x_{k+1} \\ f_k & \text{otherwise} \end{cases}$$

the $f_j$ are fuzzy truth variables, and x and the $x_j$ are real numbers.

The function "FuzzyDeweight" is defined in the same way as "FuzzyMember", except that the values $f_k$ are interpreted as real numbers rather than fuzzy truth variables, and the output is also a real number.

The "fuzzy OR" of fuzzy truth variables is the maximum of those values; the "fuzzy AND" of fuzzy truth variables is the minimum of these values. These operations on two or more fuzzy truth variables will be indicated by the names FuzzyOr and FuzzyAnd. It is to be understood that other typical definitions of these fuzzy operations would work similarly in the present technology.

Exponential decay towards zero with a time that during any period of decay starting at time t=T, the value of the decaying quantity V is given by $$V(t) = V(T) * \exp\left(-\frac{t - T}{\tau}\right)$$

Exponential decay is sometimes parametrised by a rate constant k rather than a time constant $\tau$. A rate constant k gives the same decay function as a time constant $\tau$ if k=1/$\tau$.

The inner product of two functions $f$ and g on some interval I is defined as $$\langle f, g \rangle_I = \int_I f(t)g(t)dt$$

7.8 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" (etc.) may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

7.9 Reference Label List

| | |
|---|---|
| patient | 1000 |
| patient interface | 3000 |
| non - invasive patient interface | 3000 |
| seal - forming structure | 3100 |
| plenum chamber | 3200 |
| structure | 3300 |
| vent | 3400 |
| connection port | 3600 |
| forehead support | 3700 |
| RPT device | 4000 |
| external housing | 4010 |
| upper portion | 4012 |
| portion | 4014 |
| panel | 4015 |
| chassis | 4016 |
| handle | 4018 |
| pneumatic block | 4020 |
| pneumatic components | 4100 |
| air filter | 4110 |
| inlet air filter | 4112 |
| outlet air filter | 4114 |
| inlet muffler | 4122 |
| outlet muffler | 4124 |
| pressure generator | 4140 |
| controllable blower | 4142 |
| motor | 4144 |
| air circuit | 4170 |
| supplemental oxygen | 4180 |
| electrical components | 4200 |
| Printed Circuit Board Assembly | 4202 |
| electrical power supply | 4210 |
| input device | 4220 |
| central controller | 4230 |
| clock | 4232 |
| therapy device controller | 4240 |
| protection circuits | 4250 |
| memory | 4260 |
| transducers | 4270 |
| pressure sensor | 4272 |
| flow rate sensor | 4274 |
| motor speed transducer | 4276 |
| data communication interface | 4280 |
| remote external communication network | 4282 |
| local external communication network | 4284 |
| remote external device | 4286 |
| local external device | 4288 |
| output devices | 4290 |
| display driver | 4292 |
| display | 4294 |
| algorithms | 4300 |
| pre-processing module | 4310 |
| pressure compensation algorithm | 4312 |
| vent flow rate estimation | 4314 |
| leak flow rate estimation algorithm | 4316 |
| respiratory flow rate estimation algorithm | 4318 |
| therapy engine module | 4320 |
| phase determination algorithm | 4321 |
| waveform determination algorithm | 4322 |
| ventilation determination algorithm | 4323 |
| inspiratory flow limitation detection | 4324 |
| apnea detection algorithm | 4325 |
| M - shape detection algorithm | 4326 |
| airway patency determination algorithm | 4327 |
| typical recent ventilation determination | 4328 |
| therapy parameter determination algorithm | 4329 |
| therapy control module | 4330 |
| humidifier | 5000 |
| humidifier inlet | 5002 |
| humidifier outlet | 5004 |
| humidifier base | 5006 |
| humidifier reservoir | 5110 |
| humidifier reservoir dock | 5130 |
| heating element | 5240 |
| humidifier controller | 5250 |
| method | 7000 |
| step | 7010 |
| step | 7020 |
| step | 7030 |
| step | 7040 |
| method | 7100 |
| step | 7110 |
| step | 7120 |
| step | 7130 |
| step | 7140 |
| step | 7150 |
| step | 7160 |
| step | 7170 |
| step | 7180 |
| method | 7200 |
| step | 7210 |

-continued

| | |
|---|---|
| step | 7220 |
| step | 7230 |
| step | 7240 |
| step | 7250 |
| step | 7260 |
| method | 7300 |
| step | 7310 |
| step | 7320 |
| step | 7330 |
| step | 7340 |
| step | 7350 |
| step | 7360 |
| step | 7370 |
| step | 7375 |
| step | 7380 |
| step | 7390 |
| method | 7400 |
| step | 7410 |
| step | 7420 |
| step | 7440 |
| step | 7450 |
| step | 7455 |
| step | 7460 |
| step | 7465 |
| step | 7470 |
| step | 7475 |
| method | 7500 |
| step | 7510 |
| step | 7520 |
| step | 7530 |
| step | 7535 |
| step | 7540 |
| step | 7550 |
| step | 7560 |
| step | 7570 |
| step | 7580 |
| method | 7600 |
| step | 7610 |
| steps | 7615 |
| steps | 7620 |
| step | 7630 |
| step | 7635 |
| step | 7640 |
| step | 7645 |
| step | 7650 |
| step | 7655 |
| step | 7660 |
| step | 7665 |
| step | 7670 |
| step | 7680 |
| step | 7685 |
| step | 7690 |
| method | 7700 |
| step | 7710 |
| step | 7720 |
| step | 7730 |
| step | 7740 |
| step | 7750 |
| step | 7760 |
| step | 7770 |
| step | 7780 |
| step | 7790 |
| step | 7810 |
| step | 7820 |
| step | 7830 |
| step | 7840 |
| step | 7850 |
| step | 7860 |
| step | 7870 |
| method | 8000 |
| step | 8010 |
| step | 8020 |
| step | 8030 |
| step | 8040 |
| method | 8100 |
| step | 8105 |
| step | 8110 |
| step | 8115 |
| step | 8120 |

-continued

| | |
|---|---|
| step | 8125 |
| step | 8130 |
| step | 8135 |
| step | 8140 |
| step | 8145 |
| step | 8150 |
| step | 8155 |
| step | 8160 |
| step | 8165 |
| step | 8170 |
| step | 8175 |
| method | 8200 |
| step | 8210 |
| step | 8220 |
| step | 8230 |
| step | 8240 |
| step | 8250 |
| step | 8260 |
| method | 8300 |
| step | 8310 |
| step | 8320 |
| step | 8330 |
| step | 8340 |
| step | 8350 |
| step | 8360 |
| step | 8370 |
| method | 8400 |
| step | 8410 |
| step | 8420 |
| step | 8430 |
| step | 8440 |
| step | 8450 |
| step | 8460 |
| method | 8500 |
| step | 8510 |
| step | 8520 |
| step | 8530 |
| step | 8540 |
| step | 8550 |
| step | 8590 |
| method | 8600 |
| step | 8610 |
| step | 8620 |
| step | 8630 |
| step | 8640 |
| step | 8650 |
| step | 8660 |
| step | 8670 |
| graph | 9000 |
| treatment pressure trace | 9010 |
| arrow | 9015 |
| first episode | 9020 |
| increase | 9025 |
| second episode | 9030 |
| second increase | 9035 |
| episode | 9040 |
| gradual decrease | 9045 |
| dashed line | 9050 |
| dashed line | 9060 |
| dashed line | 9070 |
| graph | 9100 |
| upper trace | 9105 |
| trace | 9110 |
| apnea | 9115 |
| breaths | 9120 |
| termination | 9125 |
| inspiratory portions | 9130 |
| EPAP | 9135 |
| graph | 9200 |
| treatment pressure trace | 9205 |
| probe breath | 9208 |
| flow rate trace | 9210 |
| airway patency trace | 9215 |
| apnea detection trace | 9220 |
| instant | 9225 |
| point | 9235 |
| point | 9240 |
| probe breath | 9243 |
| point | 9245 |

-continued

| | |
|---|---|
| point | 9250 |
| probe breath | 9253 |
| point | 9255 |
| trace | 9300 |
| respiratory flow rate trace | 9310 |
| trace | 9320 |
| arrow | 9321 |
| straight - line approximation | 9322 |
| y - intercept | 9324 |
| final value | 9326 |
| trace | 9330 |
| arrow | 9331 |
| straight - line approximation | 9332 |
| y - intercept | 9334 |
| final value | 9336 |
| trace | 9340 |
| trace | 9350 |

The invention claimed is:

1. A method of determining patency of an airway during an apnea of a patient, the method comprising:
controlling a pressure generator to deliver one or more probe breaths to the patient during the apnea; and
determining patency of the airway from a signal representative of respiratory flow rate of the patient during the apnea, wherein the determining comprises an evaluation of a plurality of portions of a waveform of the respiratory flow rate signal that is in response to at least one of the one or more probe breaths,
wherein the determining patency is dependent on comparisons between outputs of functions of the plurality of portions of the waveform and a plurality of dynamic thresholds.

2. The method of claim 1, wherein a dynamic threshold of the plurality of dynamic thresholds is computed as a function of a breath size indicator.

3. The method of claim 2, wherein the dynamic threshold linearly increases as a function of the breath size indicator.

4. The method of claim 2, wherein the dynamic threshold of the plurality of dynamic thresholds is computed as a function of a correlation coefficient.

5. The method of claim 2, wherein the determining patency of the airway comprises determining the airway to be open if an inspiratory or expiratory flatness ratio is below the dynamic threshold.

6. The method of claim 5, wherein the inspiratory or expiratory flatness ratio is computed as a final value of a straight-line approximation to a portion of the plurality of portions divided by an initial value of the straight-line approximation to the portion of the plurality of portions.

7. The method of claim 2, wherein the function of the breath size indicator is a relative size indicator computed from an indicator of the size of the respiratory flow rate in response to the at least one probe breath, an upper threshold, and a lower threshold.

8. The method of claim 1, wherein the portions of the waveform comprise inspiratory and expiratory portions.

9. The method of claim 8, wherein the outputs of functions of the plurality of portions of the waveform comprise an expiratory flatness ratio.

10. The method of claim 8, wherein the outputs of functions of the plurality of portions of the waveform comprise an inspiratory flatness ratio.

11. Apparatus for treating a respiratory disorder in a patient, comprising:
a pressure generator configured to deliver a flow of air at positive pressure to an airway of the patient through a patient interface;
a sensor configured to generate a signal representative of respiratory flow rate of the patient; and
a controller configured to:
control the pressure generator to deliver ventilation therapy through the patient interface;
control the pressure generator to deliver one or more probe breaths to the patient during detection of an apnea of the patient; and
determine patency of the airway from the signal representative of respiratory flow rate of the patient during the detection of the apnea, wherein to determine patency the controller is configured to evaluate a plurality of portions of a waveform of the respiratory flow rate signal that is in response to at least one of the one or more probe breaths, and wherein the determination of patency is dependent on comparisons between outputs of functions of the plurality of portions of the waveform and a plurality of dynamic thresholds.

12. The apparatus of claim 11, wherein a dynamic threshold of the plurality of dynamic thresholds is computed by the controller as a function of a breath size indicator.

13. The apparatus of claim 12, wherein the dynamic threshold linearly increases as a function of the breath size indicator.

14. The apparatus of claim 12, wherein the dynamic threshold of the plurality of dynamic thresholds is computed as a function of a correlation coefficient.

15. The apparatus of claim 12, wherein the determining patency of the airway comprises determining the airway to be open if an inspiratory or expiratory flatness ratio is below the dynamic threshold.

16. The apparatus of claim 15, wherein the inspiratory or expiratory flatness ratio is computed as a final value of a straight-line approximation to a portion of the plurality of portions divided by an initial value of the straight-line approximation to the portion of the plurality of portions.

17. The apparatus of claim 12, wherein the function of the breath size indicator is a relative size indicator computed from an indicator of the size of the respiratory flow rate in response to the at least one probe breath, an upper threshold, and a lower threshold.

18. The apparatus of claim 11, wherein the portions of the waveform comprise inspiratory and expiratory portions.

19. The apparatus of claim 18, wherein the outputs of functions of the plurality of portions of the waveform comprise an expiratory flatness ratio.

20. The apparatus of claim 18, wherein the outputs of functions of the plurality of portions of the waveform comprise an inspiratory flatness ratio.

* * * * *